(12) United States Patent
Kamogawa et al.

(10) Patent No.: US 8,470,992 B2
(45) Date of Patent: Jun. 25, 2013

(54) ANTI-ILT7 ANTIBODY

(75) Inventors: Yumiko Kamogawa, Tokyo (JP); Minkwon Cho, Tokyo (KR); Naoko Arai, Tokyo (JP); Koji Ishida, Tokyo (JP)

(73) Assignee: SBI Biotech Co., Ltd., Tokyo (JP)

( * ) Notice: Subject to any disclaimer, the term of this patent is extended or adjusted under 35 U.S.C. 154(b) by 0 days.

(21) Appl. No.: 13/302,291

(22) Filed: Nov. 22, 2011

(65) Prior Publication Data

US 2012/0135003 A1 May 31, 2012

Related U.S. Application Data

(62) Division of application No. 12/064,957, filed as application No. PCT/JP2006/325391 on Dec. 20, 2006, now Pat. No. 8,084,585.

(30) Foreign Application Priority Data

Dec. 20, 2005 (JP) ................................ 2005-366465

(51) Int. Cl.
*C07H 21/04* (2006.01)
(52) U.S. Cl.
USPC ...................................................... 536/23.53
(58) Field of Classification Search
None
See application file for complete search history.

(56) References Cited

U.S. PATENT DOCUMENTS

2003/0148316 A1  8/2003  Lipford et al.

FOREIGN PATENT DOCUMENTS

| WO | WO 03/012061 A2 | 2/2003 |
| WO | WO 2004/023973 A3 | 3/2004 |
| WO | WO 2006/013107 | 2/2006 |

OTHER PUBLICATIONS

Blanco, P. et al., "Induction of Dendritic Cell Differentiation by IFN-α in Systemic Lupus Erythematosus," *Science*, Nov. 16, 2001, vol. 294, pp. 1540-1543.
Blasius, A. et al., "A cell-surface molecule selectively expressed on murine natural interferon-producing cells that blocks secretion of interferon-alpha," *Blood*, Jun. 1, 2004, vol. 103(11):4201-4206.
Cao, W. et al., "Plasmacytoid dendritic cell-specific receptor ILT7-Fc epsilonRI gamma inhibits Toll-like receptor-induced interferon production," *J. Exp. Med.*, Jun. 2006, vol. 203(6), pp. 1399-1405.
Colonna, M. et al., "A family of inhibitory and activating Ig-like receptors that modulate function of lymphoid and myeloid cells," *Seminars in Immunology*, 2000, vol. 12, pp. 121-127.
Hopkins & Meager, "Cytokines in synovial fluid: II. The presence of tumour necrosis factor and interferon," *Clin. Exp. Immunol.*, 1988, vol. 73, pp. 88-92.
Ju, X. et al , "Immunoglobulin-like transcripts ILT2, ILT3 and ILT7 are expressed by human dendritic cells and down-regulated following activation," *Gene*, 2004, vol. 331, pp. 159-164.
Kamogawa-Schifter, Y. et al., "Ly49Q defines 2 pDC subsets in mice," *Blood*, 2005, vol. 105:2787-2792.
Nakajima, H. et al., "Cutting Edge: Human Myeloid Cells Express an Activating ILT Receptor (ILT1) That Associates with Fc Receptor gamma-Chain,"*J. Immunol.*, 1999, vol. 162(1), pp. 5-8.
Nestle, F. et al., "Plasmacytoid predendritic cells initiate psoriasis through interferon-α production," *J. Exp. Med.*, Jul. 4, 2005, vol. 202(1):135-143.
Pérez, A. et al., "Myasthenia Gravis Induced by Alpha-Interferon Therapy," *Am J Hematol.*, Aug. 1995, vol. 49(4):365-366.
Shiozawa, S. et al., "Interferon-alpha in Lupus Psychosis," *Arthritis and Rheumatism*, Apr. 1992, vol. 35(4):417-422.
Vales-Gomez, M. et al., "Genetic variability of the major histocompatibility complex class I homologue encoded by human cytomegalovirus leads to differential binding to the inhibitory receptor ILT2," *Journal of Virology*, Feb. 2005, vol. 79(4), pp. 2251-2260.
Wada, M. et al.,"Antithyroid Peroxidase Antibody and Development of Silent Thyroiditis during Interferon-α2a Treatment of Chronic Hepatiitis C", Am J. Gastroenterol. Aug. 1995, vol. 90(8):1366-1367.
Wilson, L. et al., "Autoimmune Disease Complicating Antiviral Therapy for Hepatitis C Virus Infection," *Seminars in Arthritis and Rheumatism*, Dec. 2002, vol. 32(3):163-173.
Kameda et al., 1993, J. Histo and Cyto. vol. 41:235-243.
Klimka et al., 2000, Brit. J. Canc. vol. 83:252-260.
Carrington, Mary et al., The KIR Gene Cluster, pp. 1-48, 2003.
Dzionek, Andrzej et al., 2001, "BDCA-2, a Novel Plasmacytoid Dendritic Cell-specific Type II C-type Lectin, Mediates Antigen Capture and Is a Potent Inhibitor of Interferon α/β Induction", J. Exp. Medicine, 194(12):1823-1834.
Internationl Search Report for corresponding PCT/JP2006/325391 dated Jan. 23, 2007.
Supplementary European Search Report for corresponding EP 06 84 2945 dated Jan. 19, 2010.
Young, Neil T. et la., 2001, "Conserved organization of the *ILT/LIR* gene family within the polymorphic human leukocyte receptor complex", Immunogenetics, 53:270-278.

*Primary Examiner* — Amy Juedes

(57) ABSTRACT

An antibody binding to IPC was obtained by using an animal cell in which a cell membrane protein associatable with ILT7 was co-expressed as an immunogen. The antibody of the invention has a high specificity which allows immunological distinction between other ILT family molecules and ILT7. The anti-ILT7 antibody of the invention bound to IPC and inhibited the activity thereof. With the anti-ILT7 antibody of the invention, the IPC activity can be inhibited and an interferon-related disease can be treated or prevented. ILT7 expression is maintained even in IPC in the presence of IFNα. Therefore, an inhibitory action of IPC activity by the anti-ILT7 antibody can be expected even in an autoimmune disease patient with an increased production of IFNα.

4 Claims, 17 Drawing Sheets

(a) Signal sequence

MTLILTSLLFFGLSLGPRTRVQAENLPKPILWAEPGPVITWHNPVTIWCQGTLEAQGYRL
DKEGNSMSRHILKTLESENKVKLSIPSMMWEHAGRYHCYYQSPAGWSEPSDPLELVVTAY
SRPTLSALPSPVVTSGVNVTLRCASRLGLGRFTLIEEGDHRLSWTLNSHQHNHGKFQALF
PMGPLTFSNRGTFRCYGYENNTPYVWSEPSDPLQLLVSGVSRKPSLLTLQGPVVTPGENL
TLQCGSDVGYIRYTLYKEGADGLPQRPGRQPQAGLSQANFTLSPVSRSYGGQYRCYGAHN
VSSEWSAPSDPLDILIAGQISDRPSLSVQPGPTVTSGEKVTLLCQSWDPMFTFLLTKEGA
AHPPLRLRSMYGAHKYQAEFPMSPVTSAHAGTYRCYGSRSSNPYLLSHPSEPLELVVSGA
TETLNPAQKKSDSKTAPHLQDYTVENLIRMGVAGLVLLFLGILLFEAQHSQRSPPRCSQE
ANSRKDNAPFRVVEPWEQI (SEQ ID NO:2) Transmembrane region (TM)

(b)

N-FLAG ILT7(57KDa)

| Signal sequence | FLAG tag | | TM | |

C-FLAG ILT7(57KDa)

| Signal sequence | | TM | FLAG tag |

SEQUENCE LISTING

<160> NUMBER OF SEQ ID NOS: 86

<210> SEQ ID NO 1
<211> LENGTH: 1577
<212> TYPE: DNA
<213> ORGANISM: Homo sapiens
<220> FEATURE:
<221> NAME/KEY: CDS
<222> LOCATION: (24)..(1520)
<220> FEATURE:
<221> NAME/KEY: sig_peptide
<222> LOCATION: (24)..(71)
<220> FEATURE:
<221> NAME/KEY: mat_peptide
<222> LOCATION: (72)..(1520)

<400> SEQUENCE: 1

```
cagggccagg aggaggagat gcc atg acc ctc att ctc aca agc ctg ctc ttc      53
                        Met Thr Leu Ile Leu Thr Ser Leu Leu Phe
                        -15                  -10
```

```
ttt ggg ctg agc ctg ggc ccc agg acc cgg gtg cag gca gaa aac cta    101
Phe Gly Leu Ser Leu Gly Pro Arg Thr Arg Val Gln Ala Glu Asn Leu
     -5              -1   1              5                  10 ccc aaa ccc atc ctg tgg gcc gag cca ggt ccc gtg atc acc tgg cat    149
Pro Lys Pro Ile Leu Trp Ala Glu Pro Gly Pro Val Ile Thr Trp His
                15              20                  25 aac ccc gtg acc atc tgg tgt cag ggc acc ctg gag gcc cag ggg tac    197
Asn Pro Val Thr Ile Trp Cys Gln Gly Thr Leu Glu Ala Gln Gly Tyr
         30              35                  40 cgt ctg gat aaa gag gga aac tca atg tcg agg cac ata tta aaa aca    245
Arg Leu Asp Lys Glu Gly Asn Ser Met Ser Arg His Ile Leu Lys Thr
             45              50              55 ctg gag tct gaa aac aag gtc aaa ctc tcc atc cca tcc atg atg tgg    293
Leu Glu Ser Glu Asn Lys Val Lys Leu Ser Ile Pro Ser Met Met Trp
     60              65              70 gaa cat gca ggg cga tat cac tgt tac tat cag agc cct gca ggc tgg    341
Glu His Ala Gly Arg Tyr His Cys Tyr Tyr Gln Ser Pro Ala Gly Trp
75          80              85              90 tca gag ccc agc gac ccc ctg gag ctg gtg gtg aca gcc tac agc aga    389
Ser Glu Pro Ser Asp Pro Leu Glu Leu Val Val Thr Ala Tyr Ser Arg
                 95              100             105 ccc acc ctg tcc gca ctg cca agc cct gtg gtg acc tca gga gtg aac    437
Pro Thr Leu Ser Ala Leu Pro Ser Pro Val Val Thr Ser Gly Val Asn
             110             115             120 gtg acc ctc cgg tgt gcc tca cgg ctg gga ctg ggc agg ttc act ctg    485
Val Thr Leu Arg Cys Ala Ser Arg Leu Gly Leu Gly Arg Phe Thr Leu
         125             130             135 att gag gaa gga gac cac agg ctc tcc tgg acc ctg aac tca cac caa    533
Ile Glu Glu Gly Asp His Arg Leu Ser Trp Thr Leu Asn Ser His Gln
     140             145             150 cac aac cat gga aag ttc cag gcc ctg ttc ccc atg ggc ccc ctg acc    581
His Asn His Gly Lys Phe Gln Ala Leu Phe Pro Met Gly Pro Leu Thr
155             160             165             170 ttc agc aac agg ggt aca ttc aga tgc tac ggc tat gaa aac aac acc    629
Phe Ser Asn Arg Gly Thr Phe Arg Cys Tyr Gly Tyr Glu Asn Asn Thr
             175             180             185 cca tac gtg tgg tcg gaa ccc agt gac ccc ctg cag cta ctg gtg tca    677
Pro Tyr Val Trp Ser Glu Pro Ser Asp Pro Leu Gln Leu Leu Val Ser
         190             195             200 ggc gtg tct agg aag ccc tcc ctc ctg acc ctg cag ggc cct gtc gtg    725
Gly Val Ser Arg Lys Pro Ser Leu Leu Thr Leu Gln Gly Pro Val Val
     205             210             215 acc ccc gga gag aat ctg acc ctc cag tgt ggc tct gat gtc ggc tac    773
Thr Pro Gly Glu Asn Leu Thr Leu Gln Cys Gly Ser Asp Val Gly Tyr
220             225             230 atc aga tac act ctg tac aag gag ggg gcc gat ggc ctc ccc cag cgc    821
Ile Arg Tyr Thr Leu Tyr Lys Glu Gly Ala Asp Gly Leu Pro Gln Arg
235             240             245             250 cct ggc cgg cag ccc cag gct ggg ctc tcc cag gcc aac ttc acc ctg    869
Pro Gly Arg Gln Pro Gln Ala Gly Leu Ser Gln Ala Asn Phe Thr Leu
             255             260             265 agc cct gtg agc cgc tcc tac ggg ggc cag tac aga tgc tac ggc gca    917
Ser Pro Val Ser Arg Ser Tyr Gly Gly Gln Tyr Arg Cys Tyr Gly Ala
         270             275             280 cac aac gtc tcc tcc gag tgg tcg gcc ccc agt gac ccc ctg gac atc    965
His Asn Val Ser Ser Glu Trp Ser Ala Pro Ser Asp Pro Leu Asp Ile
     285             290             295 ctg atc gca gga cag atc tct gac aga ccc tcc ctc tca gtg cag ccg   1013
Leu Ile Ala Gly Gln Ile Ser Asp Arg Pro Ser Leu Ser Val Gln Pro
300             305             310
```

```
ggc ccc acg gtg acc tca gga gag aag gtg acc ctg ctg tgt cag tca    1061
Gly Pro Thr Val Thr Ser Gly Glu Lys Val Thr Leu Leu Cys Gln Ser
315                 320                 325                 330 tgg gac ccg atg ttc act ttc ctt ctg acc aag gag ggg gca gcc cat    1109
Trp Asp Pro Met Phe Thr Phe Leu Leu Thr Lys Glu Gly Ala Ala His
                335                 340                 345 ccc ccg ttg cgt ctg aga tca atg tac gga gct cat aag tac cag gct    1157
Pro Pro Leu Arg Leu Arg Ser Met Tyr Gly Ala His Lys Tyr Gln Ala
            350                 355                 360 gaa ttc ccc atg agt cct gtg acc tca gcc cac gcg ggg acc tac agg    1205
Glu Phe Pro Met Ser Pro Val Thr Ser Ala His Ala Gly Thr Tyr Arg
        365                 370                 375 tgc tac ggc tca cgc agc tcc aac ccc tac ctg ctg tct cac ccc agt    1253
Cys Tyr Gly Ser Arg Ser Ser Asn Pro Tyr Leu Leu Ser His Pro Ser
    380                 385                 390 gag ccc ctg gag ctc gtg gtc tca gga gca act gag acc ctc aat cca    1301
Glu Pro Leu Glu Leu Val Val Ser Gly Ala Thr Glu Thr Leu Asn Pro
395                 400                 405                 410 gca caa aag aag tca gat tcc aag act gcc cca cac ctc cag gat tac    1349
Ala Gln Lys Lys Ser Asp Ser Lys Thr Ala Pro His Leu Gln Asp Tyr
                415                 420                 425 aca gtg gag aat ctc atc cgc atg ggt gtg gct ggc ttg gtc ctg ctg    1397
Thr Val Glu Asn Leu Ile Arg Met Gly Val Ala Gly Leu Val Leu Leu
            430                 435                 440 ttc ctc ggg att ctg tta ttt gag gct cag cac agc cag aga agc ccc    1445
Phe Leu Gly Ile Leu Leu Phe Glu Ala Gln His Ser Gln Arg Ser Pro
        445                 450                 455 cca agg tgc agc cag gag gca aac agc aga aag gac aat gca ccc ttc    1493
Pro Arg Cys Ser Gln Glu Ala Asn Ser Arg Lys Asp Asn Ala Pro Phe
    460                 465                 470 aga gtg gtg gag cct tgg gaa cag atc tgatgatctg aggaggttct          1540
Arg Val Val Glu Pro Trp Glu Gln Ile
475                 480 ggaagactgg ggcagcagtt ggggaagtgt ctgctga                           1577

<210> SEQ ID NO 2
<211> LENGTH: 499
<212> TYPE: PRT
<213> ORGANISM: Homo sapiens

<400> SEQUENCE: 2

Met Thr Leu Ile Leu Thr Ser Leu Leu Phe Phe Gly Leu Ser Leu Gly
    -15                 -10                  -5                -1

Pro Arg Thr Arg Val Gln Ala Glu Asn Leu Pro Lys Pro Ile Leu Trp
1                5                  10                  15

Ala Glu Pro Gly Pro Val Ile Thr Trp His Asn Pro Val Thr Ile Trp
                20                  25                  30

Cys Gln Gly Thr Leu Glu Ala Gln Gly Tyr Arg Leu Asp Lys Glu Gly
            35                  40                  45

Asn Ser Met Ser Arg His Ile Leu Lys Thr Leu Glu Ser Glu Asn Lys
        50                  55                  60

Val Lys Leu Ser Ile Pro Ser Met Met Trp Glu His Ala Gly Arg Tyr
65                  70                  75                  80

His Cys Tyr Tyr Gln Ser Pro Ala Gly Trp Ser Glu Pro Ser Asp Pro
                85                  90                  95

Leu Glu Leu Val Val Thr Ala Tyr Ser Arg Pro Thr Leu Ser Ala Leu
                100                 105                 110

Pro Ser Pro Val Val Thr Ser Gly Val Asn Val Thr Leu Arg Cys Ala
            115                 120                 125
```

```
Ser Arg Leu Gly Leu Gly Arg Phe Thr Leu Ile Glu Glu Gly Asp His
130                 135                 140

Arg Leu Ser Trp Thr Leu Asn Ser His Gln His Asn His Gly Lys Phe
145                 150                 155                 160

Gln Ala Leu Phe Pro Met Gly Pro Leu Thr Phe Ser Asn Arg Gly Thr
                165                 170                 175

Phe Arg Cys Tyr Gly Tyr Glu Asn Asn Thr Pro Tyr Val Trp Ser Glu
            180                 185                 190

Pro Ser Asp Pro Leu Gln Leu Leu Val Ser Gly Val Ser Arg Lys Pro
        195                 200                 205

Ser Leu Leu Thr Leu Gln Gly Pro Val Val Thr Pro Gly Glu Asn Leu
210                 215                 220

Thr Leu Gln Cys Gly Ser Asp Val Gly Tyr Ile Arg Tyr Thr Leu Tyr
225                 230                 235                 240

Lys Glu Gly Ala Asp Gly Leu Pro Gln Arg Pro Gly Arg Gln Pro Gln
                245                 250                 255

Ala Gly Leu Ser Gln Ala Asn Phe Thr Leu Ser Pro Val Ser Arg Ser
            260                 265                 270

Tyr Gly Gly Gln Tyr Arg Cys Tyr Gly Ala His Asn Val Ser Ser Glu
        275                 280                 285

Trp Ser Ala Pro Ser Asp Pro Leu Asp Ile Leu Ile Ala Gly Gln Ile
290                 295                 300

Ser Asp Arg Pro Ser Leu Ser Val Gln Pro Gly Pro Thr Val Thr Ser
305                 310                 315                 320

Gly Glu Lys Val Thr Leu Leu Cys Gln Ser Trp Asp Pro Met Phe Thr
                325                 330                 335

Phe Leu Leu Thr Lys Glu Gly Ala Ala His Pro Pro Leu Arg Leu Arg
            340                 345                 350

Ser Met Tyr Gly Ala His Lys Tyr Gln Ala Glu Phe Pro Met Ser Pro
        355                 360                 365

Val Thr Ser Ala His Ala Gly Thr Tyr Arg Cys Tyr Gly Ser Arg Ser
370                 375                 380

Ser Asn Pro Tyr Leu Leu Ser His Pro Ser Glu Pro Leu Glu Leu Val
385                 390                 395                 400

Val Ser Gly Ala Thr Glu Thr Leu Asn Pro Ala Gln Lys Lys Ser Asp
                405                 410                 415

Ser Lys Thr Ala Pro His Leu Gln Asp Tyr Thr Val Glu Asn Leu Ile
            420                 425                 430

Arg Met Gly Val Ala Gly Leu Val Leu Leu Phe Leu Gly Ile Leu Leu
        435                 440                 445

Phe Glu Ala Gln His Ser Gln Arg Ser Pro Pro Arg Cys Ser Gln Glu
450                 455                 460

Ala Asn Ser Arg Lys Asp Asn Ala Pro Phe Arg Val Val Glu Pro Trp
465                 470                 475                 480

Glu Gln Ile

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ctccaacccc tacctgctgt c                                              21
```

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ttcccaaggc tccaccactc t                                              21

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cctcaatcca gcacaaaaga agt                                            23

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cggatgagat tctccactgt gtaa                                           24

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ccacccatgg caaattcc                                                  18

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tgggatttcc attgatgaca ag                                             22

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cagggccagg aggaggagat g                                              21

```
<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tcagcagaca cttccccaac t                                                   21

<210> SEQ ID NO 11
<211> LENGTH: 105
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ccgctcgaga tgaccctcat tctcacaagc ctgctcttct ttgggctgag cctgggcgat         60
tacaaggatg acgacgataa gcccaggacc cgggtgcagg cagaa                        105

<210> SEQ ID NO 12
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ctagactagt tcagatctgt tcccaaggct c                                        31

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ccgctcgaga tgaccctcat tctcacaagc                                          30

<210> SEQ ID NO 14
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ctagactagt tcacttatcg tcgtcatcct tgtaatcgat ctgttcccaa ggctc              55

<210> SEQ ID NO 15
<211> LENGTH: 313
<212> TYPE: DNA
<213> ORGANISM: Homo sapiens
<220> FEATURE:
<221> NAME/KEY: CDS
<222> LOCATION: (7)..(264)

<400> SEQUENCE: 15 cccaag atg att cca gca gtg gtc ttg ctc tta ctc ctt ttg gtt gaa            48
       Met Ile Pro Ala Val Val Leu Leu Leu Leu Leu Leu Val Glu
       1               5                   10
```

```
caa gca gcg gcc ctg gga gag cct cag ctc tgc tat atc ctg gat gcc    96
Gln Ala Ala Ala Leu Gly Glu Pro Gln Leu Cys Tyr Ile Leu Asp Ala
 15                  20                  25                  30 atc ctg ttt ctg tat gga att gtc ctc acc ctc ctc tac tgt cga ctg   144
Ile Leu Phe Leu Tyr Gly Ile Val Leu Thr Leu Leu Tyr Cys Arg Leu
                 35                  40                  45 aag atc caa gtg cga aag gca gct ata acc agc tat gag aaa tca gat   192
Lys Ile Gln Val Arg Lys Ala Ala Ile Thr Ser Tyr Glu Lys Ser Asp
             50                  55                  60 ggt gtt tac acg ggc ctg agc acc agg aac cag gag act tac gag act   240
Gly Val Tyr Thr Gly Leu Ser Thr Arg Asn Gln Glu Thr Tyr Glu Thr
         65                  70                  75 ctg aag cat gag aaa cca cca cag tagctttaga atagatgcgg tcatattctt   294
Leu Lys His Glu Lys Pro Pro Gln
     80                  85 ctttggcttc tggttcttc                                               313

<210> SEQ ID NO 16
<211> LENGTH: 86
<212> TYPE: PRT
<213> ORGANISM: Homo sapiens

<400> SEQUENCE: 16

Met Ile Pro Ala Val Val Leu Leu Leu Leu Leu Val Glu Gln Ala
 1               5                  10                  15

Ala Ala Leu Gly Glu Pro Gln Leu Cys Tyr Ile Leu Asp Ala Ile Leu
             20                  25                  30

Phe Leu Tyr Gly Ile Val Leu Thr Leu Leu Tyr Cys Arg Leu Lys Ile
         35                  40                  45

Gln Val Arg Lys Ala Ala Ile Thr Ser Tyr Glu Lys Ser Asp Gly Val
     50                  55                  60

Tyr Thr Gly Leu Ser Thr Arg Asn Gln Glu Thr Tyr Glu Thr Leu Lys
 65                  70                  75                  80

His Glu Lys Pro Pro Gln
                 85

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cccaagatga ttccagcagt g                                             21

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ggaagaacca gaagccaaag a                                             21

<210> SEQ ID NO 19
<211> LENGTH: 30
<212> TYPE: DNA
<213> ORGANISM: Artificial Sequence
```

-continued

<220> FEATURE:
<223> OTHER INFORMATION: Description of Artificial Sequence: Synthetic
      primer

<400> SEQUENCE: 19
ccgctcgaga tgattccagc agtggtcttg                                        30

<210> SEQ ID NO 20
<211> LENGTH: 61
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ctagactagt ctacagatcc tcttcagaga tgagtttctg ctcctgtggt ggtttctcat       60
g                                                                      61

<210> SEQ ID NO 21
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Cys Ser Gln Glu Ala Asn Ser Arg Lys Asp Asn Ala Pro Phe Arg Val
1               5                   10                  15

Val Glu Pro Trp Glu Gln Ile
            20

<210> SEQ ID NO 22
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ccgctcgaga tgaccccccat cctcacggtc c                                     31

<210> SEQ ID NO 23
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ctagactagt tcacttatcg tcgtcatcct tgtaatccct cccggctgca tcttg            55

<210> SEQ ID NO 24
<211> LENGTH: 1425
<212> TYPE: DNA
<213> ORGANISM: Homo sapiens
<220> FEATURE:
<221> NAME/KEY: CDS
<222> LOCATION: (1)..(1422)

<400> SEQUENCE: 24 atg acc ccc atc ctc acg gtc ctg atc tgt ctc ggg ctg agt ctg ggc        48
Met Thr Pro Ile Leu Thr Val Leu Ile Cys Leu Gly Leu Ser Leu Gly
1               5                   10                  15

```
ccc agg acc cac gtg cag gca ggg cac ctc ccc aag ccc acc ctc tgg      96
Pro Arg Thr His Val Gln Ala Gly His Leu Pro Lys Pro Thr Leu Trp
        20                  25                  30 gct gag cca ggc tct gtg atc atc cag gga agt cct gtg acc ctc agg     144
Ala Glu Pro Gly Ser Val Ile Ile Gln Gly Ser Pro Val Thr Leu Arg
            35                  40                  45 tgt cag ggg agc ctt cag gct gag gag tac cat cta tat agg gaa aac     192
Cys Gln Gly Ser Leu Gln Ala Glu Glu Tyr His Leu Tyr Arg Glu Asn
 50                  55                  60 aaa tca gca tcc tgg gtt aga cgg ata caa gag cct ggg aag aat ggc     240
Lys Ser Ala Ser Trp Val Arg Arg Ile Gln Glu Pro Gly Lys Asn Gly
 65                  70                  75                  80 cag ttc ccc atc cca tcc atc acc tgg gaa cac gca ggg cgg tat cac     288
Gln Phe Pro Ile Pro Ser Ile Thr Trp Glu His Ala Gly Arg Tyr His
                85                  90                  95 tgt cag tac tac agc cac aat cac tca tca gag tac agt gac ccc ctg     336
Cys Gln Tyr Tyr Ser His Asn His Ser Ser Glu Tyr Ser Asp Pro Leu
            100                 105                 110 gag ctg gtg gtg aca gga gcc tac agc aaa ccc acc ctc tca gct ctg     384
Glu Leu Val Val Thr Gly Ala Tyr Ser Lys Pro Thr Leu Ser Ala Leu
        115                 120                 125 ccc agc cct gtg gtg acc tta gga ggg aac gtg acc ctc cag tgt gtc     432
Pro Ser Pro Val Val Thr Leu Gly Gly Asn Val Thr Leu Gln Cys Val
130                 135                 140 tca cag gtg gca ttt gac ggc ttc att ctg tgt aag gaa gga gaa gat     480
Ser Gln Val Ala Phe Asp Gly Phe Ile Leu Cys Lys Glu Gly Glu Asp
145                 150                 155                 160 gaa cac cca caa cgc ctg aac tcc cat tcc cat gcc cgt ggg tgg tcc     528
Glu His Pro Gln Arg Leu Asn Ser His Ser His Ala Arg Gly Trp Ser
                165                 170                 175 tgg gcc atc ttc tcc gtg ggc ccc gtg agc ccg agt cgc agg tgg tcg     576
Trp Ala Ile Phe Ser Val Gly Pro Val Ser Pro Ser Arg Arg Trp Ser
            180                 185                 190 tac agg tgc tat gct tat gac tcg aac tct ccc tat gtg tgg tct cta     624
Tyr Arg Cys Tyr Ala Tyr Asp Ser Asn Ser Pro Tyr Val Trp Ser Leu
        195                 200                 205 ccc agt gat ctc ctg gag ctc ctg gtc cca ggt gtt tct aag aag cca     672
Pro Ser Asp Leu Leu Glu Leu Leu Val Pro Gly Val Ser Lys Lys Pro
210                 215                 220 tca ctc tca gtg cag cca ggt cct atg gtg gcc cct ggg gag agc ctg     720
Ser Leu Ser Val Gln Pro Gly Pro Met Val Ala Pro Gly Glu Ser Leu
225                 230                 235                 240 acc ctc cag tgt gtc tct gat gtc ggc tac gac aga ttt gtt ctg tat     768
Thr Leu Gln Cys Val Ser Asp Val Gly Tyr Asp Arg Phe Val Leu Tyr
                245                 250                 255 aag gag gga gaa cgt gac ttc ctc cag cgc cct ggt tgg cag ccc cag     816
Lys Glu Gly Glu Arg Asp Phe Leu Gln Arg Pro Gly Trp Gln Pro Gln
            260                 265                 270 gct ggg ctc tcc cag gcc aac ttc acc ctg ggc cct gtg agc ccc tcc     864
Ala Gly Leu Ser Gln Ala Asn Phe Thr Leu Gly Pro Val Ser Pro Ser
        275                 280                 285 cac ggg ggc cag tac aga tgc tac agt gca cac aac ctc tcc tcc gag     912
His Gly Gly Gln Tyr Arg Cys Tyr Ser Ala His Asn Leu Ser Ser Glu
    290                 295                 300 tgg tcg gcc ccc agt gac ccc ctg gac atc ctg atc aca gga cag ttc     960
Trp Ser Ala Pro Ser Asp Pro Leu Asp Ile Leu Ile Thr Gly Gln Phe
305                 310                 315                 320 tat gac aga ccc tct ctc tcg gtg cag ccg gtc ccc aca gta gcc cca    1008
Tyr Asp Arg Pro Ser Leu Ser Val Gln Pro Val Pro Thr Val Ala Pro
                325                 330                 335
```

```
gga aag aac gtg acc ctg ctg tgt cag tca cgg ggg cag ttc cac act    1056
Gly Lys Asn Val Thr Leu Leu Cys Gln Ser Arg Gly Gln Phe His Thr
            340                 345                 350 ttc ctt ctg acc aag gag ggg gca ggc cat ccc cca ctg cat ctg aga    1104
Phe Leu Leu Thr Lys Glu Gly Ala Gly His Pro Pro Leu His Leu Arg
        355                 360                 365 tca gag cac caa gct cag cag aac cag gct gaa ttc cgc atg ggt cct    1152
Ser Glu His Gln Ala Gln Gln Asn Gln Ala Glu Phe Arg Met Gly Pro
    370                 375                 380 gtg acc tca gcc cac gtg ggg acc tac aga tgc tac agc tca ctc agc    1200
Val Thr Ser Ala His Val Gly Thr Tyr Arg Cys Tyr Ser Ser Leu Ser
385                 390                 395                 400 tcc aac ccc tac ctg ctg tct ctc ccc agt gac ccc ctg gag ctc gtg    1248
Ser Asn Pro Tyr Leu Leu Ser Leu Pro Ser Asp Pro Leu Glu Leu Val
                405                 410                 415 gtc tca gca tcc cta ggc caa cac ccc cag gat tac aca gtg gag aat    1296
Val Ser Ala Ser Leu Gly Gln His Pro Gln Asp Tyr Thr Val Glu Asn
            420                 425                 430 ctc atc cgc atg ggt gtg gct ggc ttg gtc ctg gtg gtc ctc ggg att    1344
Leu Ile Arg Met Gly Val Ala Gly Leu Val Leu Val Val Leu Gly Ile
        435                 440                 445 ctg cta ttt gag gct cag cac agc cag aga agc cta caa gat gca gcc    1392
Leu Leu Phe Glu Ala Gln His Ser Gln Arg Ser Leu Gln Asp Ala Ala
    450                 455                 460 ggg agg gat tac aag gat gac gac gat aag tga                        1425
Gly Arg Asp Tyr Lys Asp Asp Asp Asp Lys
465                 470

<210> SEQ ID NO 25
<211> LENGTH: 474
<212> TYPE: PRT
<213> ORGANISM: Homo sapiens

<400> SEQUENCE: 25

Met Thr Pro Ile Leu Thr Val Leu Ile Cys Leu Gly Leu Ser Leu Gly
1               5                   10                  15

Pro Arg Thr His Val Gln Ala Gly His Leu Pro Lys Pro Thr Leu Trp
            20                  25                  30

Ala Glu Pro Gly Ser Val Ile Ile Gln Gly Ser Pro Val Thr Leu Arg
        35                  40                  45

Cys Gln Gly Ser Leu Gln Ala Glu Glu Tyr His Leu Tyr Arg Glu Asn
    50                  55                  60

Lys Ser Ala Ser Trp Val Arg Arg Ile Gln Glu Pro Gly Lys Asn Gly
65                  70                  75                  80

Gln Phe Pro Ile Pro Ser Ile Thr Trp Glu His Ala Gly Arg Tyr His
                85                  90                  95

Cys Gln Tyr Tyr Ser His Asn His Ser Ser Glu Tyr Ser Asp Pro Leu
            100                 105                 110

Glu Leu Val Val Thr Gly Ala Tyr Ser Lys Pro Thr Leu Ser Ala Leu
        115                 120                 125

Pro Ser Pro Val Val Thr Leu Gly Gly Asn Val Thr Leu Gln Cys Val
    130                 135                 140

Ser Gln Val Ala Phe Asp Gly Phe Ile Leu Cys Lys Glu Gly Glu Asp
145                 150                 155                 160

Glu His Pro Gln Arg Leu Asn Ser His Ser His Ala Arg Gly Trp Ser
                165                 170                 175

Trp Ala Ile Phe Ser Val Gly Pro Val Ser Pro Ser Arg Arg Trp Ser
            180                 185                 190
```

-continued

```
Tyr Arg Cys Tyr Ala Tyr Asp Ser Asn Ser Pro Tyr Val Trp Ser Leu
            195                 200                 205

Pro Ser Asp Leu Leu Glu Leu Val Pro Gly Val Ser Lys Lys Pro
210                 215                 220

Ser Leu Ser Val Gln Pro Gly Pro Met Val Ala Pro Gly Glu Ser Leu
225                 230                 235                 240

Thr Leu Gln Cys Val Ser Asp Val Gly Tyr Asp Arg Phe Val Leu Tyr
                245                 250                 255

Lys Glu Gly Glu Arg Asp Phe Leu Gln Arg Pro Gly Trp Gln Pro Gln
            260                 265                 270

Ala Gly Leu Ser Gln Ala Asn Phe Thr Leu Gly Pro Val Ser Pro Ser
        275                 280                 285

His Gly Gly Gln Tyr Arg Cys Tyr Ser Ala His Asn Leu Ser Ser Glu
    290                 295                 300

Trp Ser Ala Pro Ser Asp Pro Leu Asp Ile Leu Ile Thr Gly Gln Phe
305                 310                 315                 320

Tyr Asp Arg Pro Ser Leu Ser Val Gln Pro Val Pro Thr Val Ala Pro
                325                 330                 335

Gly Lys Asn Val Thr Leu Leu Cys Gln Ser Arg Gly Gln Phe His Thr
            340                 345                 350

Phe Leu Leu Thr Lys Glu Gly Ala Gly His Pro Pro Leu His Leu Arg
        355                 360                 365

Ser Glu His Gln Ala Gln Gln Asn Gln Ala Glu Phe Arg Met Gly Pro
    370                 375                 380

Val Thr Ser Ala His Val Gly Thr Tyr Arg Cys Tyr Ser Ser Leu Ser
385                 390                 395                 400

Ser Asn Pro Tyr Leu Leu Ser Leu Pro Ser Asp Pro Leu Glu Leu Val
                405                 410                 415

Val Ser Ala Ser Leu Gly Gln His Pro Gln Asp Tyr Thr Val Glu Asn
            420                 425                 430

Leu Ile Arg Met Gly Val Ala Gly Leu Val Leu Val Val Leu Gly Ile
        435                 440                 445

Leu Leu Phe Glu Ala Gln His Ser Gln Arg Ser Leu Gln Asp Ala Ala
    450                 455                 460

Gly Arg Asp Tyr Lys Asp Asp Asp Lys
465                 470

<210> SEQ ID NO 26
<211> LENGTH: 1953
<212> TYPE: DNA
<213> ORGANISM: Homo sapiens
<220> FEATURE:
<221> NAME/KEY: CDS
<222> LOCATION: (1)..(1950)

<400> SEQUENCE: 26 atg acc ccc atc ctc acg gtc ctg atc tgt ctc ggg ctg agt ctg ggc      48
Met Thr Pro Ile Leu Thr Val Leu Ile Cys Leu Gly Leu Ser Leu Gly
1               5                   10                  15 ccc cgg acc cac gtg cag gca ggg cac ctc ccc aag ccc acc ctc tgg      96
Pro Arg Thr His Val Gln Ala Gly His Leu Pro Lys Pro Thr Leu Trp
                20                  25                  30 gct gaa cca ggc tct gtg atc acc cag ggg agt cct gtg acc ctc agg     144
Ala Glu Pro Gly Ser Val Ile Thr Gln Gly Ser Pro Val Thr Leu Arg
            35                  40                  45 tgt cag ggg ggc cag gag acc cag gag tac cgt cta tat aga gaa aag     192
Cys Gln Gly Gly Gln Glu Thr Gln Glu Tyr Arg Leu Tyr Arg Glu Lys
        50                  55                  60
```

| | | |
|---|---|---|
| aaa aca gca ccc tgg att aca cgg atc cca cag gag ctt gtg aag aag<br>Lys Thr Ala Pro Trp Ile Thr Arg Ile Pro Gln Glu Leu Val Lys Lys<br>65                          70                          75                          80 | | 240 |
| ggc cag ttc ccc atc cca tcc atc acc tgg gaa cat gca ggg cgg tat<br>Gly Gln Phe Pro Ile Pro Ser Ile Thr Trp Glu His Ala Gly Arg Tyr<br>                        85                          90                          95 | | 288 |
| cgc tgt tac tat ggt agc gac act gca ggc cgc tca gag agc agt gac<br>Arg Cys Tyr Tyr Gly Ser Asp Thr Ala Gly Arg Ser Glu Ser Ser Asp<br>                       100                        105                       110 | | 336 |
| ccc ctg gag ctg gtg gtg aca gga gcc tac atc aaa ccc acc ctc tca<br>Pro Leu Glu Leu Val Val Thr Gly Ala Tyr Ile Lys Pro Thr Leu Ser<br>             115                        120                       125 | | 384 |
| gcc cag ccc agc ccc gtg gtg aac tca gga ggg aat gta acc ctc cag<br>Ala Gln Pro Ser Pro Val Val Asn Ser Gly Gly Asn Val Thr Leu Gln<br>130                          135                          140 | | 432 |
| tgt gac tca cag gtg gca ttt gat ggc ttc att ctg tgt aag gaa gga<br>Cys Asp Ser Gln Val Ala Phe Asp Gly Phe Ile Leu Cys Lys Glu Gly<br>145                          150                          155                       160 | | 480 |
| gaa gat gaa cac cca caa tgc ctg aac tcc cag ccc cat gcc cgt ggg<br>Glu Asp Glu His Pro Gln Cys Leu Asn Ser Gln Pro His Ala Arg Gly<br>                       165                        170                       175 | | 528 |
| tcg tcc cgc gcc atc ttc tcc gtg ggc ccc gtg agc ccg agt cgc agg<br>Ser Ser Arg Ala Ile Phe Ser Val Gly Pro Val Ser Pro Ser Arg Arg<br>                       180                        185                       190 | | 576 |
| tgg tgg tac agg tgc tat gct tat gac tcg aac tct ccc tat gag tgg<br>Trp Trp Tyr Arg Cys Tyr Ala Tyr Asp Ser Asn Ser Pro Tyr Glu Trp<br>                   195                        200                       205 | | 624 |
| tct cta ccc agt gat ctc ctg gag ctc ctg gtc cta ggt gtt tct aag<br>Ser Leu Pro Ser Asp Leu Leu Glu Leu Leu Val Leu Gly Val Ser Lys<br>210                          215                          220 | | 672 |
| aag cca tca ctc tca gtg cag cca ggt cct atc gtg gcc cct gag gag<br>Lys Pro Ser Leu Ser Val Gln Pro Gly Pro Ile Val Ala Pro Glu Glu<br>225                          230                          235                       240 | | 720 |
| acc ctg act ctg cag tgt ggc tct gat gct ggc tac aac aga ttt gtt<br>Thr Leu Thr Leu Gln Cys Gly Ser Asp Ala Gly Tyr Asn Arg Phe Val<br>                       245                        250                       255 | | 768 |
| ctg tat aag gac ggg gaa cgt gac ttc ctt cag ctc gct ggc gca cag<br>Leu Tyr Lys Asp Gly Glu Arg Asp Phe Leu Gln Leu Ala Gly Ala Gln<br>             260                        265                       270 | | 816 |
| ccc cag gct ggg ctc tcc cag gcc aac ttc acc ctg ggc cct gtg agc<br>Pro Gln Ala Gly Leu Ser Gln Ala Asn Phe Thr Leu Gly Pro Val Ser<br>             275                        280                       285 | | 864 |
| cgc tcc tac ggg ggc cag tac aga tgc tac ggt gca cac aac ctc tcc<br>Arg Ser Tyr Gly Gly Gln Tyr Arg Cys Tyr Gly Ala His Asn Leu Ser<br>                       290                        295                       300 | | 912 |
| tcc gag tgg tcg gcc ccc agc gac ccc ctg gac atc ctg atc gca gga<br>Ser Glu Trp Ser Ala Pro Ser Asp Pro Leu Asp Ile Leu Ile Ala Gly<br>305                          310                          315                       320 | | 960 |
| cag ttc tat gac aga gtc tcc ctc tcg gtg cag ccg ggc ccc acg gtg<br>Gln Phe Tyr Asp Arg Val Ser Leu Ser Val Gln Pro Gly Pro Thr Val<br>                       325                        330                       335 | | 1008 |
| gcc tca gga gag aac gtg acc ctg ctg tgt cag tca cag gga tgg atg<br>Ala Ser Gly Glu Asn Val Thr Leu Leu Cys Gln Ser Gln Gly Trp Met<br>             340                        345                       350 | | 1056 |
| caa act ttc ctt ctg acc aag gag ggg gca gct gat gac cca tgg cgt<br>Gln Thr Phe Leu Leu Thr Lys Glu Gly Ala Ala Asp Asp Pro Trp Arg<br>             355                        360                       365 | | 1104 |
| cta aga tca acg tac caa tct caa aaa tac cag gct gaa ttc ccc atg<br>Leu Arg Ser Thr Tyr Gln Ser Gln Lys Tyr Gln Ala Glu Phe Pro Met<br>370                          375                          380 | | 1152 |

| | | | | | | | | | | | | | | | | |
|---|---|---|---|---|---|---|---|---|---|---|---|---|---|---|---|---|
| ggt | cct | gtg | acc | tca | gcc | cat | gcg | ggg | acc | tac | agg | tgc | tac | ggc | tca | 1200 |
| Gly | Pro | Val | Thr | Ser | Ala | His | Ala | Gly | Thr | Tyr | Arg | Cys | Tyr | Gly | Ser | |
| 385 | | | | 390 | | | | | 395 | | | | | 400 | | |

| cag | agc | tcc | aaa | ccc | tac | ctg | ctg | act | cac | ccc | agt | gac | ccc | ctg | gag | 1248 |
|---|---|---|---|---|---|---|---|---|---|---|---|---|---|---|---|---|
| Gln | Ser | Ser | Lys | Pro | Tyr | Leu | Leu | Thr | His | Pro | Ser | Asp | Pro | Leu | Glu | |
| | | | | 405 | | | | | 410 | | | | | 415 | | |

| ctc | gtg | gtc | tca | gga | ccg | tct | ggg | ggc | ccc | agc | tcc | ccg | aca | aca | ggc | 1296 |
|---|---|---|---|---|---|---|---|---|---|---|---|---|---|---|---|---|
| Leu | Val | Val | Ser | Gly | Pro | Ser | Gly | Gly | Pro | Ser | Ser | Pro | Thr | Thr | Gly | |
| | 420 | | | | | 425 | | | | | 430 | | | | | |

| ccc | acc | tcc | aca | tct | ggc | cct | gag | gac | cag | ccc | ctc | acc | ccc | acc | ggg | 1344 |
|---|---|---|---|---|---|---|---|---|---|---|---|---|---|---|---|---|
| Pro | Thr | Ser | Thr | Ser | Gly | Pro | Glu | Asp | Gln | Pro | Leu | Thr | Pro | Thr | Gly | |
| | | 435 | | | | | 440 | | | | | 445 | | | | |

| tcg | gat | ccc | cag | agt | ggt | ctg | gga | agg | cac | ctg | ggg | gtt | gtg | atc | ggc | 1392 |
|---|---|---|---|---|---|---|---|---|---|---|---|---|---|---|---|---|
| Ser | Asp | Pro | Gln | Ser | Gly | Leu | Gly | Arg | His | Leu | Gly | Val | Val | Ile | Gly | |
| 450 | | | | | 455 | | | | | 460 | | | | | | |

| atc | ttg | gtg | gcc | gtc | atc | cta | ctg | ctc | ctc | ctc | ctc | ctc | ctc | ctc | ttc | 1440 |
|---|---|---|---|---|---|---|---|---|---|---|---|---|---|---|---|---|
| Ile | Leu | Val | Ala | Val | Ile | Leu | Leu | Leu | Leu | Leu | Leu | Leu | Leu | Leu | Phe | |
| 465 | | | | | 470 | | | | | 475 | | | | | 480 | |

| ctc | atc | ctc | cga | cat | cga | cgt | cag | ggc | aaa | cac | tgg | aca | tcg | acc | cag | 1488 |
|---|---|---|---|---|---|---|---|---|---|---|---|---|---|---|---|---|
| Leu | Ile | Leu | Arg | His | Arg | Arg | Gln | Gly | Lys | His | Trp | Thr | Ser | Thr | Gln | |
| | | | | 485 | | | | | 490 | | | | | 495 | | |

| aga | aag | gct | gat | ttc | caa | cat | cct | gca | ggg | gct | gtg | ggg | cca | gag | ccc | 1536 |
|---|---|---|---|---|---|---|---|---|---|---|---|---|---|---|---|---|
| Arg | Lys | Ala | Asp | Phe | Gln | His | Pro | Ala | Gly | Ala | Val | Gly | Pro | Glu | Pro | |
| | | | 500 | | | | | 505 | | | | | 510 | | | |

| aca | gac | aga | ggc | ctg | cag | tgg | agg | tcc | agc | cca | gct | gcc | gat | gcc | cag | 1584 |
|---|---|---|---|---|---|---|---|---|---|---|---|---|---|---|---|---|
| Thr | Asp | Arg | Gly | Leu | Gln | Trp | Arg | Ser | Ser | Pro | Ala | Ala | Asp | Ala | Gln | |
| | | | 515 | | | | | 520 | | | | | 525 | | | |

| gaa | gaa | aac | ctc | tat | gct | gcc | gtg | aag | cac | aca | cag | cct | gag | gat | ggg | 1632 |
|---|---|---|---|---|---|---|---|---|---|---|---|---|---|---|---|---|
| Glu | Glu | Asn | Leu | Tyr | Ala | Ala | Val | Lys | His | Thr | Gln | Pro | Glu | Asp | Gly | |
| 530 | | | | | 535 | | | | | 540 | | | | | | |

| gtg | gag | atg | gac | act | cgg | agc | cca | cac | gat | gaa | gac | ccc | cag | gca | gtg | 1680 |
|---|---|---|---|---|---|---|---|---|---|---|---|---|---|---|---|---|
| Val | Glu | Met | Asp | Thr | Arg | Ser | Pro | His | Asp | Glu | Asp | Pro | Gln | Ala | Val | |
| 545 | | | | | 550 | | | | | 555 | | | | | 560 | |

| acg | tat | gcc | gag | gtg | aaa | cac | tcc | aga | cct | agg | aga | gaa | atg | gcc | tct | 1728 |
|---|---|---|---|---|---|---|---|---|---|---|---|---|---|---|---|---|
| Thr | Tyr | Ala | Glu | Val | Lys | His | Ser | Arg | Pro | Arg | Arg | Glu | Met | Ala | Ser | |
| | | | | 565 | | | | | 570 | | | | | 575 | | |

| cct | cct | tcc | cca | ctg | tct | ggg | gaa | ttc | ctg | gac | aca | aag | gac | aga | cag | 1776 |
|---|---|---|---|---|---|---|---|---|---|---|---|---|---|---|---|---|
| Pro | Pro | Ser | Pro | Leu | Ser | Gly | Glu | Phe | Leu | Asp | Thr | Lys | Asp | Arg | Gln | |
| | | | 580 | | | | | 585 | | | | | 590 | | | |

| gcg | gaa | gag | gac | agg | cag | atg | gac | act | gag | gct | gct | gca | tct | gaa | gcc | 1824 |
|---|---|---|---|---|---|---|---|---|---|---|---|---|---|---|---|---|
| Ala | Glu | Glu | Asp | Arg | Gln | Met | Asp | Thr | Glu | Ala | Ala | Ala | Ser | Glu | Ala | |
| | | | 595 | | | | | 600 | | | | | 605 | | | |

| ccc | cag | gat | gtg | acc | tac | gcc | cag | ctg | cac | agc | ttg | acc | ctt | aga | cgg | 1872 |
|---|---|---|---|---|---|---|---|---|---|---|---|---|---|---|---|---|
| Pro | Gln | Asp | Val | Thr | Tyr | Ala | Gln | Leu | His | Ser | Leu | Thr | Leu | Arg | Arg | |
| | 610 | | | | | 615 | | | | | 620 | | | | | |

| aag | gca | act | gag | cct | cct | cca | tcc | cag | gaa | ggg | ccc | tct | cca | gct | gtg | 1920 |
|---|---|---|---|---|---|---|---|---|---|---|---|---|---|---|---|---|
| Lys | Ala | Thr | Glu | Pro | Pro | Pro | Ser | Gln | Glu | Gly | Pro | Ser | Pro | Ala | Val | |
| 625 | | | | | 630 | | | | | 635 | | | | | 640 | |

| ccc | agc | atc | tac | gcc | act | ctg | gcc | atc | cac | tag | | | | | | 1953 |
|---|---|---|---|---|---|---|---|---|---|---|---|---|---|---|---|---|
| Pro | Ser | Ile | Tyr | Ala | Thr | Leu | Ala | Ile | His | | | | | | | |
| | | | | 645 | | | | | 650 | | | | | | | |

<210> SEQ ID NO 27
<211> LENGTH: 650
<212> TYPE: PRT
<213> ORGANISM: Homo sapiens

```
<400> SEQUENCE: 27

Met Thr Pro Ile Leu Thr Val Leu Ile Cys Leu Gly Leu Ser Leu Gly
1               5                   10                  15

Pro Arg Thr His Val Gln Ala Gly His Leu Pro Lys Pro Thr Leu Trp
            20                  25                  30

Ala Glu Pro Gly Ser Val Ile Thr Gln Gly Ser Pro Val Thr Leu Arg
        35                  40                  45

Cys Gln Gly Gly Gln Glu Thr Gln Glu Tyr Arg Leu Tyr Arg Glu Lys
    50                  55                  60

Lys Thr Ala Pro Trp Ile Thr Arg Ile Pro Gln Glu Leu Val Lys Lys
65                  70                  75                  80

Gly Gln Phe Pro Ile Pro Ser Ile Thr Trp Glu His Ala Gly Arg Tyr
                85                  90                  95

Arg Cys Tyr Tyr Gly Ser Asp Thr Ala Gly Arg Ser Glu Ser Ser Asp
            100                 105                 110

Pro Leu Glu Leu Val Val Thr Gly Ala Tyr Ile Lys Pro Thr Leu Ser
        115                 120                 125

Ala Gln Pro Ser Pro Val Asn Ser Gly Gly Asn Val Thr Leu Gln
130                 135                 140

Cys Asp Ser Gln Val Ala Phe Asp Gly Phe Ile Leu Cys Lys Glu Gly
145                 150                 155                 160

Glu Asp Glu His Pro Gln Cys Leu Asn Ser Gln Pro His Ala Arg Gly
                165                 170                 175

Ser Ser Arg Ala Ile Phe Ser Val Gly Pro Val Ser Pro Ser Arg Arg
            180                 185                 190

Trp Trp Tyr Arg Cys Tyr Ala Tyr Asp Ser Asn Ser Pro Tyr Glu Trp
        195                 200                 205

Ser Leu Pro Ser Asp Leu Leu Glu Leu Leu Val Leu Gly Val Ser Lys
210                 215                 220

Lys Pro Ser Leu Ser Val Gln Pro Gly Pro Ile Val Ala Pro Glu Glu
225                 230                 235                 240

Thr Leu Thr Leu Gln Cys Gly Ser Asp Ala Gly Tyr Asn Arg Phe Val
                245                 250                 255

Leu Tyr Lys Asp Gly Glu Arg Asp Phe Leu Gln Leu Ala Gly Ala Gln
            260                 265                 270

Pro Gln Ala Gly Leu Ser Gln Ala Asn Phe Thr Leu Gly Pro Val Ser
        275                 280                 285

Arg Ser Tyr Gly Gly Gln Tyr Arg Cys Tyr Gly Ala His Asn Leu Ser
290                 295                 300

Ser Glu Trp Ser Ala Pro Ser Asp Pro Leu Asp Ile Leu Ile Ala Gly
305                 310                 315                 320

Gln Phe Tyr Asp Arg Val Ser Leu Ser Val Gln Pro Gly Pro Thr Val
                325                 330                 335

Ala Ser Gly Glu Asn Val Thr Leu Leu Cys Gln Ser Gln Gly Trp Met
            340                 345                 350

Gln Thr Phe Leu Leu Thr Lys Glu Gly Ala Ala Asp Asp Pro Trp Arg
        355                 360                 365

Leu Arg Ser Thr Tyr Gln Ser Gln Lys Tyr Gln Ala Glu Phe Pro Met
370                 375                 380

Gly Pro Val Thr Ser Ala His Ala Gly Thr Tyr Arg Cys Tyr Gly Ser
385                 390                 395                 400

Gln Ser Ser Lys Pro Tyr Leu Leu Thr His Pro Ser Asp Pro Leu Glu
                405                 410                 415
```

```
Leu Val Val Ser Gly Pro Ser Gly Pro Ser Ser Pro Thr Thr Gly
            420             425             430

Pro Thr Ser Thr Ser Gly Pro Glu Asp Gln Pro Leu Thr Pro Thr Gly
                435             440             445

Ser Asp Pro Gln Ser Gly Leu Gly Arg His Leu Gly Val Val Ile Gly
450             455             460

Ile Leu Val Ala Val Ile Leu Leu Leu Leu Leu Leu Leu Leu Leu Phe
465             470             475             480

Leu Ile Leu Arg His Arg Arg Gln Gly Lys His Trp Thr Ser Thr Gln
            485             490             495

Arg Lys Ala Asp Phe Gln His Pro Ala Gly Ala Val Gly Pro Glu Pro
            500             505             510

Thr Asp Arg Gly Leu Gln Trp Arg Ser Ser Pro Ala Ala Asp Ala Gln
            515             520             525

Glu Glu Asn Leu Tyr Ala Ala Val Lys His Thr Gln Pro Glu Asp Gly
            530             535             540

Val Glu Met Asp Thr Arg Ser Pro His Asp Glu Asp Pro Gln Ala Val
545             550             555             560

Thr Tyr Ala Glu Val Lys His Ser Arg Pro Arg Arg Glu Met Ala Ser
            565             570             575

Pro Pro Ser Pro Leu Ser Gly Glu Phe Leu Asp Thr Lys Asp Arg Gln
            580             585             590

Ala Glu Glu Asp Arg Gln Met Asp Thr Glu Ala Ala Ser Glu Ala
            595             600             605

Pro Gln Asp Val Thr Tyr Ala Gln Leu His Ser Leu Thr Leu Arg Arg
            610             615             620

Lys Ala Thr Glu Pro Pro Pro Ser Gln Glu Gly Pro Ser Pro Ala Val
625             630             635             640

Pro Ser Ile Tyr Ala Thr Leu Ala Ile His
            645             650

<210> SEQ ID NO 28
<211> LENGTH: 1347
<212> TYPE: DNA
<213> ORGANISM: Homo sapiens
<220> FEATURE:
<221> NAME/KEY: CDS
<222> LOCATION: (1)..(1344)

<400> SEQUENCE: 28 atg atc ccc acc ttc acg gct ctg ctc tgc ctc ggg ctg agt ctg ggc      48
Met Ile Pro Thr Phe Thr Ala Leu Leu Cys Leu Gly Leu Ser Leu Gly
1               5                   10                  15 ccc agg acc gac atg cag gca ggg ccc ctc ccc aaa ccc acc ctc tgg      96
Pro Arg Thr Asp Met Gln Ala Gly Pro Leu Pro Lys Pro Thr Leu Trp
                20                  25                  30 gct gag cca ggc tct gtg atc agc tgg ggg aac tct gtg acc atc tgg     144
Ala Glu Pro Gly Ser Val Ile Ser Trp Gly Asn Ser Val Thr Ile Trp
            35                  40                  45 tgt cag ggg acc ctg gag gct cgg gag tac cgt ctg gat aaa gag gaa     192
Cys Gln Gly Thr Leu Glu Ala Arg Glu Tyr Arg Leu Asp Lys Glu Glu
        50                  55                  60 agc cca gca ccc tgg gac aga cag aac cca ctg gag ccc aag aac aag     240
Ser Pro Ala Pro Trp Asp Arg Gln Asn Pro Leu Glu Pro Lys Asn Lys
65                  70                  75                  80 gcc aga ttc tcc atc cca tcc atg aca gag gac tat gca ggg aga tac     288
Ala Arg Phe Ser Ile Pro Ser Met Thr Glu Asp Tyr Ala Gly Arg Tyr
                85                  90                  95
```

| | | | | | | | | | | | | | | | | |
|---|---|---|---|---|---|---|---|---|---|---|---|---|---|---|---|---|
| cgc | tgt | tac | tat | cgc | agc | cct | gta | ggc | tgg | tca | cag | ccc | agt | gac | ccc | 336 |
| Arg | Cys | Tyr 100 | Tyr | Arg | Ser | Pro | Val 105 | Gly | Trp | Ser | Gln | Pro 110 | Ser | Asp | Pro | |
| ctg | gag | ctg | gtg | atg | aca | gga | gcc | tac | agt | aaa | ccc | acc | ctt | tca | gcc | 384 |
| Leu | Glu | Leu 115 | Val | Met | Thr | Gly | Ala 120 | Tyr | Ser | Lys | Pro | Thr 125 | Leu | Ser | Ala | |
| ctg | ccg | agt | cct | ctt | gtg | acc | tca | gga | aag | agc | gtg | acc | ctg | ctg | tgt | 432 |
| Leu | Pro | Ser 130 | Pro | Leu | Val | Thr | Ser 135 | Gly | Lys | Ser | Val | Thr 140 | Leu | Leu | Cys | |
| cag | tca | cgg | agc | cca | atg | gac | act | ttc | ctt | ctg | atc | aag | gag | cgg | gca | 480 |
| Gln 145 | Ser | Arg | Ser | Pro | Met 150 | Asp | Thr | Phe | Leu | Leu 155 | Ile | Lys | Glu | Arg | Ala 160 | |
| gcc | cat | ccc | cta | ctg | cat | ctg | aga | tca | gag | cac | gga | gct | cag | cag | cac | 528 |
| Ala | His | Pro | Leu | Leu 165 | His | Leu | Arg | Ser | Glu 170 | His | Gly | Ala | Gln | Gln 175 | His | |
| cag | gct | gaa | ttc | ccc | atg | agt | cct | gtg | acc | tca | gtg | cac | ggg | ggg | acc | 576 |
| Gln | Ala | Glu | Phe 180 | Pro | Met | Ser | Pro | Val 185 | Thr | Ser | Val | His | Gly 190 | Gly | Thr | |
| tac | agg | tgc | ttc | agc | tca | cac | ggc | ttc | tcc | cac | tac | ctg | ctg | tca | cac | 624 |
| Tyr | Arg | Cys 195 | Phe | Ser | Ser | His | Gly 200 | Phe | Ser | His | Tyr | Leu 205 | Leu | Ser | His | |
| ccc | agt | gac | ccc | ctg | gag | ctc | ata | gtc | tca | gga | tcc | ttg | gag | ggt | ccc | 672 |
| Pro | Ser | Asp 210 | Pro | Leu | Glu | Leu | Ile 215 | Val | Ser | Gly | Ser | Leu 220 | Glu | Gly | Pro | |
| agg | ccc | tca | ccc | aca | agg | tcc | gtc | tca | aca | gct | gca | ggc | cct | gag | gac | 720 |
| Arg 225 | Pro | Ser | Pro | Thr | Arg 230 | Ser | Val | Ser | Thr | Ala 235 | Ala | Gly | Pro | Glu | Asp 240 | |
| cag | ccc | ctc | atg | cct | aca | ggg | tca | gtc | ccc | cac | agt | ggt | ctg | aga | agg | 768 |
| Gln | Pro | Leu | Met | Pro 245 | Thr | Gly | Ser | Val | Pro 250 | His | Ser | Gly | Leu | Arg 255 | Arg | |
| cac | tgg | gag | gta | ctg | atc | ggg | gtc | ttg | gtg | gtc | tcc | atc | ctg | ctt | ctc | 816 |
| His | Trp | Glu | Val | Leu 260 | Ile | Gly | Val | Leu | Val 265 | Val | Ser | Ile | Leu | Leu 270 | Leu | |
| tcc | ctc | ctc | ctc | ttc | ctc | ctc | caa | cac | tgg | cgt | cag | gga | aaa | cac | | 864 |
| Ser | Leu | Leu | Leu | Phe 275 | Leu | Leu | Gln | His | Trp 280 | Arg | Gln | Gly | Lys | His 285 | | |
| agg | aca | ttg | gcc | cag | aga | cag | gct | gat | ttc | caa | cgt | cct | cca | ggg | gct | 912 |
| Arg | Thr | Leu | Ala | Gln 290 | Arg | Gln | Ala | Asp | Phe 295 | Gln | Arg | Pro | Pro | Gly 300 | Ala | |
| gcc | gag | cca | gag | ccc | aag | gac | ggg | ggc | cta | cag | agg | agg | tcc | agc | cca | 960 |
| Ala 305 | Glu | Pro | Glu | Pro | Lys 310 | Asp | Gly | Gly | Leu | Gln 315 | Arg | Arg | Ser | Ser | Pro 320 | |
| gct | gct | gac | gtc | cag | gga | gaa | aac | ttc | tgt | gct | gcc | gtg | aag | aac | aca | 1008 |
| Ala | Ala | Asp | Val | Gln 325 | Gly | Glu | Asn | Phe | Cys 330 | Ala | Ala | Val | Lys | Asn 335 | Thr | |
| cag | cct | gag | gac | ggg | gtg | gaa | atg | gac | act | cgg | cag | agc | cca | cac | gat | 1056 |
| Gln | Pro | Glu | Asp | Gly 340 | Val | Glu | Met | Asp | Thr 345 | Arg | Gln | Ser | Pro | His 350 | Asp | |
| gaa | gac | ccc | cag | gca | gtg | acg | tat | gcc | aag | gtg | aaa | cac | tcc | aga | cct | 1104 |
| Glu | Asp | Pro | Gln | Ala 355 | Val | Thr | Tyr | Ala | Lys 360 | Val | Lys | His | Ser | Arg 365 | Pro | |
| agg | aga | gaa | atg | gcc | tct | cct | ccc | tcc | cca | ctg | tct | ggg | gaa | ttc | ctg | 1152 |
| Arg | Arg | Glu | Met | Ala 370 | Ser | Pro | Pro | Ser | Pro 375 | Leu | Ser | Gly | Glu | Phe 380 | Leu | |
| gac | aca | aag | gac | aga | cag | gca | gaa | gag | gac | aga | cag | atg | gac | act | gag | 1200 |
| Asp 385 | Thr | Lys | Asp | Arg | Gln 390 | Ala | Glu | Glu | Asp | Arg 395 | Gln | Met | Asp | Thr | Glu 400 | |
| gct | gct | gca | tct | gaa | gcc | ccc | cag | gat | gtg | acc | tac | gcc | cgg | ctg | cac | 1248 |
| Ala | Ala | Ala | Ser | Glu 405 | Ala | Pro | Gln | Asp | Val 410 | Thr | Tyr | Ala | Arg | Leu 415 | His | |

```
agc ttt acc ctc aga cag aag gca act gag cct cct cca tcc cag gaa      1296
Ser Phe Thr Leu Arg Gln Lys Ala Thr Glu Pro Pro Pro Ser Gln Glu
            420                 425                 430 ggg gcc tct cca gct gag ccc agt gtc tat gcc act ctg gcc atc cac      1344
Gly Ala Ser Pro Ala Glu Pro Ser Val Tyr Ala Thr Leu Ala Ile His
            435                 440                 445 taa                                                                   1347

<210> SEQ ID NO 29
<211> LENGTH: 448
<212> TYPE: PRT
<213> ORGANISM: Homo sapiens

<400> SEQUENCE: 29

Met Ile Pro Thr Phe Thr Ala Leu Leu Cys Leu Gly Leu Ser Leu Gly
1               5                   10                  15

Pro Arg Thr Asp Met Gln Ala Gly Pro Leu Pro Lys Pro Thr Leu Trp
            20                  25                  30

Ala Glu Pro Gly Ser Val Ile Ser Trp Gly Asn Ser Val Thr Ile Trp
        35                  40                  45

Cys Gln Gly Thr Leu Glu Ala Arg Glu Tyr Arg Leu Asp Lys Glu Glu
    50                  55                  60

Ser Pro Ala Pro Trp Asp Arg Gln Asn Pro Leu Glu Pro Lys Asn Lys
65                  70                  75                  80

Ala Arg Phe Ser Ile Pro Ser Met Thr Glu Asp Tyr Ala Gly Arg Tyr
                85                  90                  95

Arg Cys Tyr Tyr Arg Ser Pro Val Gly Trp Ser Gln Pro Ser Asp Pro
            100                 105                 110

Leu Glu Leu Val Met Thr Gly Ala Tyr Ser Lys Pro Thr Leu Ser Ala
        115                 120                 125

Leu Pro Ser Pro Leu Val Thr Ser Gly Lys Ser Val Thr Leu Leu Cys
    130                 135                 140

Gln Ser Arg Ser Pro Met Asp Thr Phe Leu Leu Ile Lys Glu Arg Ala
145                 150                 155                 160

Ala His Pro Leu Leu His Leu Arg Ser Glu His Gly Ala Gln Gln His
                165                 170                 175

Gln Ala Glu Phe Pro Met Ser Pro Val Thr Ser Val His Gly Gly Thr
            180                 185                 190

Tyr Arg Cys Phe Ser Ser His Gly Phe Ser His Tyr Leu Leu Ser His
        195                 200                 205

Pro Ser Asp Pro Leu Glu Leu Ile Val Ser Gly Ser Leu Glu Gly Pro
    210                 215                 220

Arg Pro Ser Pro Thr Arg Ser Val Ser Thr Ala Ala Gly Pro Glu Asp
225                 230                 235                 240

Gln Pro Leu Met Pro Thr Gly Ser Val Pro His Ser Gly Leu Arg Arg
                245                 250                 255

His Trp Glu Val Leu Ile Gly Val Leu Val Val Ser Ile Leu Leu Leu
            260                 265                 270

Ser Leu Leu Leu Phe Leu Leu Leu Gln His Trp Arg Gln Gly Lys His
        275                 280                 285

Arg Thr Leu Ala Gln Arg Gln Ala Asp Phe Gln Arg Pro Pro Gly Ala
    290                 295                 300

Ala Glu Pro Glu Pro Lys Asp Gly Gly Leu Gln Arg Arg Ser Ser Pro
305                 310                 315                 320

Ala Ala Asp Val Gln Gly Glu Asn Phe Cys Ala Ala Val Lys Asn Thr
                325                 330                 335
```

```
Gln Pro Glu Asp Gly Val Glu Met Asp Thr Arg Gln Ser Pro His Asp
                340                 345                 350

Glu Asp Pro Gln Ala Val Thr Tyr Ala Lys Val Lys His Ser Arg Pro
            355                 360                 365

Arg Arg Glu Met Ala Ser Pro Pro Ser Pro Leu Ser Gly Glu Phe Leu
370                 375                 380

Asp Thr Lys Asp Arg Gln Ala Glu Glu Asp Arg Gln Met Asp Thr Glu
385                 390                 395                 400

Ala Ala Ala Ser Glu Ala Pro Gln Asp Val Thr Tyr Ala Arg Leu His
                405                 410                 415

Ser Phe Thr Leu Arg Gln Lys Ala Thr Glu Pro Pro Pro Ser Gln Glu
                420                 425                 430

Gly Ala Ser Pro Ala Glu Pro Ser Val Tyr Ala Thr Leu Ala Ile His
                435                 440                 445

<210> SEQ ID NO 30
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ccatagttcc attttacagt tacc                                           24

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
gggaccaagg gatagacaga                                                20

<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
tccagagttc caggtcaagg tcac                                           24

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gccagtggat agaccgatgg                                                20

<210> SEQ ID NO 34
<211> LENGTH: 36
<212> TYPE: DNA
<213> ORGANISM: Artificial Sequence
```

```
<220> FEATURE:
<223> OTHER INFORMATION: Description of Artificial Sequence: Synthetic
      primer
<220> FEATURE:
<221> NAME/KEY: modified_base
<222> LOCATION: (24)..(25)
<223> OTHER INFORMATION: Inosine
<220> FEATURE:
<221> NAME/KEY: modified_base
<222> LOCATION: (29)..(30)
<223> OTHER INFORMATION: Inosine
<220> FEATURE:
<221> NAME/KEY: modified_base
<222> LOCATION: (34)..(35)
<223> OTHER INFORMATION: Inosine

<400> SEQUENCE: 34
ggccacgcgt cgactagtac gggnngggnn gggnng                               36

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
ggccacgcgt cgactagtac                                                 20

<210> SEQ ID NO 36
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
ttcactgcca tcaatcttcc actt                                            24

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
gatggataca gttggtgcag c                                               21

<210> SEQ ID NO 38
<211> LENGTH: 408
<212> TYPE: DNA
<213> ORGANISM: Mus musculus
<220> FEATURE:
<221> NAME/KEY: CDS
<222> LOCATION: (1)..(408)
<220> FEATURE:
<221> NAME/KEY: sig_peptide
<222> LOCATION: (1)..(54)
<220> FEATURE:
<221> NAME/KEY: mat_peptide
<222> LOCATION: (55)..(408)

<400> SEQUENCE: 38 atg aga gtg ctg att ctt ttg tgg ctg ttc aca gcc ttt cct ggt atc      48
Met Arg Val Leu Ile Leu Leu Trp Leu Phe Thr Ala Phe Pro Gly Ile
        -15                 -10                 -5
```

```
ctg tct gat gtg cag ctt cag gag tcg gga cct ggc ctg gtg aaa cct        96
Leu Ser Asp Val Gln Leu Gln Glu Ser Gly Pro Gly Leu Val Lys Pro
    -1  1               5                   10 tct cag tct ctg tcc ctc acc tgc act gtc act ggc tac tca atc acc       144
Ser Gln Ser Leu Ser Leu Thr Cys Thr Val Thr Gly Tyr Ser Ile Thr
15              20                  25                  30 agt gat tat gcc tgg aac tgg atc cgg cag ttt cca gga aac aaa ctg       192
Ser Asp Tyr Ala Trp Asn Trp Ile Arg Gln Phe Pro Gly Asn Lys Leu
                35                  40                  45 gag tgg atg ggc tac ata agc tac agt ggt agc act agc tac aac cca       240
Glu Trp Met Gly Tyr Ile Ser Tyr Ser Gly Ser Thr Ser Tyr Asn Pro
            50                  55                  60 tct ctc aaa agt cga atc tct atc act cga gac aca tcc aag aac cag       288
Ser Leu Lys Ser Arg Ile Ser Ile Thr Arg Asp Thr Ser Lys Asn Gln
        65                  70                  75 ttc ttc ctg cag ttg aat tct gtg act act gag gac aca gcc aca tat       336
Phe Phe Leu Gln Leu Asn Ser Val Thr Thr Glu Asp Thr Ala Thr Tyr
80                  85                  90 tac tgt gca aga tct ccc cct tac tat gct atg gac tac tgg ggt caa       384
Tyr Cys Ala Arg Ser Pro Pro Tyr Tyr Ala Met Asp Tyr Trp Gly Gln
95              100                 105                 110 gga acc tca gtc acc gtc tcc tca                                       408
Gly Thr Ser Val Thr Val Ser Ser
                115

<210> SEQ ID NO 39
<211> LENGTH: 136
<212> TYPE: PRT
<213> ORGANISM: Mus musculus

<400> SEQUENCE: 39

Met Arg Val Leu Ile Leu Leu Trp Leu Phe Thr Ala Phe Pro Gly Ile
                -15                 -10                 -5

Leu Ser Asp Val Gln Leu Gln Glu Ser Gly Pro Gly Leu Val Lys Pro
    -1  1               5                   10

Ser Gln Ser Leu Ser Leu Thr Cys Thr Val Thr Gly Tyr Ser Ile Thr
15              20                  25                  30

Ser Asp Tyr Ala Trp Asn Trp Ile Arg Gln Phe Pro Gly Asn Lys Leu
                35                  40                  45

Glu Trp Met Gly Tyr Ile Ser Tyr Ser Gly Ser Thr Ser Tyr Asn Pro
            50                  55                  60

Ser Leu Lys Ser Arg Ile Ser Ile Thr Arg Asp Thr Ser Lys Asn Gln
        65                  70                  75

Phe Phe Leu Gln Leu Asn Ser Val Thr Thr Glu Asp Thr Ala Thr Tyr
80                  85                  90

Tyr Cys Ala Arg Ser Pro Pro Tyr Tyr Ala Met Asp Tyr Trp Gly Gln
95              100                 105                 110

Gly Thr Ser Val Thr Val Ser Ser
                115

<210> SEQ ID NO 40
<211> LENGTH: 381
<212> TYPE: DNA
<213> ORGANISM: Mus musculus
<220> FEATURE:
<221> NAME/KEY: CDS
<222> LOCATION: (1)..(381)
<220> FEATURE:
<221> NAME/KEY: sig_peptide
<222> LOCATION: (1)..(60)
```

```
<220> FEATURE:
<221> NAME/KEY: mat_peptide
<222> LOCATION: (61)..(381)

<400> SEQUENCE: 40 atg gag aca cat tct cag gtc ttt gta tac atg ttg ctg tgg ttg tct      48
Met Glu Thr His Ser Gln Val Phe Val Tyr Met Leu Leu Trp Leu Ser
-20             -15                 -10                 -5 ggt gtt gaa gga gac att gtg atg acc cag tct cac aaa ttc atg tcc      96
Gly Val Glu Gly Asp Ile Val Met Thr Gln Ser His Lys Phe Met Ser
            -1   1              5                   10 aca tca gta gga gac agg gtc agc atc acc tgc aag gcc agt cag gat     144
Thr Ser Val Gly Asp Arg Val Ser Ile Thr Cys Lys Ala Ser Gln Asp
        15                  20                  25 gtg ggt act gct gta gcc tgg tat caa cag aaa cca ggg caa tct cct     192
Val Gly Thr Ala Val Ala Trp Tyr Gln Gln Lys Pro Gly Gln Ser Pro
    30                  35                  40 aaa cta ctg att tac tgg gca tcc acc cgg cac act gga gtc cct gat     240
Lys Leu Leu Ile Tyr Trp Ala Ser Thr Arg His Thr Gly Val Pro Asp
45                  50                  55                  60 cgc ttc aca ggc agt gga tct ggg aca gat ttc act ctc acc att agc     288
Arg Phe Thr Gly Ser Gly Ser Gly Thr Asp Phe Thr Leu Thr Ile Ser
                65                  70                  75 aat gtg cag tct gaa gac ttg gca gat tat ttc tgt cag caa tat agc     336
Asn Val Gln Ser Glu Asp Leu Ala Asp Tyr Phe Cys Gln Gln Tyr Ser
            80                  85                  90 agc tat cct ctc acg ttc ggt gct ggg acc aag ctg gag ctg aaa         381
Ser Tyr Pro Leu Thr Phe Gly Ala Gly Thr Lys Leu Glu Leu Lys
        95                  100                 105

<210> SEQ ID NO 41
<211> LENGTH: 127
<212> TYPE: PRT
<213> ORGANISM: Mus musculus

<400> SEQUENCE: 41

Met Glu Thr His Ser Gln Val Phe Val Tyr Met Leu Leu Trp Leu Ser
-20             -15                 -10                 -5

Gly Val Glu Gly Asp Ile Val Met Thr Gln Ser His Lys Phe Met Ser
            -1   1              5                   10

Thr Ser Val Gly Asp Arg Val Ser Ile Thr Cys Lys Ala Ser Gln Asp
        15                  20                  25

Val Gly Thr Ala Val Ala Trp Tyr Gln Gln Lys Pro Gly Gln Ser Pro
    30                  35                  40

Lys Leu Leu Ile Tyr Trp Ala Ser Thr Arg His Thr Gly Val Pro Asp
45                  50                  55                  60

Arg Phe Thr Gly Ser Gly Ser Gly Thr Asp Phe Thr Leu Thr Ile Ser
                65                  70                  75

Asn Val Gln Ser Glu Asp Leu Ala Asp Tyr Phe Cys Gln Gln Tyr Ser
            80                  85                  90

Ser Tyr Pro Leu Thr Phe Gly Ala Gly Thr Lys Leu Glu Leu Lys
        95                  100                 105

<210> SEQ ID NO 42
<211> LENGTH: 414
<212> TYPE: DNA
<213> ORGANISM: Mus musculus
<220> FEATURE:
<221> NAME/KEY: CDS
<222> LOCATION: (1)..(414)
```

```
<220> FEATURE:
<221> NAME/KEY: sig_peptide
<222> LOCATION: (1)..(57)
<220> FEATURE:
<221> NAME/KEY: mat_peptide
<222> LOCATION: (55)..(414)

<400> SEQUENCE: 42 atg gga tgg agc tgg gtc ttt ctc ttc ctc ctg tca gga act gca ggt      48
Met Gly Trp Ser Trp Val Phe Leu Phe Leu Leu Ser Gly Thr Ala Gly
        -15                 -10                 -5 gtc cac tgc cag gtc cag ctg aag cag tct gga gct gag ctg gtg agg      96
Val His Cys Gln Val Gln Leu Lys Gln Ser Gly Ala Glu Leu Val Arg
    -1  1               5                   10 cct ggg gct tca gtg aag ctg tcc tgc aag act tct gga tac atc ttc     144
Pro Gly Ala Ser Val Lys Leu Ser Cys Lys Thr Ser Gly Tyr Ile Phe
 15                  20                  25                  30 acc agc tac tgg att cac tgg gta aaa cag agg tct gga cag ggc ctt     192
Thr Ser Tyr Trp Ile His Trp Val Lys Gln Arg Ser Gly Gln Gly Leu
                 35                  40                  45 gag tgg att gca agg att tat cct gga act ggt agt act tac tac aat     240
Glu Trp Ile Ala Arg Ile Tyr Pro Gly Thr Gly Ser Thr Tyr Tyr Asn
             50                  55                  60 gag aag ttc aag ggc aag gcc aca ctg act gca gac aaa tcc tcc agc     288
Glu Lys Phe Lys Gly Lys Ala Thr Leu Thr Ala Asp Lys Ser Ser Ser
         65                  70                  75 act gcc tac atg cag ctc agc agc ctg aaa tct gag gac tct gct gtc     336
Thr Ala Tyr Met Gln Leu Ser Ser Leu Lys Ser Glu Asp Ser Ala Val
     80                  85                  90 tat ttc tgt gca aga tac cct acc tac gac tgg tac ttc gat gtc tgg     384
Tyr Phe Cys Ala Arg Tyr Pro Thr Tyr Asp Trp Tyr Phe Asp Val Trp
 95                 100                 105                 110 ggc gca ggg acc acg gtc acc gtc tcc tca                             414
Gly Ala Gly Thr Thr Val Thr Val Ser Ser
                115                 120

<210> SEQ ID NO 43
<211> LENGTH: 138
<212> TYPE: PRT
<213> ORGANISM: Mus musculus

<400> SEQUENCE: 43

Met Gly Trp Ser Trp Val Phe Leu Phe Leu Leu Ser Gly Thr Ala Gly
        -15                 -10                 -5

Val His Cys Gln Val Gln Leu Lys Gln Ser Gly Ala Glu Leu Val Arg
    -1  1               5                   10

Pro Gly Ala Ser Val Lys Leu Ser Cys Lys Thr Ser Gly Tyr Ile Phe
 15                  20                  25

Thr Ser Tyr Trp Ile His Trp Val Lys Gln Arg Ser Gly Gln Gly Leu
 30                  35                  40                  45

Glu Trp Ile Ala Arg Ile Tyr Pro Gly Thr Gly Ser Thr Tyr Tyr Asn
             50                  55                  60

Glu Lys Phe Lys Gly Lys Ala Thr Leu Thr Ala Asp Lys Ser Ser Ser
         65                  70                  75

Thr Ala Tyr Met Gln Leu Ser Ser Leu Lys Ser Glu Asp Ser Ala Val
     80                  85                  90

Tyr Phe Cys Ala Arg Tyr Pro Thr Tyr Asp Trp Tyr Phe Asp Val Trp
 95                 100                 105

Gly Ala Gly Thr Thr Val Thr Val Ser Ser
110                 115
```

<210> SEQ ID NO 44
<211> LENGTH: 381
<212> TYPE: DNA
<213> ORGANISM: Mus musculus
<220> FEATURE:
<221> NAME/KEY: CDS
<222> LOCATION: (1)..(381)
<220> FEATURE:
<221> NAME/KEY: sig_peptide
<222> LOCATION: (1)..(60)
<220> FEATURE:
<221> NAME/KEY: mat_peptide
<222> LOCATION: (61)..(381)

<400> SEQUENCE: 44

```
atg gtt ttc aca cct cag att ctt gga ctt atg ctt ttc tgg att tca       48
Met Val Phe Thr Pro Gln Ile Leu Gly Leu Met Leu Phe Trp Ile Ser
-20             -15                 -10                 -5 gcc tcc aga ggt gat att gtg cta act cag tct cca gcc acc ctg tct       96
Ala Ser Arg Gly Asp Ile Val Leu Thr Gln Ser Pro Ala Thr Leu Ser
            -1  1               5                   10 gtg act cca gga gat aga gtc agt ctt tcc tgc agg gcc agt caa agt      144
Val Thr Pro Gly Asp Arg Val Ser Leu Ser Cys Arg Ala Ser Gln Ser
        15                  20                  25 att agc aac tac cta cac tgg tat caa caa aaa tca cat gag tct cca      192
Ile Ser Asn Tyr Leu His Trp Tyr Gln Gln Lys Ser His Glu Ser Pro
    30                  35                  40 agg ctt ctc atc aag tat gct tcc cag tcc atc tct ggg atc ccc tcc      240
Arg Leu Leu Ile Lys Tyr Ala Ser Gln Ser Ile Ser Gly Ile Pro Ser
45                  50                  55                  60 agg ttc agt ggc agt gga tca ggg aca gat ttc act ctc agt atc aac      288
Arg Phe Ser Gly Ser Gly Ser Gly Thr Asp Phe Thr Leu Ser Ile Asn
                65                  70                  75 agt gtg gag act gaa gat ttt gga atg tat ttc tgt caa cag agt aac      336
Ser Val Glu Thr Glu Asp Phe Gly Met Tyr Phe Cys Gln Gln Ser Asn
            80                  85                  90 agc tgg ccg ctc acg ttc ggt gct ggg acc aag ctg gag ctg aaa          381
Ser Trp Pro Leu Thr Phe Gly Ala Gly Thr Lys Leu Glu Leu Lys
        95                  100                 105
```

<210> SEQ ID NO 45
<211> LENGTH: 127
<212> TYPE: PRT
<213> ORGANISM: Mus musculus

<400> SEQUENCE: 45

```
Met Val Phe Thr Pro Gln Ile Leu Gly Leu Met Leu Phe Trp Ile Ser
-20             -15                 -10                 -5

Ala Ser Arg Gly Asp Ile Val Leu Thr Gln Ser Pro Ala Thr Leu Ser
            -1  1               5                   10

Val Thr Pro Gly Asp Arg Val Ser Leu Ser Cys Arg Ala Ser Gln Ser
        15                  20                  25

Ile Ser Asn Tyr Leu His Trp Tyr Gln Gln Lys Ser His Glu Ser Pro
    30                  35                  40

Arg Leu Leu Ile Lys Tyr Ala Ser Gln Ser Ile Ser Gly Ile Pro Ser
45                  50                  55                  60

Arg Phe Ser Gly Ser Gly Ser Gly Thr Asp Phe Thr Leu Ser Ile Asn
                65                  70                  75

Ser Val Glu Thr Glu Asp Phe Gly Met Tyr Phe Cys Gln Gln Ser Asn
            80                  85                  90

Ser Trp Pro Leu Thr Phe Gly Ala Gly Thr Lys Leu Glu Leu Lys
        95                  100                 105
```

<210> SEQ ID NO 46
<211> LENGTH: 408
<212> TYPE: DNA
<213> ORGANISM: Mus musculus
<220> FEATURE:
<221> NAME/KEY: CDS
<222> LOCATION: (1)..(408)
<220> FEATURE:
<221> NAME/KEY: sig_peptide
<222> LOCATION: (1)..(54)
<220> FEATURE:
<221> NAME/KEY: mat_peptide
<222> LOCATION: (55)..(408)

<400> SEQUENCE: 46

```
atg aga gtg ctg att ctt ttg tgg ctg ttc aca gcc ttt cct ggt atc      48
Met Arg Val Leu Ile Leu Leu Trp Leu Phe Thr Ala Phe Pro Gly Ile
        -15                 -10                 -5 ctg tct gat gtg cag ctt cag gag tcg gga cct ggc ctg gtg aaa cct      96
Leu Ser Asp Val Gln Leu Gln Glu Ser Gly Pro Gly Leu Val Lys Pro
     -1   1               5                  10 tct cag tct ctg tcc ctc acc tgc act gtc act ggc tac tca atc acc     144
Ser Gln Ser Leu Ser Leu Thr Cys Thr Val Thr Gly Tyr Ser Ile Thr
 15                  20                  25                  30 agt gat tat gcc tgg aac tgg atc cgg cag ttt cca gga aac aaa ctg     192
Ser Asp Tyr Ala Trp Asn Trp Ile Arg Gln Phe Pro Gly Asn Lys Leu
                 35                  40                  45 gag tgg atg ggc tac ata agc tac agt ggt agc act agc tac aac cca     240
Glu Trp Met Gly Tyr Ile Ser Tyr Ser Gly Ser Thr Ser Tyr Asn Pro
             50                  55                  60 tct ctc aaa agt cga atc tct atc act cga gac aca tcc aag aac cag     288
Ser Leu Lys Ser Arg Ile Ser Ile Thr Arg Asp Thr Ser Lys Asn Gln
         65                  70                  75 ttc ttc ctg cag ttg aat tct gtg act act gag gac aca gcc aca tat     336
Phe Phe Leu Gln Leu Asn Ser Val Thr Thr Glu Asp Thr Ala Thr Tyr
     80                  85                  90 tac tgt gca aga gcc ctc cca tta ccc tgg ttt gct tac tgg ggc caa     384
Tyr Cys Ala Arg Ala Leu Pro Leu Pro Trp Phe Ala Tyr Trp Gly Gln
 95                 100                 105                 110 ggg act ctg gtc act gtc tct gca                                     408
Gly Thr Leu Val Thr Val Ser Ala
                115
```

<210> SEQ ID NO 47
<211> LENGTH: 136
<212> TYPE: PRT
<213> ORGANISM: Mus musculus

<400> SEQUENCE: 47

```
Met Arg Val Leu Ile Leu Leu Trp Leu Phe Thr Ala Phe Pro Gly Ile
        -15                 -10                 -5

Leu Ser Asp Val Gln Leu Gln Glu Ser Gly Pro Gly Leu Val Lys Pro
     -1   1               5                  10

Ser Gln Ser Leu Ser Leu Thr Cys Thr Val Thr Gly Tyr Ser Ile Thr
 15                  20                  25                  30

Ser Asp Tyr Ala Trp Asn Trp Ile Arg Gln Phe Pro Gly Asn Lys Leu
                 35                  40                  45

Glu Trp Met Gly Tyr Ile Ser Tyr Ser Gly Ser Thr Ser Tyr Asn Pro
             50                  55                  60

Ser Leu Lys Ser Arg Ile Ser Ile Thr Arg Asp Thr Ser Lys Asn Gln
         65                  70                  75

Phe Phe Leu Gln Leu Asn Ser Val Thr Thr Glu Asp Thr Ala Thr Tyr
     80                  85                  90
```

```
Tyr Cys Ala Arg Ala Leu Pro Leu Pro Trp Phe Ala Tyr Trp Gly Gln
 95                 100                 105                 110

Gly Thr Leu Val Thr Val Ser Ala
                115

<210> SEQ ID NO 48
<211> LENGTH: 381
<212> TYPE: DNA
<213> ORGANISM: Mus musculus
<220> FEATURE:
<221> NAME/KEY: CDS
<222> LOCATION: (1)..(381)
<220> FEATURE:
<221> NAME/KEY: sig_peptide
<222> LOCATION: (1)..(60)
<220> FEATURE:
<221> NAME/KEY: mat_peptide
<222> LOCATION: (61)..(381)

<400> SEQUENCE: 48 atg gag aca cat tct cag gtc ttt gta tac atg ttg ctg tgg ttg tct        48
Met Glu Thr His Ser Gln Val Phe Val Tyr Met Leu Leu Trp Leu Ser
-20                 -15                 -10                 -5 ggt gtt gaa gga gac att gtg atg acc cag tct cac aaa ttc atg tcc        96
Gly Val Glu Gly Asp Ile Val Met Thr Gln Ser His Lys Phe Met Ser
             -1  1               5                   10 aca tca gta gga gac agg gtc agc atc acc tgc aag gcc agt cag gat       144
Thr Ser Val Gly Asp Arg Val Ser Ile Thr Cys Lys Ala Ser Gln Asp
                 15                  20                  25 gtg ggt act gct gta gcc tgg tat caa cag aaa cca ggg caa tct cct       192
Val Gly Thr Ala Val Ala Trp Tyr Gln Gln Lys Pro Gly Gln Ser Pro
         30                  35                  40 aaa cta ctg att tac tgg gca tcc acc cgg cac act gga gtc cct gat       240
Lys Leu Leu Ile Tyr Trp Ala Ser Thr Arg His Thr Gly Val Pro Asp
 45                  50                  55                  60 cgc ttc aca ggc agt gga tct ggg aca gat ttc act ctc acc att agc       288
Arg Phe Thr Gly Ser Gly Ser Gly Thr Asp Phe Thr Leu Thr Ile Ser
                 65                  70                  75 aat gtg cag tct gaa gac ttg gca gat tat ttc tgt cag caa tat agc       336
Asn Val Gln Ser Glu Asp Leu Ala Asp Tyr Phe Cys Gln Gln Tyr Ser
         80                  85                  90 agc tat cct tac acg ttc gga ggg ggg acc aag ctg gaa ata aaa           381
Ser Tyr Pro Tyr Thr Phe Gly Gly Gly Thr Lys Leu Glu Ile Lys
             95                  100                 105

<210> SEQ ID NO 49
<211> LENGTH: 127
<212> TYPE: PRT
<213> ORGANISM: Mus musculus

<400> SEQUENCE: 49

Met Glu Thr His Ser Gln Val Phe Val Tyr Met Leu Leu Trp Leu Ser
-20                 -15                 -10                 -5

Gly Val Glu Gly Asp Ile Val Met Thr Gln Ser His Lys Phe Met Ser
             -1  1               5                   10

Thr Ser Val Gly Asp Arg Val Ser Ile Thr Cys Lys Ala Ser Gln Asp
                 15                  20                  25

Val Gly Thr Ala Val Ala Trp Tyr Gln Gln Lys Pro Gly Gln Ser Pro
         30                  35                  40

Lys Leu Leu Ile Tyr Trp Ala Ser Thr Arg His Thr Gly Val Pro Asp
 45                  50                  55                  60

Arg Phe Thr Gly Ser Gly Ser Gly Thr Asp Phe Thr Leu Thr Ile Ser
                 65                  70                  75
```

```
Asn Val Gln Ser Glu Asp Leu Ala Asp Tyr Phe Cys Gln Gln Tyr Ser
            80                  85                  90

Ser Tyr Pro Tyr Thr Phe Gly Gly Gly Thr Lys Leu Glu Ile Lys
            95                  100                 105

<210> SEQ ID NO 50
<211> LENGTH: 1401
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(1398)
<220> FEATURE:
<221> NAME/KEY: sig_peptide
<222> LOCATION: (1)..(54)
<220> FEATURE:
<221> NAME/KEY: mat_peptide
<222> LOCATION: (55)..(1398)

<400> SEQUENCE: 50 atg aga gtg ctg att ctt ttg tgg ctg ttc aca gcc ttt cct ggt atc      48
Met Arg Val Leu Ile Leu Leu Trp Leu Phe Thr Ala Phe Pro Gly Ile
            -15                 -10                 -5 ctg tct gat gtg cag ctt cag gag tcg gga cct ggc ctg gtg aaa cct      96
Leu Ser Asp Val Gln Leu Gln Glu Ser Gly Pro Gly Leu Val Lys Pro
    -1  1               5                   10 tct cag tct ctg tcc ctc acc tgc act gtc act ggc tac tca atc acc     144
Ser Gln Ser Leu Ser Leu Thr Cys Thr Val Thr Gly Tyr Ser Ile Thr
15                  20                  25                  30 agt gat tat gcc tgg aac tgg atc cgg cag ttt cca gga aac aaa ctg     192
Ser Asp Tyr Ala Trp Asn Trp Ile Arg Gln Phe Pro Gly Asn Lys Leu
                35                  40                  45 gag tgg atg ggc tac ata agc tac agt ggt agc act agc tac aac cca     240
Glu Trp Met Gly Tyr Ile Ser Tyr Ser Gly Ser Thr Ser Tyr Asn Pro
            50                  55                  60 tct ctc aaa agt cga atc tct atc act cga gac aca tcc aag aac cag     288
Ser Leu Lys Ser Arg Ile Ser Ile Thr Arg Asp Thr Ser Lys Asn Gln
65                  70                  75 ttc ttc ctg cag ttg aat tct gtg act act gag gac aca gcc aca tat     336
Phe Phe Leu Gln Leu Asn Ser Val Thr Thr Glu Asp Thr Ala Thr Tyr
                85                  90 tac tgt gca aga tct ccc cct tac tat gct atg gac tac tgg ggt caa     384
Tyr Cys Ala Arg Ser Pro Pro Tyr Tyr Ala Met Asp Tyr Trp Gly Gln
95                  100                 105                 110 gga acc tca gtc acc gtc tcc tca gcc tcc acc aag ggc cca tcg gtc     432
Gly Thr Ser Val Thr Val Ser Ser Ala Ser Thr Lys Gly Pro Ser Val
                115                 120                 125 ttc ccc ctg gca ccc tcc tcc aag agc acc tct ggg ggc aca gcg gcc     480
Phe Pro Leu Ala Pro Ser Ser Lys Ser Thr Ser Gly Gly Thr Ala Ala
            130                 135                 140 ctg ggc tgc ctg gtc aag gac tac ttc ccc gaa ccg gtg acg gtg tcg     528
Leu Gly Cys Leu Val Lys Asp Tyr Phe Pro Glu Pro Val Thr Val Ser
            145                 150                 155 tgg aac tca ggc gcc ctg acc agc ggc gtg cac acc ttc ccg gct gtc     576
Trp Asn Ser Gly Ala Leu Thr Ser Gly Val His Thr Phe Pro Ala Val
            160                 165                 170 cta cag tcc tca gga ctc tac tcc ctc agc agc gtg gtg acc gtg ccc     624
Leu Gln Ser Ser Gly Leu Tyr Ser Leu Ser Ser Val Val Thr Val Pro
175                 180                 185                 190
```

```
tcc agc agc ttg ggc acc cag acc tac atc tgc aac gtg aat cac aag      672
Ser Ser Ser Leu Gly Thr Gln Thr Tyr Ile Cys Asn Val Asn His Lys
            195                 200                 205 ccc agc aac acc aag gtg gac aag aaa gtt gag ccc aaa tct tgt gac      720
Pro Ser Asn Thr Lys Val Asp Lys Lys Val Glu Pro Lys Ser Cys Asp
                210                 215                 220 aaa act cac aca tgc cca ccg tgc cca gca cct gaa ctc ctg ggg gga      768
Lys Thr His Thr Cys Pro Pro Cys Pro Ala Pro Glu Leu Leu Gly Gly
            225                 230                 235 ccg tca gtc ttc ctc ttc ccc cca aaa ccc aag gac acc ctc atg atc      816
Pro Ser Val Phe Leu Phe Pro Pro Lys Pro Lys Asp Thr Leu Met Ile
    240                 245                 250 tcc cgg acc cct gag gtc aca tgc gtg gtg gtg gac gtg agc cac gaa      864
Ser Arg Thr Pro Glu Val Thr Cys Val Val Val Asp Val Ser His Glu
255                 260                 265                 270 gac cct gag gtc aag ttc aac tgg tac gtg gac ggc gtg gag gtg cat      912
Asp Pro Glu Val Lys Phe Asn Trp Tyr Val Asp Gly Val Glu Val His
                275                 280                 285 aat gcc aag aca aag ccg cgg gag gag cag tac aac agc acg tac cgt      960
Asn Ala Lys Thr Lys Pro Arg Glu Glu Gln Tyr Asn Ser Thr Tyr Arg
            290                 295                 300 gtg gtc agc gtc ctc acc gtc ctg cac cag gac tgg ctg aat ggc aag     1008
Val Val Ser Val Leu Thr Val Leu His Gln Asp Trp Leu Asn Gly Lys
                305                 310                 315 gag tac aag tgc aag gtc tcc aac aaa gcc ctc cca gcc ccc atc gag     1056
Glu Tyr Lys Cys Lys Val Ser Asn Lys Ala Leu Pro Ala Pro Ile Glu
    320                 325                 330 aaa acc atc tcc aaa gcc aaa ggg cag ccc cga gaa cca cag gtg tac     1104
Lys Thr Ile Ser Lys Ala Lys Gly Gln Pro Arg Glu Pro Gln Val Tyr
335                 340                 345                 350 acc ctg ccc cca tcc cgg gat gag ctg acc aag aac cag gtc agc ctg     1152
Thr Leu Pro Pro Ser Arg Asp Glu Leu Thr Lys Asn Gln Val Ser Leu
                355                 360                 365 acc tgc ctg gtc aaa ggc ttc tat ccc agc gac atc gcc gtg gag tgg     1200
Thr Cys Leu Val Lys Gly Phe Tyr Pro Ser Asp Ile Ala Val Glu Trp
            370                 375                 380 gag agc aat ggg cag ccg gag aac aac tac aag acc acg cct ccc gtg     1248
Glu Ser Asn Gly Gln Pro Glu Asn Asn Tyr Lys Thr Thr Pro Pro Val
    385                 390                 395 ctg gac tcc gac ggc tcc ttc ttc ctc tac agc aag ctc acc gtg gac     1296
Leu Asp Ser Asp Gly Ser Phe Phe Leu Tyr Ser Lys Leu Thr Val Asp
400                 405                 410 aag agc agg tgg cag cag ggg aac gtc ttc tca tgc tcc gtg atg cat     1344
Lys Ser Arg Trp Gln Gln Gly Asn Val Phe Ser Cys Ser Val Met His
415                 420                 425                 430 gag gct ctg cac aac cac tac acg cag aag agc ctc tcc ctg tct ccg     1392
Glu Ala Leu His Asn His Tyr Thr Gln Lys Ser Leu Ser Leu Ser Pro
                435                 440                 445 ggt aaa tga                                                         1401
Gly Lys <210> SEQ ID NO 51
<211> LENGTH: 466
<212> TYPE: PRT
<213> ORGANISM: Artificial Sequence
<220> FEATURE:
<223> OTHER INFORMATION: Description of Artificial Sequence: Synthetic
      construct
```

```
<400> SEQUENCE: 51

Met Arg Val Leu Ile Leu Leu Trp Leu Phe Thr Ala Phe Pro Gly Ile
         -15                 -10                  -5

Leu Ser Asp Val Gln Leu Gln Glu Ser Gly Pro Gly Leu Val Lys Pro
     -1   1                   5                  10

Ser Gln Ser Leu Ser Leu Thr Cys Thr Val Thr Gly Tyr Ser Ile Thr
 15                  20                  25                  30

Ser Asp Tyr Ala Trp Asn Trp Ile Arg Gln Phe Pro Gly Asn Lys Leu
                 35                  40                  45

Glu Trp Met Gly Tyr Ile Ser Tyr Ser Gly Ser Thr Tyr Asn Pro
             50                  55                  60

Ser Leu Lys Ser Arg Ile Ser Ile Thr Arg Asp Thr Ser Lys Asn Gln
         65                  70                  75

Phe Phe Leu Gln Leu Asn Ser Val Thr Thr Glu Asp Thr Ala Thr Tyr
     80                  85                  90

Tyr Cys Ala Arg Ser Pro Pro Tyr Tyr Ala Met Asp Tyr Trp Gly Gln
 95                 100                 105                 110

Gly Thr Ser Val Thr Val Ser Ser Ala Ser Thr Lys Gly Pro Ser Val
                115                 120                 125

Phe Pro Leu Ala Pro Ser Ser Lys Ser Thr Ser Gly Gly Thr Ala Ala
                130                 135                 140

Leu Gly Cys Leu Val Lys Asp Tyr Phe Pro Glu Pro Val Thr Val Ser
            145                 150                 155

Trp Asn Ser Gly Ala Leu Thr Ser Gly Val His Thr Phe Pro Ala Val
        160                 165                 170

Leu Gln Ser Ser Gly Leu Tyr Ser Leu Ser Ser Val Val Thr Val Pro
175                 180                 185                 190

Ser Ser Ser Leu Gly Thr Gln Thr Tyr Ile Cys Asn Val Asn His Lys
                195                 200                 205

Pro Ser Asn Thr Lys Val Asp Lys Val Glu Pro Lys Ser Cys Asp
                210                 215                 220

Lys Thr His Thr Cys Pro Pro Cys Pro Ala Pro Glu Leu Leu Gly Gly
            225                 230                 235

Pro Ser Val Phe Leu Phe Pro Pro Lys Pro Lys Asp Thr Leu Met Ile
        240                 245                 250

Ser Arg Thr Pro Glu Val Thr Cys Val Val Val Asp Val Ser His Glu
255                 260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Asn Ser Thr Tyr Arg
                290                 295                 300

Val Val Ser Val Leu Thr Val Leu His Gln Asp Trp Leu Asn Gly Lys
                305                 310                 315

Glu Tyr Lys Cys Lys Val Ser Asn Lys Ala Leu Pro Ala Pro Ile Glu
            320                 325                 330

Lys Thr Ile Ser Lys Ala Lys Gly Gln Pro Arg Glu Pro Gln Val Tyr
335                 340                 345                 350

Thr Leu Pro Pro Ser Arg Asp Glu Leu Thr Lys Asn Gln Val Ser Leu
                355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
                385                 390                 395
```

```
Leu Asp Ser Asp Gly Ser Phe Phe Leu Tyr Ser Lys Leu Thr Val Asp
    400                 405                 410

Lys Ser Arg Trp Gln Gln Gly Asn Val Phe Ser Cys Ser Val Met His
415                 420                 425                 430

Glu Ala Leu His Asn His Tyr Thr Gln Lys Ser Leu Ser Leu Ser Pro
                435                 440                 445

Gly Lys

<210> SEQ ID NO 52
<211> LENGTH: 705
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(702)
<220> FEATURE:
<221> NAME/KEY: sig_peptide
<222> LOCATION: (1)..(60)
<220> FEATURE:
<221> NAME/KEY: mat_peptide
<222> LOCATION: (61)..(702)

<400> SEQUENCE: 52 atg gag aca cat tct cag gtc ttt gta tac atg ttg ctg tgg ttg tct      48
Met Glu Thr His Ser Gln Val Phe Val Tyr Met Leu Leu Trp Leu Ser
-20                 -15                 -10                  -5 ggt gtt gaa gga gac att gtg atg acc cag tct cac aaa ttc atg tcc      96
Gly Val Glu Gly Asp Ile Val Met Thr Gln Ser His Lys Phe Met Ser
          -1   1               5                  10 aca tca gta gga gac agg gtc agc atc acc tgc aag gcc agt cag gat     144
Thr Ser Val Gly Asp Arg Val Ser Ile Thr Cys Lys Ala Ser Gln Asp
             15                  20                  25 gtg ggt act gct gta gcc tgg tat caa cag aaa cca ggg caa tct cct     192
Val Gly Thr Ala Val Ala Trp Tyr Gln Gln Lys Pro Gly Gln Ser Pro
         30                  35                  40 aaa cta ctg att tac tgg gca tcc acc cgg cac act gga gtc cct gat     240
Lys Leu Leu Ile Tyr Trp Ala Ser Thr Arg His Thr Gly Val Pro Asp
45                  50                  55                  60 cgc ttc aca ggc agt gga tct ggg aca gat ttc act ctc acc att agc     288
Arg Phe Thr Gly Ser Gly Ser Gly Thr Asp Phe Thr Leu Thr Ile Ser
                 65                  70                  75 aat gtg cag tct gaa gac ttg gca gat tat ttc tgt cag caa tat agc     336
Asn Val Gln Ser Glu Asp Leu Ala Asp Tyr Phe Cys Gln Gln Tyr Ser
             80                  85                  90 agc tat cct ctc acg ttc ggt gct ggg acc aag ctg gag ctg aaa cga     384
Ser Tyr Pro Leu Thr Phe Gly Ala Gly Thr Lys Leu Glu Leu Lys Arg
         95                 100                 105 act gtg gct gca cca tct gtc ttc atc ttc ccg cca tct gat gag cag     432
Thr Val Ala Ala Pro Ser Val Phe Ile Phe Pro Pro Ser Asp Glu Gln
    110                 115                 120 ttg aaa tct gga act gcc tct gtt gtg tgc ctg ctg aat aac ttc tat     480
Leu Lys Ser Gly Thr Ala Ser Val Val Cys Leu Leu Asn Asn Phe Tyr
125                 130                 135                 140 ccc aga gag gcc aaa gta cag tgg aag gtg gat aac gcc ctc caa tcg     528
Pro Arg Glu Ala Lys Val Gln Trp Lys Val Asp Asn Ala Leu Gln Ser
                145                 150                 155 ggt aac tcc cag gag agt gtc aca gag cag gac agc aag gac agc acc     576
Gly Asn Ser Gln Glu Ser Val Thr Glu Gln Asp Ser Lys Asp Ser Thr
            160                 165                 170
```

```
tac agc ctc agc agc acc ctg acg ctg agc aaa gca gac tac gag aaa       624
Tyr Ser Leu Ser Ser Thr Leu Thr Leu Ser Lys Ala Asp Tyr Glu Lys
        175                 180                 185 cac aaa gtc tac gcc tgc gaa gtc acc cat cag ggc ctg agc tcg ccc       672
His Lys Val Tyr Ala Cys Glu Val Thr His Gln Gly Leu Ser Ser Pro
    190                 195                 200 gtc aca aag agc ttc aac agg gga gag tgc tag                           705
Val Thr Lys Ser Phe Asn Arg Gly Glu Cys
205                 210
```

<210> SEQ ID NO 53
<211> LENGTH: 234
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 53

```
Met Glu Thr His Ser Gln Val Phe Val Tyr Met Leu Leu Trp Leu Ser
-20                 -15                 -10                  -5

Gly Val Glu Gly Asp Ile Val Met Thr Gln Ser His Lys Phe Met Ser
            -1   1                5                  10

Thr Ser Val Gly Asp Arg Val Ser Ile Thr Cys Lys Ala Ser Gln Asp
         15                  20                  25

Val Gly Thr Ala Val Ala Trp Tyr Gln Gln Lys Pro Gly Gln Ser Pro
    30                  35                  40

Lys Leu Leu Ile Tyr Trp Ala Ser Thr Arg His Thr Gly Val Pro Asp
45                  50                  55                  60

Arg Phe Thr Gly Ser Gly Ser Gly Thr Asp Phe Thr Leu Thr Ile Ser
                65                  70                  75

Asn Val Gln Ser Glu Asp Leu Ala Asp Tyr Phe Cys Gln Gln Tyr Ser
            80                  85                  90

Ser Tyr Pro Leu Thr Phe Gly Ala Gly Thr Lys Leu Glu Leu Lys Arg
        95                 100                 105

Thr Val Ala Ala Pro Ser Val Phe Ile Phe Pro Pro Ser Asp Glu Gln
    110                 115                 120

Leu Lys Ser Gly Thr Ala Ser Val Val Cys Leu Leu Asn Asn Phe Tyr
125                 130                 135                 140

Pro Arg Glu Ala Lys Val Gln Trp Lys Val Asp Asn Ala Leu Gln Ser
                145                 150                 155

Gly Asn Ser Gln Glu Ser Val Thr Glu Gln Asp Ser Lys Asp Ser Thr
            160                 165                 170

Tyr Ser Leu Ser Ser Thr Leu Thr Leu Ser Lys Ala Asp Tyr Glu Lys
        175                 180                 185

His Lys Val Tyr Ala Cys Glu Val Thr His Gln Gly Leu Ser Ser Pro
    190                 195                 200

Val Thr Lys Ser Phe Asn Arg Gly Glu Cys
205                 210
```

<210> SEQ ID NO 54
<211> LENGTH: 1407
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(1404)

```
<220> FEATURE:
<221> NAME/KEY: sig_peptide
<222> LOCATION: (1)..(57)
<220> FEATURE:
<221> NAME/KEY: mat_peptide
<222> LOCATION: (55)..(1404)

<400> SEQUENCE: 54 atg gga tgg agc tgg gtc ttt ctc ttc ctc ctg tca gga act gca ggt      48
Met Gly Trp Ser Trp Val Phe Leu Phe Leu Leu Ser Gly Thr Ala Gly
        -15                 -10                 -5 gtc cac tgc cag gtc cag ctg aag cag tct gga gct gag ctg gtg agg      96
Val His Cys Gln Val Gln Leu Lys Gln Ser Gly Ala Glu Leu Val Arg
    -1  1               5                   10 cct ggg gct tca gtg aag ctg tcc tgc aag act tct gga tac atc ttc     144
Pro Gly Ala Ser Val Lys Leu Ser Cys Lys Thr Ser Gly Tyr Ile Phe
 15                  20                  25                  30 acc agc tac tgg att cac tgg gta aaa cag agg tct gga cag ggc ctt     192
Thr Ser Tyr Trp Ile His Trp Val Lys Gln Arg Ser Gly Gln Gly Leu
                 35                  40                  45 gag tgg att gca agg att tat cct gga act ggt agt act tac tac aat     240
Glu Trp Ile Ala Arg Ile Tyr Pro Gly Thr Gly Ser Thr Tyr Tyr Asn
             50                  55                  60 gag aag ttc aag ggc aag gcc aca ctg act gca gac aaa tcc tcc agc     288
Glu Lys Phe Lys Gly Lys Ala Thr Leu Thr Ala Asp Lys Ser Ser Ser
         65                  70                  75 act gcc tac atg cag ctc agc agc ctg aaa tct gag gac tct gct gtc     336
Thr Ala Tyr Met Gln Leu Ser Ser Leu Lys Ser Glu Asp Ser Ala Val
     80                  85                  90 tat ttc tgt gca aga tac cct acc tac gac tgg tac ttc gat gtc tgg     384
Tyr Phe Cys Ala Arg Tyr Pro Thr Tyr Asp Trp Tyr Phe Asp Val Trp
 95                 100                 105                 110 ggc gca ggg acc acg gtc acc gtc tcc tca gcc tcc acc aag ggc cca     432
Gly Ala Gly Thr Thr Val Thr Val Ser Ser Ala Ser Thr Lys Gly Pro
                115                 120                 125 tcg gtc ttc ccc ctg gca ccc tcc tcc aag agc acc tct ggg ggc aca     480
Ser Val Phe Pro Leu Ala Pro Ser Ser Lys Ser Thr Ser Gly Gly Thr
            130                 135                 140 gcg gcc ctg ggc tgc ctg gtc aag gac tac ttc ccc gaa ccg gtg acg     528
Ala Ala Leu Gly Cys Leu Val Lys Asp Tyr Phe Pro Glu Pro Val Thr
        145                 150                 155 gtg tcg tgg aac tca ggc gcc ctg acc agc ggc gtg cac acc ttc ccg     576
Val Ser Trp Asn Ser Gly Ala Leu Thr Ser Gly Val His Thr Phe Pro
    160                 165                 170 gct gtc cta cag tcc tca gga ctc tac tcc ctc agc agc gtg gtg acc     624
Ala Val Leu Gln Ser Ser Gly Leu Tyr Ser Leu Ser Ser Val Val Thr
175                 180                 185                 190 gtg ccc tcc agc agc ttg ggc acc cag acc tac atc tgc aac gtg aat     672
Val Pro Ser Ser Ser Leu Gly Thr Gln Thr Tyr Ile Cys Asn Val Asn
                195                 200                 205 cac aag ccc agc aac acc aag gtg gac aag aaa gtt gag ccc aaa tct     720
His Lys Pro Ser Asn Thr Lys Val Asp Lys Lys Val Glu Pro Lys Ser
            210                 215                 220 tgt gac aaa act cac aca tgc cca ccg tgc cca gca cct gaa ctc ctg     768
Cys Asp Lys Thr His Thr Cys Pro Pro Cys Pro Ala Pro Glu Leu Leu
        225                 230                 235 ggg gga ccg tca gtc ttc ctc ttc ccc cca aaa ccc aag gac acc ctc     816
Gly Gly Pro Ser Val Phe Leu Phe Pro Pro Lys Pro Lys Asp Thr Leu
    240                 245                 250 atg atc tcc cgg acc cct gag gtc aca tgc gtg gtg gtg gac gtg agc     864
Met Ile Ser Arg Thr Pro Glu Val Thr Cys Val Val Val Asp Val Ser
255                 260                 265                 270
```

```
cac gaa gac cct gag gtc aag ttc aac tgg tac gtg gac ggc gtg gag      912
His Glu Asp Pro Glu Val Lys Phe Asn Trp Tyr Val Asp Gly Val Glu
                275                 280                 285 gtg cat aat gcc aag aca aag ccg cgg gag gag cag tac aac agc acg      960
Val His Asn Ala Lys Thr Lys Pro Arg Glu Glu Gln Tyr Asn Ser Thr
            290                 295                 300 tac cgt gtg gtc agc gtc ctc acc gtc ctg cac cag gac tgg ctg aat     1008
Tyr Arg Val Val Ser Val Leu Thr Val Leu His Gln Asp Trp Leu Asn
        305                 310                 315 ggc aag gag tac aag tgc aag gtc tcc aac aaa gcc ctc cca gcc ccc     1056
Gly Lys Glu Tyr Lys Cys Lys Val Ser Asn Lys Ala Leu Pro Ala Pro
    320                 325                 330 atc gag aaa acc atc tcc aaa gcc aaa ggg cag ccc cga gaa cca cag     1104
Ile Glu Lys Thr Ile Ser Lys Ala Lys Gly Gln Pro Arg Glu Pro Gln
335                 340                 345                 350 gtg tac acc ctg ccc cca tcc cgg gat gag ctg acc aag aac cag gtc     1152
Val Tyr Thr Leu Pro Pro Ser Arg Asp Glu Leu Thr Lys Asn Gln Val
                355                 360                 365 agc ctg acc tgc ctg gtc aaa ggc ttc tat ccc agc gac atc gcc gtg     1200
Ser Leu Thr Cys Leu Val Lys Gly Phe Tyr Pro Ser Asp Ile Ala Val
            370                 375                 380 gag tgg gag agc aat ggg cag ccg gag aac aac tac aag acc acg cct     1248
Glu Trp Glu Ser Asn Gly Gln Pro Glu Asn Asn Tyr Lys Thr Thr Pro
        385                 390                 395 ccc gtg ctg gac tcc gac ggc tcc ttc ttc ctc tac agc aag ctc acc     1296
Pro Val Leu Asp Ser Asp Gly Ser Phe Phe Leu Tyr Ser Lys Leu Thr
    400                 405                 410 gtg gac aag agc agg tgg cag cag ggg aac gtc ttc tca tgc tcc gtg     1344
Val Asp Lys Ser Arg Trp Gln Gln Gly Asn Val Phe Ser Cys Ser Val
415                 420                 425                 430 atg cat gag gct ctg cac aac cac tac acg cag aag agc ctc tcc ctg     1392
Met His Glu Ala Leu His Asn His Tyr Thr Gln Lys Ser Leu Ser Leu
                435                 440                 445 tct ccg ggt aaa tga                                                 1407
Ser Pro Gly Lys
            450

<210> SEQ ID NO 55
<211> LENGTH: 468
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 55

Met Gly Trp Ser Trp Val Phe Leu Phe Leu Leu Ser Gly Thr Ala Gly
                -15                 -10                 -5

Val His Cys Gln Val Gln Leu Lys Gln Ser Gly Ala Glu Leu Val Arg
        -1  1                5                  10

Pro Gly Ala Ser Val Lys Leu Ser Cys Lys Thr Ser Gly Tyr Ile Phe
    15                  20                  25

Thr Ser Tyr Trp Ile His Trp Val Lys Gln Arg Ser Gly Gln Gly Leu
30                  35                  40                  45

Glu Trp Ile Ala Arg Ile Tyr Pro Gly Thr Gly Ser Thr Tyr Tyr Asn
                50                  55                  60

Glu Lys Phe Lys Gly Lys Ala Thr Leu Thr Ala Asp Lys Ser Ser Ser
            65                  70                  75

Thr Ala Tyr Met Gln Leu Ser Ser Leu Lys Ser Glu Asp Ser Ala Val
        80                  85                  90
```

```
Tyr Phe Cys Ala Arg Tyr Pro Thr Tyr Asp Trp Tyr Phe Asp Val Trp
 95                 100                 105

Gly Ala Gly Thr Thr Val Thr Val Ser Ser Ala Ser Thr Lys Gly Pro
110                 115                 120                 125

Ser Val Phe Pro Leu Ala Pro Ser Ser Lys Ser Thr Ser Gly Gly Thr
            130                 135                 140

Ala Ala Leu Gly Cys Leu Val Lys Asp Tyr Phe Pro Glu Pro Val Thr
            145                 150                 155

Val Ser Trp Asn Ser Gly Ala Leu Thr Ser Gly Val His Thr Phe Pro
        160                 165                 170

Ala Val Leu Gln Ser Ser Gly Leu Tyr Ser Leu Ser Ser Val Val Thr
    175                 180                 185

Val Pro Ser Ser Ser Leu Gly Thr Gln Thr Tyr Ile Cys Asn Val Asn
190                 195                 200                 205

His Lys Pro Ser Asn Thr Lys Val Asp Lys Lys Val Glu Pro Lys Ser
                210                 215                 220

Cys Asp Lys Thr His Thr Cys Pro Pro Cys Pro Ala Pro Glu Leu Leu
            225                 230                 235

Gly Gly Pro Ser Val Phe Leu Phe Pro Pro Lys Pro Lys Asp Thr Leu
        240                 245                 250

Met Ile Ser Arg Thr Pro Glu Val Thr Cys Val Val Val Asp Val Ser
    255                 260                 265

His Glu Asp Pro Glu Val Lys Phe Asn Trp Tyr Val Asp Gly Val Glu
270                 275                 280                 285

Val His Asn Ala Lys Thr Lys Pro Arg Glu Glu Gln Tyr Asn Ser Thr
                290                 295                 300

Tyr Arg Val Val Ser Val Leu Thr Val Leu His Gln Asp Trp Leu Asn
            305                 310                 315

Gly Lys Glu Tyr Lys Cys Lys Val Ser Asn Lys Ala Leu Pro Ala Pro
        320                 325                 330

Ile Glu Lys Thr Ile Ser Lys Ala Lys Gly Gln Pro Arg Glu Pro Gln
    335                 340                 345

Val Tyr Thr Leu Pro Pro Ser Arg Asp Glu Leu Thr Lys Asn Gln Val
350                 355                 360                 365

Ser Leu Thr Cys Leu Val Lys Gly Phe Tyr Pro Ser Asp Ile Ala Val
            370                 375                 380

Glu Trp Glu Ser Asn Gly Gln Pro Glu Asn Asn Tyr Lys Thr Thr Pro
        385                 390                 395

Pro Val Leu Asp Ser Asp Gly Ser Phe Phe Leu Tyr Ser Lys Leu Thr
    400                 405                 410

Val Asp Lys Ser Arg Trp Gln Gln Gly Asn Val Phe Ser Cys Ser Val
415                 420                 425

Met His Glu Ala Leu His Asn His Tyr Thr Gln Lys Ser Leu Ser Leu
430                 435                 440                 445

Ser Pro Gly Lys

<210> SEQ ID NO 56
<211> LENGTH: 705
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(702)
```

<220> FEATURE:
<221> NAME/KEY: sig_peptide
<222> LOCATION: (1)..(60)
<220> FEATURE:
<221> NAME/KEY: mat_peptide
<222> LOCATION: (61)..(702)

<400> SEQUENCE: 56

```
atg gtt ttc aca cct cag att ctt gga ctt atg ctt ttc tgg att tca        48
Met Val Phe Thr Pro Gln Ile Leu Gly Leu Met Leu Phe Trp Ile Ser
-20             -15                 -10                 -5 gcc tcc aga ggt gat att gtg cta act cag tct cca gcc acc ctg tct        96
Ala Ser Arg Gly Asp Ile Val Leu Thr Gln Ser Pro Ala Thr Leu Ser
         -1  1               5                  10 gtg act cca gga gat aga gtc agt ctt tcc tgc agg gcc agt caa agt       144
Val Thr Pro Gly Asp Arg Val Ser Leu Ser Cys Arg Ala Ser Gln Ser
     15                  20                  25 att agc aac tac cta cac tgg tat caa caa aaa tca cat gag tct cca       192
Ile Ser Asn Tyr Leu His Trp Tyr Gln Gln Lys Ser His Glu Ser Pro
 30                  35                  40 agg ctt ctc atc aag tat gct tcc cag tcc atc tct ggg atc ccc tcc       240
Arg Leu Leu Ile Lys Tyr Ala Ser Gln Ser Ile Ser Gly Ile Pro Ser
45                  50                  55                  60 agg ttc agt ggc agt gga tca ggg aca gat ttc act ctc agt atc aac       288
Arg Phe Ser Gly Ser Gly Ser Gly Thr Asp Phe Thr Leu Ser Ile Asn
                 65                  70                  75 agt gtg gag act gaa gat ttt gga atg tat ttc tgt caa cag agt aac       336
Ser Val Glu Thr Glu Asp Phe Gly Met Tyr Phe Cys Gln Gln Ser Asn
             80                  85                  90 agc tgg ccg ctc acg ttc ggt gct ggg acc aag ctg gag ctg aaa cga       384
Ser Trp Pro Leu Thr Phe Gly Ala Gly Thr Lys Leu Glu Leu Lys Arg
         95                 100                 105 act gtg gct gca cca tct gtc ttc atc ttc ccg cca tct gat gag cag       432
Thr Val Ala Ala Pro Ser Val Phe Ile Phe Pro Pro Ser Asp Glu Gln
    110                 115                 120 ttg aaa tct gga act gcc tct gtt gtg tgc ctg ctg aat aac ttc tat       480
Leu Lys Ser Gly Thr Ala Ser Val Val Cys Leu Leu Asn Asn Phe Tyr
125                 130                 135                 140 ccc aga gag gcc aaa gta cag tgg aag gtg gat aac gcc ctc caa tcg       528
Pro Arg Glu Ala Lys Val Gln Trp Lys Val Asp Asn Ala Leu Gln Ser
                145                 150                 155 ggt aac tcc cag gag agt gtc aca gag cag gac agc aag gac agc acc       576
Gly Asn Ser Gln Glu Ser Val Thr Glu Gln Asp Ser Lys Asp Ser Thr
            160                 165                 170 tac agc ctc agc agc acc ctg acg ctg agc aaa gca gac tac gag aaa       624
Tyr Ser Leu Ser Ser Thr Leu Thr Leu Ser Lys Ala Asp Tyr Glu Lys
        175                 180                 185 cac aaa gtc tac gcc tgc gaa gtc acc cat cag ggc ctg agc tcg ccc       672
His Lys Val Tyr Ala Cys Glu Val Thr His Gln Gly Leu Ser Ser Pro
    190                 195                 200 gtc aca aag agc ttc aac agg gga gag tgc tag                           705
Val Thr Lys Ser Phe Asn Arg Gly Glu Cys
205                 210
```

<210> SEQ ID NO 57
<211> LENGTH: 234
<212> TYPE: PRT
<213> ORGANISM: Artificial Sequence
<220> FEATURE:
<223> OTHER INFORMATION: Description of Artificial Sequence: Synthetic construct

```
<400> SEQUENCE: 57

Met Val Phe Thr Pro Gln Ile Leu Gly Leu Met Leu Phe Trp Ile Ser
-20             -15                 -10                  -5

Ala Ser Arg Gly Asp Ile Val Leu Thr Gln Ser Pro Ala Thr Leu Ser
            -1  1               5                   10

Val Thr Pro Gly Asp Arg Val Ser Leu Ser Cys Arg Ala Ser Gln Ser
            15              20              25

Ile Ser Asn Tyr Leu His Trp Tyr Gln Gln Lys Ser His Glu Ser Pro
30              35                      40

Arg Leu Leu Ile Lys Tyr Ala Ser Gln Ser Ile Ser Gly Ile Pro Ser
45              50                      55                  60

Arg Phe Ser Gly Ser Gly Ser Gly Thr Asp Phe Thr Leu Ser Ile Asn
                65              70                      75

Ser Val Glu Thr Glu Asp Phe Gly Met Tyr Phe Cys Gln Gln Ser Asn
                80              85                  90

Ser Trp Pro Leu Thr Phe Gly Ala Gly Thr Lys Leu Glu Leu Lys Arg
                95              100                 105

Thr Val Ala Ala Pro Ser Val Phe Ile Phe Pro Pro Ser Asp Glu Gln
110                 115                 120

Leu Lys Ser Gly Thr Ala Ser Val Val Cys Leu Leu Asn Asn Phe Tyr
125                 130                 135                 140

Pro Arg Glu Ala Lys Val Gln Trp Lys Val Asp Asn Ala Leu Gln Ser
                145                 150                 155

Gly Asn Ser Gln Glu Ser Val Thr Glu Gln Asp Ser Lys Asp Ser Thr
                160                 165                 170

Tyr Ser Leu Ser Ser Thr Leu Thr Leu Ser Lys Ala Asp Tyr Glu Lys
                175                 180                 185

His Lys Val Tyr Ala Cys Glu Val Thr His Gln Gly Leu Ser Ser Pro
                190                 195                 200

Val Thr Lys Ser Phe Asn Arg Gly Glu Cys
205                 210

<210> SEQ ID NO 58
<211> LENGTH: 6
<212> TYPE: PRT
<213> ORGANISM: Mus musculus
<220> FEATURE:
<221> NAME/KEY: MISC_FEATURE
<222> LOCATION: (1)..(6)
<223> OTHER INFORMATION: CDR

<400> SEQUENCE: 58

Ser Asp Tyr Ala Trp Asn
1               5

<210> SEQ ID NO 59
<211> LENGTH: 17
<212> TYPE: PRT
<213> ORGANISM: Mus musculus
<220> FEATURE:
<221> NAME/KEY: MISC_FEATURE
<222> LOCATION: (1)..(17)
<223> OTHER INFORMATION: CDR

<400> SEQUENCE: 59

Tyr Ile Ser Tyr Ser Gly Ser Thr Ser Tyr Asn Pro Ser Leu Lys Ser
1               5                   10                  15

Arg
```

```
<210> SEQ ID NO 60
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: CDR

<400> SEQUENCE: 60

Ser Pro Pro Tyr Tyr Ala Met Asp Tyr
1               5

<210> SEQ ID NO 61
<211> LENGTH: 11
<212> TYPE: PRT
<213> ORGANISM: Mus musculus
<220> FEATURE:
<221> NAME/KEY: MISC_FEATURE
<222> LOCATION: (1)..(11)
<223> OTHER INFORMATION: CDR

<400> SEQUENCE: 61

Lys Ala Ser Gln Asp Val Gly Thr Ala Val Ala
1               5                   10

<210> SEQ ID NO 62
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: CDR

<400> SEQUENCE: 62

Trp Ala Ser Thr Arg His Thr
1               5

<210> SEQ ID NO 63
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: CDR

<400> SEQUENCE: 63

Gln Gln Tyr Ser Ser Tyr Pro Leu Thr
1               5

<210> SEQ ID NO 64
<211> LENGTH: 5
<212> TYPE: PRT
<213> ORGANISM: Mus musculus
<220> FEATURE:
<221> NAME/KEY: MISC_FEATURE
<222> LOCATION: (1)..(5)
<223> OTHER INFORMATION: CDR

<400> SEQUENCE: 64

Ser Tyr Trp Ile His
1               5

<210> SEQ ID NO 65
<211> LENGTH: 17
<212> TYPE: PRT
<213> ORGANISM: Mus musculus
```

```
<220> FEATURE:
<221> NAME/KEY: MISC_FEATURE
<222> LOCATION: (1)..(17)
<223> OTHER INFORMATION: CDR

<400> SEQUENCE: 65

Arg Ile Tyr Pro Gly Thr Gly Ser Thr Tyr Tyr Asn Glu Lys Phe Lys
1               5                   10                  15
Gly

<210> SEQ ID NO 66
<211> LENGTH: 10
<212> TYPE: PRT
<213> ORGANISM: Mus musculus
<220> FEATURE:
<221> NAME/KEY: MISC_FEATURE
<222> LOCATION: (1)..(10)
<223> OTHER INFORMATION: CDR

<400> SEQUENCE: 66

Tyr Pro Thr Tyr Asp Trp Tyr Phe Asp Val
1               5                   10

<210> SEQ ID NO 67
<211> LENGTH: 11
<212> TYPE: PRT
<213> ORGANISM: Mus musculus
<220> FEATURE:
<221> NAME/KEY: MISC_FEATURE
<222> LOCATION: (1)..(11)
<223> OTHER INFORMATION: CDR

<400> SEQUENCE: 67

Arg Ala Ser Gln Ser Ile Ser Asn Tyr Leu His
1               5                   10

<210> SEQ ID NO 68
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: CDR

<400> SEQUENCE: 68

Tyr Ala Ser Gln Ser Ile Ser
1               5

<210> SEQ ID NO 69
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: CDR

<400> SEQUENCE: 69

Gln Gln Ser Asn Ser Trp Pro Leu Thr
1               5

<210> SEQ ID NO 70
<211> LENGTH: 6
<212> TYPE: PRT
<213> ORGANISM: Mus musculus
```

```
<220> FEATURE:
<221> NAME/KEY: MISC_FEATURE
<222> LOCATION: (1)..(6)
<223> OTHER INFORMATION: CDR

<400> SEQUENCE: 70

Ser Asp Tyr Ala Trp Asn
1               5

<210> SEQ ID NO 71
<211> LENGTH: 17
<212> TYPE: PRT
<213> ORGANISM: Mus musculus
<220> FEATURE:
<221> NAME/KEY: MISC_FEATURE
<222> LOCATION: (1)..(17)
<223> OTHER INFORMATION: CDR

<400> SEQUENCE: 71

Tyr Ile Ser Tyr Ser Gly Ser Thr Ser Tyr Asn Pro Ser Leu Lys Ser
1               5                   10                  15

Arg

<210> SEQ ID NO 72
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: CDR

<400> SEQUENCE: 72

Ala Leu Pro Leu Pro Trp Phe Ala Tyr
1               5

<210> SEQ ID NO 73
<211> LENGTH: 11
<212> TYPE: PRT
<213> ORGANISM: Mus musculus
<220> FEATURE:
<221> NAME/KEY: MISC_FEATURE
<222> LOCATION: (1)..(11)
<223> OTHER INFORMATION: CDR

<400> SEQUENCE: 73

Lys Ala Ser Gln Asp Val Gly Thr Ala Val Ala
1               5                   10

<210> SEQ ID NO 74
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: CDR

<400> SEQUENCE: 74

Trp Ala Ser Thr Arg His Thr
1               5

<210> SEQ ID NO 75
<211> LENGTH: 9
<212> TYPE: PRT
<213> ORGANISM: Mus musculus
```

```
<220> FEATURE:
<221> NAME/KEY: MISC_FEATURE
<222> LOCATION: (1)..(9)
<223> OTHER INFORMATION: CDR

<400> SEQUENCE: 75

Gln Gln Tyr Ser Ser Tyr Pro Tyr Thr
1               5

<210> SEQ ID NO 76
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (2)..(3)
<223> OTHER INFORMATION: Any amino acid

<400> SEQUENCE: 76

Tyr Xaa Xaa Leu
1

<210> SEQ ID NO 77
<211> LENGTH: 462
<212> TYPE: PRT
<213> ORGANISM: Homo sapiens

<400> SEQUENCE: 77

Met Thr Leu Ile Leu Thr Ser Leu Leu Phe Phe Gly Leu Ser Leu Gly
1               5                   10                  15

Pro Arg Thr Arg Val Gln Ala Glu Asn Leu Pro Lys Pro Ile Leu Trp
            20                  25                  30

Ala Glu Pro Gly Pro Val Ile Thr Trp His Asn Pro Val Thr Ile Trp
        35                  40                  45

Cys Gln Gly Thr Leu Glu Ala Gln Gly Tyr Arg Leu Lys Glu Gly Asn
    50                  55                  60

Ser Met Ser Arg His Ile Leu Lys Thr Leu Glu Ser Glu Asn Lys Val
65                  70                  75                  80

Lys Leu Ser Ile Pro Ser Met Met Trp Glu His Ala Gly Arg Tyr His
                85                  90                  95

Cys Tyr Tyr Gln Ser Pro Ala Gly Trp Ser Glu Pro Ser Asp Pro Leu
            100                 105                 110

Glu Leu Val Val Thr Ala Tyr Ser Arg Pro Thr Leu Ser Ala Leu Pro
        115                 120                 125

Ser Pro Val Val Thr Ser Gly Val Asn Val Thr Leu Arg Cys Ala Ser
    130                 135                 140

Arg Leu Gly Leu Gly Arg Phe Thr Leu Ile Glu Glu Gly Asp His Arg
145                 150                 155                 160

Leu Ser Trp Thr Leu Asn Ser His Gln His Asn His Gly Lys Phe Gln
                165                 170                 175

Ala Leu Phe Pro Met Gly Pro Leu Thr Phe Ser Asn Arg Gly Thr Phe
            180                 185                 190

Arg Cys Tyr Gly Tyr Glu Asn Asn Thr Pro Tyr Val Trp Ser Glu Pro
        195                 200                 205

Ser Asp Pro Leu Gln Leu Val Ser Gly Val Ser Arg Lys Pro Ser
    210                 215                 220

Leu Leu Thr Leu Gln Gly Pro Val Val Thr Pro Gly Glu Asn Leu Thr
225                 230                 235                 240
```

```
Leu Gln Cys Gly Ser Asp Val Gly Tyr Ile Arg Tyr Thr Leu Tyr Lys
                245                 250                 255

Glu Gly Ala Asp Gly Leu Pro Gln Pro Gly Arg Gln Pro Gln Ala
    260                 265                 270

Gly Leu Ser Gln Ala Asn Phe Thr Leu Ser Pro Val Ser Arg Ser Tyr
        275                 280                 285

Gly Gly Gln Tyr Arg Cys Tyr Gly Ala His Asn Val Ser Ser Glu Trp
        290                 295                 300

Ser Ala Pro Ser Asp Pro Leu Asp Ile Leu Ile Ala Gly Gln Ile Ser
305                 310                 315                 320

Asp Arg Pro Ser Leu Ser Val Gln Pro Gly Pro Thr Val Thr Ser Gly
                325                 330                 335

Glu Lys Val Thr Leu Leu Cys Gln Ser Trp Asp Pro Met Phe Thr Phe
                340                 345                 350

Leu Leu Thr Lys Glu Gly Ala Ala His Pro Pro Leu Arg Leu Arg Ser
            355                 360                 365

Met Tyr Gly Ala His Lys Tyr Gln Ala Glu Phe Pro Met Ser Pro Val
        370                 375                 380

Thr Ser Ala His Ala Gly Thr Tyr Arg Cys Tyr Gly Ser Arg Ser Ser
385                 390                 395                 400

Asn Pro Tyr Leu Leu Ser His Pro Ser Glu Pro Leu Glu Leu Val Val
                405                 410                 415

Ser Gly Ala Thr Glu Thr Leu Asn Pro Ala Gln Lys Lys Ser Asp Ser
                420                 425                 430

Lys Thr Ala Pro His Leu Gln Asp Tyr Thr Val Glu Asn Leu Ile Arg
                435                 440                 445

Met Gly Val Ala Gly Leu Val Leu Leu Phe Leu Gly Ile Leu
    450                 455                 460

<210> SEQ ID NO 78
<211> LENGTH: 461
<212> TYPE: PRT
<213> ORGANISM: Homo sapiens

<400> SEQUENCE: 78

Met Thr Pro Ala Leu Thr Ala Leu Leu Cys Leu Gly Leu Ser Leu Gly
1               5                   10                  15

Pro Arg Thr Arg Val Gln Ala Gly Pro Phe Pro Lys Pro Thr Leu Trp
                20                  25                  30

Ala Glu Pro Gly Ser Val Ile Ser Trp Gly Ser Pro Val Thr Ile Trp
            35                  40                  45

Cys Gln Gly Ser Leu Glu Ala Gln Glu Tyr Arg Leu Asp Lys Glu Gly
    50                  55                  60

Ser Pro Glu Pro Leu Asp Arg Asn Asn Pro Leu Glu Pro Lys Asn Lys
65                  70                  75                  80

Ala Arg Phe Ser Ile Pro Ser Met Thr Glu His His Ala Gly Arg Tyr
                85                  90                  95

Arg Cys His Tyr Tyr Ser Ser Ala Gly Trp Ser Glu Pro Ser Asp Pro
            100                 105                 110

Leu Glu Leu Val Met Thr Gly Phe Tyr Asn Lys Pro Thr Leu Ser Ala
        115                 120                 125

Leu Pro Ser Pro Val Val Ala Ser Gly Gly Asn Met Thr Leu Arg Cys
    130                 135                 140

Gly Ser Gln Lys Gly Tyr His His Phe Val Leu Met Lys Glu Gly Glu
145                 150                 155                 160
```

-continued

His Gln Leu Pro Arg Thr Leu Asp Ser Gln Gln Leu His Ser Gly Gly
                165                 170                 175

Phe Gln Ala Leu Phe Pro Val Gly Pro Val Asn Pro Ser His Arg Trp
            180                 185                 190

Arg Phe Thr Cys Tyr Tyr Tyr Met Asn Thr Pro Gln Val Trp Ser
        195                 200                 205

His Pro Ser Asp Pro Leu Glu Ile Leu Pro Ser Gly Val Ser Arg Lys
    210                 215                 220

Pro Ser Leu Leu Thr Leu Gln Gly Pro Val Leu Ala Pro Gly Gln Ser
225                 230                 235                 240

Leu Thr Leu Gln Cys Gly Ser Asp Val Gly Tyr Asp Arg Phe Val Leu
                245                 250                 255

Tyr Lys Glu Gly Glu Arg Asp Phe Leu Gln Arg Pro Gly Gln Gln Pro
            260                 265                 270

Gln Ala Gly Leu Ser Gln Ala Asn Phe Thr Leu Gly Pro Val Ser Pro
        275                 280                 285

Ser His Gly Gly Gln Tyr Arg Cys Tyr Gly Ala His Asn Leu Ser Ser
    290                 295                 300

Glu Trp Ser Ala Pro Ser Asp Pro Leu Asn Ile Leu Met Ala Gly Gln
305                 310                 315                 320

Ile Tyr Asp Thr Val Ser Leu Ser Ala Gln Pro Gly Pro Thr Val Ala
                325                 330                 335

Ser Gly Glu Asn Val Thr Leu Leu Cys Gln Ser Trp Trp Gln Phe Asp
            340                 345                 350

Thr Phe Leu Leu Thr Lys Glu Gly Ala Ala His Pro Pro Leu Arg Leu
        355                 360                 365

Arg Ser Met Tyr Gly Ala His Lys Tyr Gln Ala Glu Phe Pro Met Ser
    370                 375                 380

Pro Val Thr Ser Ala His Ala Gly Thr Tyr Arg Cys Tyr Gly Ser Tyr
385                 390                 395                 400

Ser Ser Asn Pro His Leu Leu Ser Phe Pro Ser Glu Pro Leu Glu Leu
                405                 410                 415

Met Val Ser Gly His Ser Gly Ser Ser Leu Pro Pro Thr Gly Pro
            420                 425                 430

Pro Ser Thr Pro Gly Leu Gly Arg Tyr Leu Glu Val Leu Ile Gly Val
        435                 440                 445

Ser Val Ala Phe Val Leu Leu Leu Phe Leu Leu Leu Phe
    450                 455                 460

<210> SEQ ID NO 79
<211> LENGTH: 447
<212> TYPE: PRT
<213> ORGANISM: Homo sapiens

<400> SEQUENCE: 79

Met Thr Pro Ile Leu Thr Val Leu Ile Cys Leu Gly Leu Ser Leu Gly
1               5                   10                  15

Pro Arg Thr His Val Gln Ala Gly Pro Phe Pro Lys Pro Thr Leu Trp
            20                  25                  30

Ala Glu Pro Gly Ser Val Ile Ser Trp Gly Ser Pro Val Thr Ile Trp
        35                  40                  45

Cys Gln Gly Ser Leu Glu Ala Gln Glu Tyr Arg Leu Asp Lys Glu Gly
    50                  55                  60

Ser Pro Glu Pro Trp Asp Arg Asn Asn Pro Leu Glu Pro Lys Asn Lys
65                  70                  75                  80

```
Ala Arg Phe Ser Ile Pro Ser Ile Thr Glu His His Ala Gly Arg Tyr
                85                  90                  95
Arg Cys His Tyr Tyr Ser Ser Ala Gly Trp Ser Glu Pro Ser Asp Ala
            100                 105                 110
Leu Glu Leu Val Met Thr Gly Ala Tyr Ser Lys Pro Thr Leu Ser Ala
        115                 120                 125
Leu Pro Ser Pro Val Val Ala Ser Gly Gly Asn Met Thr Leu Gln Cys
    130                 135                 140
Gly Ser Gln Lys Gly Tyr His Gln Phe Val Leu Met Lys Glu Gly Glu
145                 150                 155                 160
His Gln Leu Pro Arg Thr Leu Asp Ser Gln Gln Leu His Ser Gly Gly
                165                 170                 175
Phe Gln Ala Leu Phe Pro Val Gly Pro Val Asn Pro Ser His Arg Trp
            180                 185                 190
Arg Phe Thr Cys Tyr Tyr Tyr Met Asn Thr Pro Arg Val Trp Ser
        195                 200                 205
His Pro Ser Asp Pro Leu Glu Ile Leu Pro Ser Gly Val Ser Arg Lys
    210                 215                 220
Pro Ser Leu Leu Thr Leu Gln Gly Pro Val Leu Ala Pro Gly Gln Ser
225                 230                 235                 240
Leu Thr Leu Gln Cys Gly Ser Asp Val Gly Tyr Asp Arg Phe Val Leu
                245                 250                 255
Tyr Lys Glu Gly Glu Arg Asp Phe Leu Gln Arg Pro Gly Gln Gln Pro
            260                 265                 270
Gln Ala Gly Leu Ser Gln Ala Asn Phe Thr Leu Gly Pro Val Ser Pro
        275                 280                 285
Ser His Gly Gly Gln Tyr Arg Cys Tyr Gly Ala His Asn Leu Ser Ser
    290                 295                 300
Glu Trp Ser Ala Pro Ser Asp Pro Leu Asn Ile Leu Met Ala Gly Gln
305                 310                 315                 320
Ile Tyr Asp Thr Val Ser Leu Ser Ala Gln Pro Gly Pro Thr Val Ala
                325                 330                 335
Ser Gly Glu Asn Val Thr Leu Leu Cys Gln Ser Trp Trp Gln Phe Asp
            340                 345                 350
Thr Phe Leu Leu Thr Lys Glu Gly Ala Ala His Pro Pro Leu Arg Leu
        355                 360                 365
Arg Ser Met Tyr Gly Ala His Lys Tyr Gln Ala Glu Phe Pro Met Ser
    370                 375                 380
Pro Val Thr Ser Ala His Ala Gly Thr Tyr Arg Cys Tyr Gly Ser Tyr
385                 390                 395                 400
Ser Ser Asn Pro His Leu Leu Ser Phe Pro Ser Glu Pro Leu Glu Leu
                405                 410                 415
Met Val Ser Ala Ser His Ala Lys Asp Tyr Thr Val Glu Asn Leu Ile
            420                 425                 430
Arg Met Gly Met Ala Gly Leu Val Leu Val Phe Leu Gly Ile Leu
        435                 440                 445

<210> SEQ ID NO 80
<211> LENGTH: 478
<212> TYPE: PRT
<213> ORGANISM: Homo sapiens
```

<400> SEQUENCE: 80

```
Met Thr Pro Ile Val Thr Val Leu Ile Cys Leu Arg Leu Ser Leu Gly
1               5                   10                  15

Pro Arg Thr His Val Gln Ala Gly Thr Leu Pro Lys Pro Thr Leu Trp
            20                  25                  30

Ala Glu Pro Gly Ser Val Ile Thr Gln Gly Ser Pro Val Thr Leu Trp
            35                  40                  45

Cys Gln Gly Ile Leu Glu Thr Gln Glu Tyr Arg Leu Tyr Arg Glu Lys
    50                  55                  60

Lys Thr Ala Pro Trp Ile Thr Arg Ile Pro Gln Glu Ile Val Lys Lys
65                  70                  75                  80

Gly Gln Phe Pro Ile Pro Ser Ile Thr Trp Glu His Thr Gly Arg Tyr
                85                  90                  95

Arg Cys Phe Tyr Gly Ser His Thr Ala Gly Trp Ser Glu Pro Ser Asp
            100                 105                 110

Pro Leu Glu Leu Val Val Thr Gly Ala Tyr Ile Lys Pro Thr Leu Ser
            115                 120                 125

Ala Leu Pro Ser Pro Val Thr Ser Gly Gly Asn Val Thr Leu His
130                 135                 140

Cys Val Ser Gln Val Ala Phe Gly Ser Phe Ile Leu Cys Lys Glu Gly
145                 150                 155                 160

Glu Asp Glu His Pro Gln Cys Leu Asn Ser Gln Pro Arg Thr His Gly
                165                 170                 175

Trp Ser Arg Ala Ile Phe Ser Val Gly Pro Val Ser Pro Ser Arg Arg
            180                 185                 190

Trp Ser Tyr Arg Cys Tyr Ala Tyr Asp Ser Asn Ser Pro His Val Trp
            195                 200                 205

Ser Leu Pro Ser Asp Leu Leu Glu Leu Leu Val Leu Gly Val Ser Lys
210                 215                 220

Lys Pro Ser Leu Ser Val Gln Pro Gly Pro Ile Val Ala Pro Gly Glu
225                 230                 235                 240

Ser Leu Thr Leu Gln Cys Val Ser Asp Val Ser Tyr Asp Arg Phe Val
            245                 250                 255

Leu Tyr Lys Glu Gly Glu Arg Asp Phe Leu Gln Leu Pro Gly Pro Gln
            260                 265                 270

Pro Gln Ala Gly Leu Ser Gln Ala Asn Phe Thr Leu Gly Pro Val Ser
            275                 280                 285

Arg Ser Tyr Gly Gly Gln Tyr Arg Cys Ser Gly Ala Tyr Asn Leu Ser
            290                 295                 300

Ser Glu Trp Ser Ala Pro Ser Asp Pro Leu Asp Ile Leu Ile Ala Gly
305                 310                 315                 320

Gln Phe Arg Gly Arg Pro Phe Ile Ser Val His Pro Gly Pro Thr Val
            325                 330                 335

Ala Ser Gly Glu Asn Val Thr Leu Leu Cys Gln Ser Trp Gly Pro Phe
            340                 345                 350

His Thr Phe Leu Leu Thr Lys Ala Gly Ala Ala Asp Ala Pro Leu Arg
            355                 360                 365

Leu Arg Ser Ile His Glu Tyr Pro Lys Tyr Gln Ala Glu Phe Pro Met
            370                 375                 380

Ser Pro Val Thr Ser Ala His Ser Gly Thr Tyr Arg Cys Tyr Gly Ser
385                 390                 395                 400

Leu Ser Ser Asn Pro Tyr Leu Leu Ser His Pro Ser Asp Ser Leu Glu
            405                 410                 415
```

```
Leu Met Val Ser Gly Ala Ala Glu Thr Leu Ser Pro Pro Gln Asn Lys
            420                 425                 430

Ser Asp Ser Lys Ala Gly Ala Ala Asn Thr Leu Ser Pro Ser Gln Asn
        435                 440                 445

Lys Thr Ala Ser His Pro Gln Asp Tyr Thr Val Glu Asn Leu Ile Arg
450                 455                 460

Met Gly Ile Ala Gly Leu Val Leu Val Val Leu Gly Ile Leu
465                 470                 475

<210> SEQ ID NO 81
<211> LENGTH: 449
<212> TYPE: PRT
<213> ORGANISM: Homo sapiens

<400> SEQUENCE: 81

Met Thr Pro Ile Leu Thr Val Leu Ile Cys Leu Gly Leu Ser Leu Gly
1               5                   10                  15

Pro Arg Thr His Val Gln Ala Gly His Leu Pro Lys Pro Thr Leu Trp
            20                  25                  30

Ala Glu Pro Gly Ser Val Ile Ile Gln Gly Ser Pro Val Thr Leu Arg
        35                  40                  45

Cys Gln Gly Ser Leu Gln Ala Glu Glu Tyr His Leu Tyr Arg Glu Asn
    50                  55                  60

Lys Ser Ala Ser Trp Val Arg Arg Ile Gln Glu Pro Gly Lys Asn Gly
65                  70                  75                  80

Gln Phe Pro Ile Pro Ser Ile Thr Trp Glu His Ala Gly Arg Tyr His
                85                  90                  95

Cys Gln Tyr Tyr Ser His Asn His Ser Ser Glu Tyr Ser Asp Pro Leu
            100                 105                 110

Glu Leu Val Val Thr Gly Ala Tyr Ser Lys Pro Thr Leu Ser Ala Leu
        115                 120                 125

Pro Ser Pro Val Val Thr Leu Gly Gly Asn Val Thr Leu Gln Cys Val
    130                 135                 140

Ser Gln Val Ala Phe Asp Gly Phe Ile Leu Cys Lys Glu Gly Glu Asp
145                 150                 155                 160

Glu His Pro Gln Arg Leu Asn Ser His Ser His Ala Arg Gly Trp Ser
                165                 170                 175

Trp Ala Ile Phe Ser Val Gly Pro Val Ser Pro Ser Arg Arg Trp Ser
            180                 185                 190

Tyr Arg Cys Tyr Ala Tyr Asp Ser Asn Ser Pro Tyr Val Trp Ser Leu
        195                 200                 205

Pro Ser Asp Leu Leu Glu Leu Leu Val Pro Gly Val Ser Lys Lys Pro
    210                 215                 220

Ser Leu Ser Val Gln Pro Gly Pro Met Val Ala Pro Gly Glu Ser Leu
225                 230                 235                 240

Thr Leu Gln Cys Val Ser Asp Val Gly Tyr Asp Arg Phe Val Leu Tyr
                245                 250                 255

Lys Glu Gly Glu Arg Asp Phe Leu Gln Arg Pro Gly Trp Gln Pro Gln
            260                 265                 270

Ala Gly Leu Ser Gln Ala Asn Phe Thr Leu Gly Pro Val Ser Pro Ser
        275                 280                 285

His Gly Gly Gln Tyr Arg Cys Tyr Ser Ala His Asn Leu Ser Ser Glu
    290                 295                 300

Trp Ser Ala Pro Ser Asp Pro Leu Asp Ile Leu Ile Thr Gly Gln Phe
305                 310                 315                 320
```

-continued

```
Tyr Asp Arg Pro Ser Leu Ser Val Gln Pro Val Thr Val Ala Pro
                325                 330                 335

Gly Lys Asn Val Thr Leu Leu Cys Gln Ser Arg Gly Gln Phe His Thr
                340                 345                 350

Phe Leu Leu Thr Lys Glu Gly Ala Gly His Pro Pro Leu His Leu Arg
                355                 360                 365

Ser Glu His Gln Ala Gln Gln Asn Gln Ala Glu Phe Arg Met Gly Pro
            370                 375                 380

Val Thr Ser Ala His Val Gly Thr Tyr Arg Cys Tyr Ser Ser Leu Ser
385                 390                 395                 400

Ser Asn Pro Tyr Leu Leu Ser Leu Pro Ser Asp Pro Leu Glu Leu Val
                405                 410                 415

Val Ser Ala Ser Leu Gly Gln His Pro Gln Asp Tyr Thr Val Glu Asn
            420                 425                 430

Leu Ile Arg Met Gly Val Ala Gly Leu Val Leu Val Val Leu Gly Ile
                435                 440                 445

Leu
```

<210> SEQ ID NO 82
<211> LENGTH: 439
<212> TYPE: PRT
<213> ORGANISM: Homo sapiens

<400> SEQUENCE: 82

```
Met Thr Ser Ile Leu Thr Val Leu Ile Cys Leu Gly Leu Ser Leu Asp
1               5                   10                  15

Pro Arg Thr His Val Gln Ala Gly Pro Leu Pro Lys Pro Thr Leu Trp
                20                  25                  30

Ala Glu Pro Gly Ser Val Ile Thr Gln Gly Ser Pro Val Thr Leu Arg
            35                  40                  45

Cys Gln Gly Ser Leu Glu Thr Gln Glu Tyr His Leu Tyr Arg Glu Lys
        50                  55                  60

Lys Thr Ala Leu Trp Ile Thr Arg Ile Pro Gln Glu Leu Val Lys Lys
65                  70                  75                  80

Gly Gln Phe Pro Ile Leu Ser Ile Thr Trp Glu His Ala Gly Arg Tyr
                85                  90                  95

Cys Cys Ile Tyr Gly Ser His Thr Val Gly Leu Ser Glu Ser Ser Asp
            100                 105                 110

Pro Leu Glu Leu Val Val Thr Gly Ala Tyr Ser Lys Pro Thr Leu Ser
        115                 120                 125

Ala Leu Pro Ser Pro Val Val Thr Ser Gly Gly Asn Val Thr Ile Gln
    130                 135                 140

Cys Asp Ser Gln Val Ala Phe Asp Gly Phe Ile Leu Cys Lys Glu Gly
145                 150                 155                 160

Glu Asp Glu His Pro Gln Cys Leu Asn Ser His Ser His Ala Arg Gly
                165                 170                 175

Ser Ser Arg Ala Ile Phe Ser Val Gly Pro Val Ser Pro Ser Arg Arg
            180                 185                 190

Trp Ser Tyr Arg Cys Tyr Gly Tyr Asp Ser Arg Ala Pro Tyr Val Trp
        195                 200                 205

Ser Leu Pro Ser Asp Leu Leu Gly Leu Leu Val Pro Gly Val Ser Lys
    210                 215                 220

Lys Pro Ser Leu Ser Val Gln Pro Gly Pro Val Val Ala Pro Gly Glu
225                 230                 235                 240
```

-continued

```
Lys Leu Thr Phe Gln Cys Gly Ser Asp Ala Gly Tyr Asp Arg Phe Val
                245                 250                 255

Leu Tyr Lys Glu Trp Gly Arg Asp Phe Leu Gln Arg Pro Gly Arg Gln
            260                 265                 270

Pro Gln Ala Gly Leu Ser Gln Ala Asn Phe Thr Leu Gly Pro Val Ser
        275                 280                 285

Arg Ser Tyr Gly Gly Gln Tyr Thr Cys Ser Gly Ala Tyr Asn Leu Ser
    290                 295                 300

Ser Glu Trp Ser Ala Pro Ser Asp Pro Leu Asp Ile Leu Ile Thr Gly
305                 310                 315                 320

Gln Ile Arg Ala Arg Pro Phe Leu Ser Val Arg Pro Gly Pro Thr Val
                325                 330                 335

Ala Ser Gly Glu Asn Val Thr Leu Leu Cys Gln Ser Gln Gly Gly Met
            340                 345                 350

His Thr Phe Leu Leu Thr Lys Glu Gly Ala Ala Asp Ser Pro Leu Arg
        355                 360                 365

Leu Lys Ser Lys Arg Gln Ser His Lys Tyr Gln Ala Glu Phe Pro Met
    370                 375                 380

Ser Pro Val Thr Ser Ala His Ala Gly Thr Tyr Arg Cys Tyr Gly Ser
385                 390                 395                 400

Leu Ser Ser Asn Pro Tyr Leu Leu Thr His Pro Ser Asp Pro Leu Glu
                405                 410                 415

Leu Val Val Ser Gly Ala Ala Glu Thr Leu Ser Pro Pro Gln Asn Lys
            420                 425                 430

Ser Asp Ser Lys Ala Gly Glu
        435

<210> SEQ ID NO 83
<211> LENGTH: 478
<212> TYPE: PRT
<213> ORGANISM: Homo sapiens

<400> SEQUENCE: 83

Met Thr Pro Ile Leu Thr Val Leu Ile Cys Leu Gly Leu Ser Leu Gly
1               5                   10                  15

Pro Arg Thr His Val Gln Ala Gly His Leu Pro Lys Pro Thr Leu Trp
            20                  25                  30

Ala Glu Pro Gly Ser Val Ile Thr Gln Gly Ser Pro Val Thr Leu Arg
        35                  40                  45

Cys Gln Gly Gly Gln Glu Thr Gln Glu Tyr Arg Leu Tyr Arg Glu Lys
    50                  55                  60

Lys Thr Ala Pro Trp Ile Thr Arg Ile Pro Gln Glu Leu Val Lys Lys
65                  70                  75                  80

Gly Gln Phe Phe Ile Pro Ser Ile Thr Trp Glu His Ala Gly Arg Tyr
                85                  90                  95

Arg Cys Tyr Tyr Gly Ser Asp Thr Ala Gly Arg Ser Glu Ser Ser Asp
            100                 105                 110

Pro Leu Glu Leu Val Val Thr Gly Ala Tyr Ile Lys Pro Thr Leu Ser
        115                 120                 125

Ala Gln Pro Ser Pro Val Val Asn Ser Gly Gly Asn Val Thr Leu Gln
    130                 135                 140

Cys Asp Ser Gln Val Ala Phe Asp Gly Phe Ile Leu Cys Lys Glu Gly
145                 150                 155                 160

Glu Asp Gly His Pro Gln Cys Leu Asn Ser Gln Pro His Ala Arg Gly
                165                 170                 175
```

```
Ser Ser Arg Ala Ile Phe Ser Val Gly Pro Val Ser Pro Ser Arg Arg
            180                 185                 190

Trp Trp Tyr Arg Cys Tyr Ala Tyr Asp Ser Asn Ser Pro Tyr Glu Trp
            195                 200                 205

Ser Leu Pro Ser Asp Leu Leu Glu Leu Leu Val Leu Gly Val Ser Lys
    210                 215                 220

Lys Pro Ser Leu Ser Val Gln Pro Gly Pro Ile Val Ala Pro Glu Glu
225                 230                 235                 240

Thr Leu Thr Leu Gln Cys Gly Ser Asp Ala Gly Tyr Asn Arg Phe Val
                245                 250                 255

Leu Tyr Lys Asp Gly Glu Arg Asp Phe Leu Gln Leu Ala Gly Ala Gln
                260                 265                 270

Pro Gln Ala Gly Leu Ser Gln Ala Asn Phe Thr Leu Gly Pro Val Ser
            275                 280                 285

Arg Ser Tyr Gly Gly Gln Tyr Arg Cys Tyr Gly Ala His Asn Leu Ser
    290                 295                 300

Ser Glu Trp Ser Ala Pro Ser Asp Pro Leu Asp Ile Leu Ile Ala Gly
305                 310                 315                 320

Gln Phe Tyr Asp Arg Val Ser Leu Ser Val Gln Pro Gly Pro Thr Val
                325                 330                 335

Ala Ser Gly Glu Asn Val Thr Leu Leu Cys Gln Ser Gln Gly Trp Met
                340                 345                 350

Gln Thr Phe Leu Leu Thr Lys Glu Gly Ala Ala Asp Asp Pro Trp Arg
            355                 360                 365

Leu Arg Ser Thr Tyr Gln Ser Gln Lys Tyr Gln Ala Glu Phe Pro Met
    370                 375                 380

Gly Pro Val Thr Ser Ala His Ala Gly Thr Tyr Arg Cys Tyr Gly Ser
385                 390                 395                 400

Gln Ser Ser Lys Pro Tyr Leu Leu Thr His Pro Ser Asp Pro Leu Glu
                405                 410                 415

Leu Val Val Ser Gly Pro Ser Gly Gly Pro Ser Ser Pro Thr Thr Gly
                420                 425                 430

Pro Thr Ser Thr Ser Gly Pro Glu Asp Gln Pro Leu Thr Pro Thr Gly
            435                 440                 445

Ser Asp Pro Gln Ser Gly Leu Gly Arg His Leu Gly Val Val Ile Gly
    450                 455                 460

Ile Leu Val Ala Val Ile Leu Leu Leu Leu Leu Leu Leu
465                 470                 475

<210> SEQ ID NO 84
<211> LENGTH: 478
<212> TYPE: PRT
<213> ORGANISM: Homo sapiens

<400> SEQUENCE: 84

Met Thr Pro Ile Val Thr Val Leu Ile Cys Leu Gly Leu Ser Leu Gly
1               5                   10                  15

Pro Arg Thr His Val Gln Thr Gln Thr Ile Pro Lys Pro Thr Leu Trp
            20                  25                  30

Ala Glu Pro Asp Ser Val Ile Thr Gln Gly Ser Pro Val Thr Leu Ser
            35                  40                  45

Cys Gln Gly Ser Leu Glu Ala Gln Glu Tyr Arg Leu Tyr Arg Glu Lys
    50                  55                  60

Lys Ser Ala Ser Trp Ile Thr Arg Ile Arg Pro Glu Leu Val Lys Asn
65                  70                  75                  80
```

```
Gly Gln Phe His Ile Pro Ser Ile Thr Trp Glu His Thr Gly Arg Tyr
                    85                  90                  95
Gly Cys Gln Tyr Tyr Ser Arg Ala Arg Trp Ser Glu Leu Ser Asp Pro
                100                 105                 110
Leu Val Leu Val Met Thr Gly Ala Tyr Pro Lys Pro Thr Leu Ser Ala
                115                 120                 125
Gln Pro Ser Pro Val Val Thr Ser Gly Gly Arg Val Thr Leu Gln Cys
            130                 135                 140
Glu Ser Gln Val Ala Phe Gly Gly Phe Ile Leu Cys Lys Glu Gly Glu
145                 150                 155                 160
Asp Glu His Pro Gln Cys Leu Asn Ser Gln Pro His Ala Arg Gly Ser
                165                 170                 175
Ser Arg Ala Ile Phe Ser Val Gly Pro Val Ser Pro Asn Arg Arg Trp
                180                 185                 190
Ser His Arg Cys Tyr Gly Tyr Asp Leu Asn Ser Pro Tyr Val Trp Ser
                195                 200                 205
Ser Pro Ser Asp Leu Leu Glu Leu Leu Val Pro Gly Val Ser Lys Lys
                210                 215                 220
Pro Ser Leu Ser Val Gln Pro Gly Pro Val Val Ala Pro Gly Glu Ser
225                 230                 235                 240
Leu Thr Leu Gln Cys Val Ser Asp Val Gly Tyr Asp Arg Phe Val Leu
                245                 250                 255
Tyr Lys Glu Gly Glu Arg Asp Leu Arg Gln Leu Pro Gly Arg Gln Pro
                260                 265                 270
Gln Ala Gly Leu Ser Gln Ala Asn Phe Thr Leu Gly Pro Val Ser Arg
                275                 280                 285
Ser Tyr Gly Gly Gln Tyr Arg Cys Tyr Gly Ala Tyr Asn Leu Ser Ser
                290                 295                 300
Glu Trp Ser Ala Pro Ser Asp Pro Leu Asp Ile Leu Ile Thr Gly Gln
305                 310                 315                 320
Ile His Gly Thr Pro Phe Ile Ser Val Gln Pro Gly Pro Thr Val Ala
                325                 330                 335
Ser Gly Glu Asn Val Thr Leu Leu Cys Gln Ser Trp Arg Gln Phe His
                340                 345                 350
Thr Phe Leu Leu Thr Lys Ala Gly Ala Ala Asp Ala Pro Leu Arg Leu
                355                 360                 365
Arg Ser Ile His Glu Tyr Pro Lys Tyr Gln Ala Glu Phe Pro Met Ser
                370                 375                 380
Pro Val Thr Ser Ala His Ala Gly Thr Tyr Arg Cys Tyr Gly Ser Leu
385                 390                 395                 400
Asn Ser Asp Pro Tyr Leu Leu Ser His Pro Ser Glu Pro Leu Glu Leu
                405                 410                 415
Val Val Ser Gly Pro Ser Met Gly Ser Ser Pro Pro Thr Gly Pro
                420                 425                 430
Ile Ser Thr Pro Ala Gly Pro Glu Asp Gln Pro Leu Thr Pro Thr Gly
                435                 440                 445
Ser Asp Pro Gln Ser Gly Leu Gly Arg His Leu Gly Val Val Ile Gly
                450                 455                 460
Ile Leu Val Ala Val Val Leu Leu Leu Leu Leu Leu Leu
465                 470                 475

<210> SEQ ID NO 85
<211> LENGTH: 476
<212> TYPE: PRT
<213> ORGANISM: Homo sapiens
```

-continued

```
<400> SEQUENCE: 85

Met Thr Leu Thr Leu Ser Val Leu Ile Cys Leu Gly Leu Ser Val Gly
1               5                   10                  15

Pro Arg Thr Cys Val Gln Ala Gly Thr Leu Pro Lys Pro Thr Leu Trp
            20                  25                  30

Ala Glu Pro Ala Ser Val Ile Ala Arg Gly Lys Pro Val Thr Leu Trp
        35                  40                  45

Cys Gln Gly Pro Leu Glu Thr Glu Glu Tyr Arg Leu Asp Lys Glu Gly
    50                  55                  60

Leu Pro Trp Ala Arg Lys Arg Gln Asn Pro Leu Glu Pro Gly Ala Lys
65                  70                  75                  80

Ala Lys Phe His Ile Pro Ser Thr Val Tyr Asp Ser Ala Gly Arg Tyr
                85                  90                  95

Arg Cys Tyr Tyr Glu Thr Pro Ala Gly Trp Ser Glu Pro Ser Asp Pro
            100                 105                 110

Leu Glu Leu Val Ala Thr Gly Phe Tyr Ala Glu Pro Thr Leu Leu Ala
        115                 120                 125

Leu Pro Ser Pro Val Val Ala Ser Gly Gly Asn Val Thr Leu Gln Cys
130                 135                 140

Asp Thr Leu Asp Gly Leu Leu Thr Phe Val Leu Val Glu Glu Glu Gln
145                 150                 155                 160

Lys Leu Pro Arg Thr Leu Tyr Ser Gln Lys Leu Pro Lys Gly Pro Ser
                165                 170                 175

Gln Ala Leu Phe Pro Val Gly Pro Val Thr Pro Ser Cys Arg Trp Arg
            180                 185                 190

Phe Arg Cys Tyr Tyr Tyr Arg Lys Asn Pro Gln Val Trp Ser Asn
        195                 200                 205

Pro Ser Asp Leu Leu Glu Ile Leu Val Pro Gly Val Ser Arg Lys Pro
210                 215                 220

Ser Leu Leu Ile Pro Gln Gly Ser Val Val Ala Arg Gly Gly Ser Leu
225                 230                 235                 240

Thr Leu Gln Cys Arg Ser Asp Val Gly Tyr Asp Ile Phe Val Leu Tyr
                245                 250                 255

Lys Glu Gly Glu His Asp Leu Val Gln Gly Ser Gly Gln Gln Pro Gln
            260                 265                 270

Ala Gly Leu Ser Gln Ala Asn Phe Thr Leu Gly Pro Val Ser Arg Ser
        275                 280                 285

His Gly Gly Gln Tyr Arg Cys Tyr Gly Ala His Asn Leu Ser Pro Arg
290                 295                 300

Trp Ser Ala Pro Ser Asp Pro Leu Asp Ile Leu Ile Ala Gly Leu Ile
305                 310                 315                 320

Pro Asp Ile Pro Ala Leu Ser Val Gln Pro Gly Pro Lys Val Ala Ser
                325                 330                 335

Gly Glu Asn Val Thr Leu Leu Cys Gln Ser Trp His Gln Ile Asp Thr
            340                 345                 350

Phe Phe Leu Thr Lys Glu Gly Ala Ala His Pro Pro Leu Cys Leu Lys
        355                 360                 365

Ser Lys Tyr Gln Ser Tyr Arg His Gln Ala Glu Phe Ser Met Ser Pro
370                 375                 380

Val Thr Ser Ala Gln Gly Gly Thr Tyr Arg Cys Tyr Ser Ala Ile Arg
385                 390                 395                 400

Ser Tyr Pro Tyr Leu Leu Ser Ser Pro Ser Tyr Pro Gln Glu Leu Val
                405                 410                 415
```

```
Val Ser Gly Pro Ser Gly Asp Pro Ser Leu Ser Pro Thr Gly Ser Thr
            420                 425                 430

Pro Thr Pro Gly Pro Glu Asp Gln Pro Leu Thr Pro Thr Gly Leu Asp
            435                 440                 445

Pro Gln Ser Gly Leu Gly Arg His Leu Gly Val Val Thr Gly Val Ser
            450                 455                 460

Val Ala Phe Val Leu Leu Leu Phe Leu Leu Leu Phe
465                 470                 475

<210> SEQ ID NO 86
<211> LENGTH: 416
<212> TYPE: PRT
<213> ORGANISM: Homo sapiens

<400> SEQUENCE: 86

Met Ile Pro Thr Phe Thr Ala Leu Leu Cys Leu Gly Leu Ser Leu Gly
1               5                   10                  15

Pro Arg Thr Asp Met Gln Ala Gly Pro Leu Pro Lys Pro Thr Leu Trp
            20                  25                  30

Ala Glu Pro Gly Ser Val Ile Ser Trp Gly Asn Ser Val Thr Ile Trp
        35                  40                  45

Cys Gln Gly Thr Leu Glu Ala Arg Glu Tyr Arg Leu Asp Lys Glu Glu
    50                  55                  60

Ser Pro Ala Pro Trp Asp Arg Gln Asn Pro Leu Glu Pro Lys Asn Lys
65                  70                  75                  80

Ala Arg Phe Ser Ile Pro Ser Met Thr Glu Asp Tyr Ala Gly Arg Tyr
                85                  90                  95

Arg Cys Tyr Tyr Arg Ser Pro Val Gly Trp Ser Gln Pro Ser Asp Pro
            100                 105                 110

Leu Glu Leu Val Met Thr Gly Ala Tyr Ser Lys Pro Thr Leu Ser Ala
        115                 120                 125

Leu Pro Ser Pro Leu Val Thr Ser Gly Lys Ser Val Thr Leu Leu Cys
    130                 135                 140

Gln Ser Arg Ser Pro Met Asp Thr Phe Leu Leu Ile Lys Glu Arg Ala
145                 150                 155                 160

Ala His Pro Leu Leu His Leu Arg Ser Glu His Gly Ala Gln Gln His
                165                 170                 175

Gln Ala Glu Phe Pro Met Ser Pro Val Thr Ser Val His Gly Gly Thr
            180                 185                 190

Tyr Arg Cys Phe Ser Ser His Gly Phe Ser His Tyr Leu Leu Ser His
        195                 200                 205

Pro Ser Asp Pro Leu Glu Leu Ile Val Ser Gly Ser Leu Glu Gly Pro
    210                 215                 220

Arg Pro Ser Pro Thr Arg Ser Val Ser Thr Ala Ala Gly Pro Glu Asp
225                 230                 235                 240

Gln Pro Leu Met Pro Thr Gly Ser Val Pro His Ser Gly Leu Arg Arg
                245                 250                 255

His Trp Glu Val Leu Ile Gly Val Leu Val Val Ser Ile Leu Leu Leu
            260                 265                 270

Ser Leu Leu Leu Phe Leu Leu Leu Gln His Trp Arg Gln Gly Lys His
        275                 280                 285

Arg Thr Leu Ala Gln Arg Gln Ala Asp Phe Gln Arg Pro Pro Gly Ala
    290                 295                 300

Ala Glu Pro Glu Pro Lys Asp Gly Gly Leu Gln Arg Arg Ser Ser Pro
305                 310                 315                 320
```

-continued

```
Ala Ala Asp Val Gln Gly Glu Asn Phe Cys Ala Ala Val Lys Asn Thr
            325                 330                 335

Gln Pro Glu Asp Gly Val Glu Met Asp Thr Arg Gln Ser Pro His Asp
            340                 345                 350

Glu Asp Pro Gln Ala Val Thr Tyr Ala Lys Val Lys His Ser Arg Pro
        355                 360                 365

Arg Arg Glu Met Ala Ser Pro Pro Ser Pro Leu Ser Gly Glu Phe Leu
        370                 375                 380

Asp Thr Lys Asp Arg Gln Ala Glu Glu Asp Arg Gln Met Asp Thr Glu
385                 390                 395                 400

Ala Ala Ala Ser Glu Ala Pro Gln Asp Val Thr Tyr Ala Arg Leu His
                405                 410                 415
```

ANTI-ILT7 ANTIBODY

CROSS-REFERENCE TO RELATED APPLICATIONS

This application is a divisional of U.S. application Ser. No. 12/064,957 filed on Apr. 25, 2008, said U.S. application Ser. No. 12/064,957 claims benefit under 35 U.S.C. §365(c) of International Application No. PCT/JP2006/325391, filed Dec. 20, 2006, said International Application No. PCT/JP2006/325391 claims benefit under 35 U.S.C. §119(b) of Japanese Patent Application No. 2005-366465, filed Dec. 20, 2005. Each of the above listed applications is incorporated by reference herein in its entirety for all purposes.

REFERENCE TO THE SEQUENCE LISTING

This application incorporates by reference a Sequence Listing submitted with this application as text file entitled MED251US.txt created on Apr. 18, 2011 and having a size of 152,917 kilobytes.

TECHNICAL FIELD

The present invention relates to an antibody which binds to human ILT7.

BACKGROUND ART

Interferon α (IFNα: hereinafter, "interferon" is abbreviated as IFN) and interferon β (IFNβ) are known as type 1 IFNs which possess antiviral activity or antitumor activity. On the other hand, it has also been revealed that IFNα is related to autoimmune disease. For example, abnormal production of IFNα has been reported in patients with the following autoimmune diseases. It has also been suggested that symptoms of the autoimmune diseases can be reduced by neutralization of IFNα.

Systemic lupus erythematosus (Shiozawa et al., Arthr. & Rheum. 35, 412, 1992)

Chronic rheumatism (Hopkins et al., Clin. Exp. Immunol. 73, 88, 1988)

Cases in which symptoms of the autoimmune diseases had been manifested or worsened by administration of recombinant IFNα2 or IFN were reported (Wada et al., Am. J. Gastroenterol. 90, 136, 1995; Perez et al., Am. J. Hematol. 49, 365, 1995; Wilson L E et al, Semin Arthritis. Rheum. 32, 163-173, 2002).

Further, it has also been revealed that IFNα induces differentiation of dendritic cells. The dendritic cell is also an antigen presenting cell. Therefore, it is considered that the differentiation induction of dendritic cells consists an important mechanism in autoimmune diseases. It has been suggested that there is a deep association between the differentiation induction of dendritic cells of IFNα and the onset of systemic lupus erythematosus (Blanco et al., Science, 16:294, 1540-1543, 2001). Thus, it has been pointed out that IFNα is closely related to the antitumor activity as well as autoimmune diseases. In addition, IFNα is deeply involved in the onset of psoriasis (Nestle F O et al., J. Exp. Med. 202, 135-143, 2005).

Interferon Producing cells (IPCs) were identified as cells which produce type 1 IFN in large quantities associated with virus infection. Few IPCs are presented in the blood. It is considered that peripheral blood lymphocytes account for 1% or less of IPCs. However, IPCs have a very high capacity to produce IFN. IFN producing capacity of IPCs reaches, for example, 3000 pg/mL/$10^4$ cells. That is, it may be said that most of the IFNα or IFNβ in the blood, which is produced at viral infection, is resulted from IPCs, although there are few cells.

On the other hand, IPCs are undifferentiated lymphoid dendritic cells which are considered as precursor cells of dendritic cells. IPCs may be referred to as Plasmacytoid dendritic cells. IPCs are differentiated into dendritic cells by virus stimulation and induce the production of IFNγ or IL-10 by T cells. IPCs are also differentiated into dendritic cells by IL-3 stimulation. The differentiated dendritic cells by IL-3 stimulation induce the production of Th2 cytokine (IL-4, IL-5, and IL-10) by T cells. Thus, IPCs have properties which allow them to be differentiated into distinct dendritic cells by different stimulation.

Accordingly, IPCs have two profiles: IFN producing cells and precursor cells of dendritic cells. Both cells play an important role in immune system. In other words, IPC is one of the important cells which support immune system in various aspects.

Non-patent document 1: Shiozawa et al., Arthr. & Rheum. 35, 412, 1992

Non-patent document 2: Hopkins et al., Clin. Exp. Immunol. 73, 88, 1988

Non-patent document 3: Wada et al., Am. J. Gastroenterol. 90, 136, 1995

Non-patent document 4: Parez et al., Am. J. Hematol. 49, 365, 1995

Non-patent document 5: Bianco et al., Science, 16:294, 1540-1543, 2001

Non-patent document 6: Ju et al., Gene. 2004 Apr. 28; 331: 159-64.

Non-patent document 7: Colonna M et al., Seminars in Immunology 12: 121-127, 2000.

Non-patent document 8: Nakajima H. et al., J. Immunology 162: 5-8. 1999

Non-patent document 9: Wilson L E et al, Semin Arthritis. Rheum. 32, 163-173, 2002

Non-patent document 10: Nestle F O et al., J. Exp. Med. 202, 135-143, 2005

Patent-document 1: WO03/12061 (U.S. Patent Published Application No. 2003-148316)

DISCLOSURE OF THE INVENTION

Problems to be Solved by the Invention

An objective of the present invention is to provide an antibody binding to immunoglobulin-Like transcript-7 (ILT7), and to detect, identify, or isolate IPCs. Another objective of the present invention is to regulate the activity of IPCs.

Means for Solving the Problems

In order to regulate activity of a humoral factor such as IFN, administration of antibodies, which recognize the factor, is effective. For example, the attempt to treat autoimmune diseases by antibodies against interleukin (IL)-1 or IL-4 have been realized (Guler et al., Arthritis Rheum., 44. S307, 2001). Further, it is assumed that neutralizing antibodies can serve as therapeutic agents of autoimmune diseases as with interferon (Stewart, T A. Cytokine Growth Factor Rev. 14; 139-154, 2003). It can be predicted that the same approach as described above is effective on IFN produced by IPCs. However, such an approach is based on the inhibition of effect of humoral factor after production of the factor. If the production of the desired humoral factor can be directly controlled, more substantial therapeutic effects can be achieved.

Antibodies, which recognize human IPC, have been reported. For example, anti-BDCA-2 monoclonal antibody is human IPC-specific monoclonal antibody (Dzionek A. et al. J. Immunol. 165: 6037-6046, 2000). It is found that anti-BDCA-2 monoclonal antibody is effective in inhibiting IFN production by human IPCs (J. Exp. Med. 194: 1823-1834, 2001). In addition, it has also been reported that monoclonal antibodies, which recognize interferon-producing cells in mice, inhibit the production of interferon (Blood 2004 Jun. 1; 103/11: 4201-4206. Epub 2003 December). It was reported that the reduced number of dendritic cells was due to monoclonal antibodies against plasmacytoid dendritic cells in mice (J. Immunol. 2003, 171: 6466-6477).

Similarly, if antibodies which recognize human IPCs and can regulate the activity are provided, it will be useful. For example, the present inventors have already shown that an antibody, which recognizes Ly49Q, specifically binds to mouse IPCs. However, the antibody against Ly49Q did not interfere with the activity of mouse IPCs (Blood, 1 Apr. 2005, Vol. 105, No. 7, and pp. 2787-2792; WO2004/13325). On the other hand, ILT7 is known as a molecule whose specific expression is seen in Plasmacytoid dendritic cells (Ju X S et al. and Gene. 2004 Apr. 28; 331: 159-64; WO03/12061). However, any antibodies against ILT7 have not been obtained. Therefore, the effects of antibodies on IPCs are also unknown.

ILT7 is a membrane protein containing an immunoglobulin-like motif. It has been reported as one of the molecules expressed in cells of the myeloid system or lymphatic system (Colonna M et al., Seminars in Immunology 12:121-127, 2000). A plurality of molecules with structures analogous to ILT7 is referred to as ILT family. ILT family is also structurally similar to killer cell inhibitory receptors (KIR). ILT7 has four C-type immunoglobulin-like domains as with other molecules of ILT family. It is considered that ILT7 sends activation signals into the cell as with ILT1, ILT1-like protein, ILT8, and LIR6a. It has been confirmed that a molecule belonging to ILT family is expressed in hemocyte system cells (Young et al., Immunogenetics 53: 270-278, 2001; "The KIR Gene Cluster." Carrington, Mary and Norman, Paul. Bethesda (MD): National Library of Medicine (US), NCBI; 2003).

Then, a high expression of ILT7 was detected in Plasmacytoid dendritic cells (PDC) and a low expression of ILT7 was detected in monocyte-derived dendritic cells (MDDC) by subtractive hybridization. ILT2 and ILT3 were expressed in not only PDC but also DC obtained from MDDC or CD34 positive cells. However, since mRNA in ILT7 was specifically expressed in PDC, it was found that the mRNA might serve as a marker of PDC. Additionally, it was found that at that time, the expression of ILT7 was reduced by stimulation of CpG (Ju X S et al. Gene. 2004 Apr. 28; 331: 159-64; WO03/12061).

The present inventors confirmed that specific expression of ILT7 in IPC was facilitated through the study on human IPC. Then, the present inventors attempted to produce antibodies of ILT7 and to elucidate the effects. For example, molecules constituting ILT families such as ILT2 and ILT3 have high conservation, particularly in amino acid sequences of extracellular domains (FIG. 9). These ILT families exhibit characteristic expression profiles in various blood cells, respectively. Therefore, it is a very important subject to obtain an antibody which can immunologically distinguish between other ILT family molecules and ILT7. However, in fact, it was difficult to produce an antibody which binds specifically to human IPCs using ILT7 as an immunogen because of the obstacles described below.

Generally, a protein produced by gene-recombination technology is used as an immunogen in order to obtain an antibody which recognizes a trace amount of proteins derived from living organisms. The present inventors tried to express human ILT7 on the basis of information of a base sequence of cDNA of human ILT7, which had already been found, and the amino acid sequence coded by the base sequence (GenBank Accession No. NM_012276). However, the present inventors could not produce human ILT7 as a recombinant under normal conditions.

The partial amino acid sequence of natural protein is often tried to be used as an immunogen in order to obtain a protein antibody. However, there are few amino acid sequences specific to human ILT7 in proteins since homology to the amino acid sequences is extremely high in ILT family. In addition, it is necessary to select the region constituted of the portion that is recognized as an epitope by antibodies on the surface of cells for the purpose of allowing antibodies to recognize molecules on the surface of cells. Therefore, it has been considered that formation of an antibody which is specific to ILT7 by using a fragment amino acid sequence as an immunogen is not realistic.

The present inventors showed that an antibody, which binds to IPCs, could be obtained by using a special immunogen under such conditions. Further, the present inventors found that the antibody thus obtained specifically recognized human IPCs and further had an effect of regulating the activity and thereby succeeded in completing the present invention. That is, the present invention relates to the following anti-ILT7 antibody, production method thereof, and use thereof.

Effects of the Invention

The present invention provides an immunogen useful in producing an antibody which recognizes human ILT7 and a production method of anti-human ILT7 antibody using the immunogen. ILT7 is a membrane protein belonging to ILT family. Particularly, the amino acid sequence of the extracellular region is highly conserved among ILT families. Therefore, it is extremely difficult to produce an antibody which distinguishes between ILT families by general immunization methods. The present inventors showed that the antibody, which recognizes human ILT7, can be easily obtained by using animal cells in which ILT7 is coexpressed with cell membrane protein. Anti-ILT7 antibody, which can be obtained by the present invention, has a high specificity which distinguishes cells expressing other ILT families from those expressing human IPCs.

In a preferred embodiment, anti-human ILT7 antibody provided by the present invention binds to human IPCs. In addition, the antibody of the present invention specifically recognizes human IPCs. Therefore, it is useful in detecting and isolating IPCs. IPC is a cell which produces most of the type 1 interferon. Therefore, the detection and isolation are important in diagnosis and study of diseases that involve IPCs such as autoimmune diseases. Particularly, according to the findings of the present inventors, the expression of ILT7 in IPCs is not reduced under the presence of IFNα. IFNα expression is often facilitated inpatients with autoimmune diseases. This means that anti-ILT7 antibody of the present invention can be used for the detection and isolation of IPCs as to the patients with autoimmune diseases in which the expression of IFNα is facilitated.

Anti-ILT7 antibody provided by the present invention has an effect which regulates the activity of human IPCs in a preferred embodiment. Therefore, the anti-ILT7 antibody of the present invention can be used to inhibit the activity of IPCs. As described previously, the expression of ILT7 in IPCs is not reduced under the presence of IFNα. Therefore, if the inhibition of the activity of IPCs by the antibody of the present invention is used, a therapeutic effect on the patients with autoimmune diseases in which the expression of IFNα is facilitated may be expected.

Scant IPCs produce a large amount of IFN. Antibodies as many as IFN molecules are necessary for neutralization of IFN. However, producing cell activation is directly inhibited in the present invention. As a result, a strong inhibitory effect on IFN can be expected even if smaller amount of antibodies are used compared with neutralization by anti-IFN antibody. Furthermore, in the case where IFN is continuously produced, it is predicted that neutralization by IFN antibodies is transient inhibition. In the present invention, since the activity of IPCs is inhibited, IFN production inhibiting effect can be expected over a long period of time.

BRIEF DESCRIPTION OF THE DRAWINGS

FIG. 2 is a diagram showing structures of ILT7 protein, where FIG. 2(a) shows an amino acid sequence of ILT7 protein and further shows the estimated secretion signal sequence and transmembrane domain in the drawing, and FIG. 2(b) shows a schematic diagram of ILT7 proteins that are encoded by constructed expression vectors.

FIG. 9a is a diagram showing amino acid sequences of family molecules with high homology to ILT7 molecules. Each amino acid sequence of the extracellular region is mainly shown as an alignment; FIG. 9b is a continuation of FIG. 9a; and FIG. 9c is a continuation of FIG. 9b.

Figure 1A:
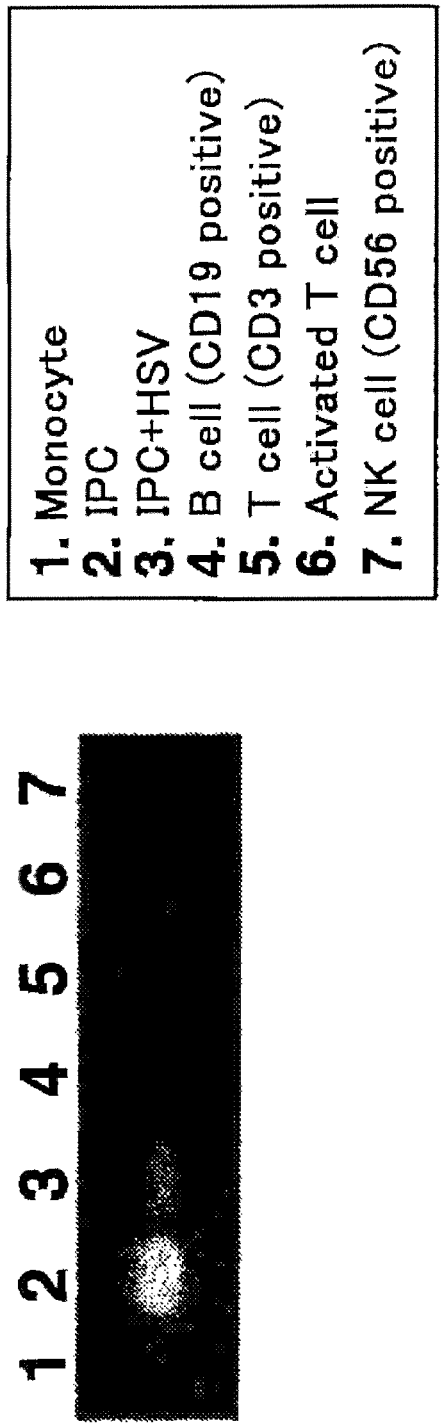
FIG. 1a is a photograph in which the expression of mRNA of ILT7 gene is examined by RT-PCR method. It is a result of the analyzed expression of mRNA of ILT7 gene in human immunocytes.

The fluorescence intensity of APC is an indicator of the amount of ILT7-anti-ILT7 antibody immune complex which was present on the surface of cells before incubation and it is detected regardless of whether ILT7-anti-ILT7 antibody immune complex is present on the target cell surface or is incorporated into the cell after incubation. On the other hand, the fluorescence intensity of FITC is an indicator of the amount of ILT7-anti-ILT7 antibody immune complex which remains on the surface of cells after incubation. That is, the fluorescence intensity of FITC is decreased by internalization.

BEST MODE FOR CARRYING OUT THE INVENTION

It has been reported that human ILT7 (immunoglobulin-like transcript-7) is a molecule which is specifically expressed in Plasmacytoid dendritic cells (Gene. 2004 Apr. 28; 331:1 59-64; WO03/12061). Alternatively, it is also known that human ILT7 can be used as a predictive indicator for prognosis of lymphoma (WO2005/24043). However, a method for producing an antibody capable of recognizing human ILT7 has not been established.

Human ILT7 consists of 499 amino acid residues as shown in SEQ ID NO: 2 and it is a type 1 transmembrane protein comprising four immunoglobulin-like domains in the structure and one transmembrane region (445-466; from 429 to 450 in SEQ ID NO: 2). Among 444 amino acid residues including N-terminal, 16 amino acid residues (from −15 to −1, in SEQ ID NO: 2) are signal sequences and 17 to 444 amino acid residues (from 1 to 428, in SEQ ID NO: 2) constitute an extracellular domain. On the other hand, the C-terminal region is an intracellular domain. Most of portions of the human ILT7 are extracellular domains and 33 amino acid residues constitute an intracellular domain (from 467 to 499; from 451 to 483, in SEQ ID NO: 2). It is not predicted that a motif, which is involved in signalization, is present in an intracellular domain. A full length amino acid sequence of human ILT7 is shown in SEQ ID NO: 2 and a base sequence of cDNA encoding the amino acid sequence is shown in SEQ ID NC: 1. Here, the coding regions of the matured peptide (72) . . . (1520), shown in SEQ ID NO: 1, do not comprise the termination and initiation codons. That is, protein coding sequences which comprise the termination and initiation codons in SEQ ID NO: 1 are from 24 to 1523.

It is considered that the ligand signal is transmitted to cells by association of human ILT7 with a signal-transducing molecule. For example, most of the Fc receptor γ-chains are present in cells. In addition, the intracellular domain contains an immunoreceptor tyrosine-based activation motif (ITAM) which is involved in signalization. ITAM is an amino acid sequence portion, which is commonly seen in adaptor molecules that are associated with immunoreceptors such as Fc receptors. A motif such as YxxL (SEQ ID NO: 76), which is a target of tyrosine phosphorylation, is comprised in ITAM and the signal is transmitted by the phosphorylation. Known examples of the signal-transducing molecule, which comprises ITAM in an intracellular domain, include CD3ζ and DAP12 in addition to Fc receptor γ-chain. Among these signal-transducing molecules, the molecule associated with human ILT7 is predicted to be the Fc receptor γ-chain. Currently, a ligand, which binds to human ILT7, has not been found.

The present inventors confirmed that ILT7 was specifically expressed in human IPCs by gene expression analysis. The present inventors considered that it would be useful in the study of IPCs if an antibody capable of distinguishing human ILT7 from other molecules immunologically could be obtained. However, many molecules with similar structures exist in ILT family including ILT7. Molecules such as ILT1, ILT2, ILT3, ILT4, ILT5, ILT6, or LIR-8 comprise highly homologous amino acid sequences, particularly in their extracellular domains. Therefore, the present inventors considered that it was difficult to obtain an antibody capable of distinguishing between these molecules using a domain peptide comprising a partial amino acid sequence which constitute an extracellular domain as an immunogen. Then, the present inventors have tried to produce an antibody against human ILT7 using the cells expressing human ILT7 as immunogens.

However, the use of general expression vectors did not cause the expression of cDNA of human ILT7 in animal cells. It has been reported that ILT1 molecule having a structure very similar to ILT7 associates with the Fc receptor γ-chain. That is, when cells in which the Fc receptor γ-chain was expressed such as RBL (rat basophilic leukemia) cells and P815 (mouse mastocytoma) cells were used as host cells, the expression of ILT1 on the cell surface was observed. However, if ILT1 was forced to be expressed in 293 cells in which Fc receptor γ-chain was not originally expressed, the cell-surface expression was not observed. On the other hand, it was shown that the cell-surface expression of ILT1 could be confirmed when ILT1 was coexpressed with the Fc receptor γ-chain (Nakajima H. et al., J. Immunology 162:5-8. 1999). However, there is no information about an immunogen for producing ILT7 antibodies.

For example, in the report, RBL cells into which ILT1 gene is introduced are used as immunogens to produce ILT1 antibodies. The present inventors tried to produce ILT7 antibodies using the combination of RBL cells with ILT7 gene in the same manner as described. However, even if ILT7 was forced to be expressed in RBL cells (P815), the cell-surface expression of ILT7 was not observed, and therefore it could not be used as an immunogen.

The present inventors have conducted dedicated research in order to obtain the antibody capable of recognizing human ILT7. As a result, the present inventors found that the desired antibody could be produced by using a specific transformed cell as an immunogen and completed the present invention. That is, the present invention relates to a monoclonal antibody which binds to the extracellular domain of human ILT7, and relates to a fragment comprising its antigen binding region.

In the present invention, human ILT7 can be defined as a natural molecule which is expressed in human IPCs or a molecule which is immunologically equivalent to ILT7 which is expressed in human IPCs. In the present invention, the binding of antibodies to human ILT7 can be confirmed, for example, as follows.

Confirmation Based on Responsiveness to Human Cells:

According to the findings of the present inventors, specific expression of human ILT7 was observed in human IPCs. Originally, human ILT7 was isolated as a gene whose expression is seen in Plasmacytoid dendritic cells (Blood. 2002 100; 3295-3303, Gene. 2004 Apr. 28; 331:159-64). In addition, it is also known that it can be used as a marker of Plasmacytoid dendritic cells (WO03/12061). It is assumed that Plasmacytoid dendritic cells and IPCs are mostly identical cell populations or their large portions are common. Therefore, there is no contradiction between these reports and the findings of the present inventors.

Considering such expression profile of human ILT7, first, the binding activity of IPCs or Plasmacytoid dendritic cells to at least a certain subset is one of the important characteristics of the antibody which binds to human ILT in the present invention. Cell surface markers specific to respective cell populations can be used to determine whether a certain cell is IPC or Plasmacytoid dendritic cell. For example, binding to the desired cells can be confirmed by double staining with the antibody which binds to cell surface markers and the antibody whose binding activity should be checked. That is, IPCs in the present invention comprises, for example, cells which express BDCA2.

Confirmation Based on Responsiveness to Transformed Cells Expressing Human ILT7 Gene:

The present inventors found that an immunological characteristic of ILT7 expressed in human IPCs was reconstructed when expression of human ILT7 gene was carried out under a specific condition. Therefore, the responsiveness to human ILT7 can also be confirmed based on the responsiveness of antibodies to cells into which a gene encoding ILT7 is artificially introduced. Namely, the present invention relates to a monoclonal antibody which comprises the amino acid sequence constituting an extracellular domain as the extracellular domain and binds to a molecule coexpressed with the signal-transducing molecule or relates to a fragment comprising its antigen binding region. Here, the extracellular domain is composed of an amino acid sequence which corresponds to the 17th to 444th position of the N terminal amino acid sequence shown in SEQ ID NO: 2 (from 1 to 428 in SEQ ID NO: 2).

For example, the immunological characteristic of ILT7 expressed in human IPCs is maintained in cells co-transfected with an expression vector comprising a DNA encoding human ILT7 and an expression vector comprising a DNA encoding the signal-transducing molecule. Therefore, a transformed cell, which coexpresses human ILT7 and the signal-transducing molecule, is preferable to confirm the binding affinity of antibodies to the extracellular domain of human ILT7 in the present invention. In the present invention, it is desirable to use a cell, which is not transformed as controls when the responsiveness of antibodies is confirmed by using the transformed cell. Further, it is also important to confirm that the binding of antibodies is not detected using the same host cell which expresses only the signal-transducing molecule as a control.

In the present invention, a molecule, which induces the expression of human ILT7 on the cell surface, can be used as the signal-transducing molecule for the coexpression. The signal-transducing molecule in the present invention can also be defined as a molecule which can impart the immunological characteristic of natural human ILT7 to at least the extracellular domain of ILT7 molecule in a cell which expresses ILT7. As used herein, the term "immunological characteristic" of natural human ILT7 means recognition by an antibody which binds to human IPCs.

Specifically, it is preferable to use Fc receptor γ-chain or DAP12 as a signal-transducing molecule. In the present invention, the Fc receptor γ-chain is particularly preferable as the signal-transducing molecule. The Fc receptor γ-chain is a molecule consisting of amino acid sequences shown in SEQ ID NO: 16. The signal-transducing molecule may be a fragment as long as human ILT7 to be coexpressed is localized at the cell surface. As long as human ILT7 to be coexpressed is localized at the cell surface, the mutation or addition of the amino acid sequence is permitted in the amino acid sequences shown in SEQ ID NO: 16. That is, the present invention provides methods for producing cells which produce a monoclonal antibody which binds to the extracellular domain of human ILT7, comprising the following steps of:

(1) administering a cell which exogenously expresses a protein comprising extracellular domain of human ILT7 and a molecule comprising amino acid sequences described in SEQ ID NO: 16 to immune animals; and (2) selecting an antibody producing cell which produces the antibody which binds to human ILT7 from antibody producing cells of the immune animals.

Subsequently, as the antibody which binds to human ILT7 in the present invention, it is preferable to use an antibody in which crossing with cell populations which are known to express ILT families other than ILT7 is not observed. Specifically, as the antibody which binds to human ILT7 in the present invention, it is preferable to use an antibody in which the binding to the cell populations which are known to express ILT families other than ILT7 cannot be observed under the same condition as the condition in which the binding to IPCs was confirmed. As already described, for example, ILT2 and ILT3 are expressed in not only PDC but also DC obtained from MDDC or CD34 positive cells (Gene. 2004 Apr. 28; 331: 159-64). On the other hand, the expression ILT7 cannot be detected due to the differentiation of IPCs into dendritic cells. Therefore, the antibody cannot detect the binding to DCs obtained from MDDC or CD34 positive cells under the condition in which the binding to IPCs can be confirmed is comprised in the antibody which binds to human ILT 7 in the present invention.

The following expression patterns as to other ILT family molecules have been reported ("The KIR Gene Cluster" Carrington, Mary and Norman, Paul. Bethesda (MD): National Library of Medicine (US), NCBI; 2003, Gene. 2004 Apr. 28; 331: 159-64). Therefore, an antibody which binds to human IPCs or PDCs and whose binding to the following cells cannot be confirmed is included in an antibody having specificity to ILT7:

ILT1; myeloid lineage cells (monocytes, DCs derived from monocytes, macrophages);

ILT2; PDCs, B cells, CD34 positive cells, DCs derived from CD34 positive cells, and DCs derived from monocytes;

ILT3; PDCs and DCs;

ILT5; monocytes, DCs derived from CD34 positive cells, and DCs derived from monocytes; and ILT8; monocyte lineage cells.

That is, the monoclonal antibody, which binds to the extracellular domain of human ILT7 in the present invention preferably, comprises a monoclonal antibody which has the following immunological characteristics:

a) the monoclonal antibody binds to human IPCs; and b) the binding of the monoclonal antibody to one or more cells selected from the group consisting of monocytes, macrophages, B cells, CD34 positive cells, and dendritic cells derived from these cells cannot be confirmed under the condition for binding to human IPCs.

As the monoclonal antibody of the present invention, it is preferable to use an antibody in which the binding to monocytes, macrophages, B cells, CD34 positive cells, and dendritic cells derived from these cells cannot be confirmed under the condition for binding, particularly to human IPCs.

Alternatively, the monoclonal antibody, which binds to the extracellular domain of human ILT7 in the present invention, preferably comprises a monoclonal antibody which has the following immunological characteristics:

c) the monoclonal antibody binds to the transformed cell which is co-transfected with an expression vector expressively carrying the DNA encoding human ILT7 and an expression vector expressively carrying the DNA encoding the signal-transducing molecule;

d) the binding to the host cell prior to transformation cannot be confirmed under the condition for binding to the co-transfected cells as described in c); or the monoclonal antibody of the present invention comprises a monoclonal antibody which has the following immunological characteristics:

e) the binding to the host cell which expresses only the signal-transducing molecule cannot be confirmed under the condition for binding to the co-transfected cells as described in c).

In the present invention, the fact that anti-ILT7 monoclonal antibody does not intersect with the ILT family of other molecules can be confirmed using cells in which each ILT family was forced to be expressed. That is, for forced expression, cDNA encoding each ILT family of amino acid sequences is introduced into an appropriate host cell. The anti-ILT7 monoclonal antibody whose crossing should be confirmed is made to contact with the obtained transformed cell. Then, it can be confirmed that if the binding of the antibody to the cell, which expresses ILT family molecules other than ILT7, is not observed, the antibody is able to immunologically distinguish between ILT7 and other ILT family molecules. For example, in examples described below, the fact that the anti-ILT7 monoclonal antibody obtained by the present invention does not intersect with ILT1, ILT2, and ILT3 is confirmed. Therefore, a preferable example of the monoclonal antibody in the present invention is the monoclonal antibody binding to ILT7 in which the binding to ILT1, ILT2, and ILT3 cannot be detected under the same condition.

Particularly, ILT2 and ILT3 are genes whose expression in IPCs has been confirmed (Ju at al. Gene 331, 159-164, 2004). However, these molecules may show expression profiles unique to each cell type depending on the respective differentiation levels in IPCs or conditions such as the stimulation with viruses or other cytokines. The use of an antibody, which is able to immunologically distinguish these ILT family molecules from ILT7, allows for specifically detecting changes in the expression of ILT7.

The binding of a monoclonal antibody whose binding activity should be confirmed to various kinds of cells can be confirmed based on, for example, the principle of flow cytometry. In order to confirm the responsiveness of antibodies based on the principle of flow cytometry, it is advantageous to label antibodies with molecule or atomic group which produces a detectable signal in advance. Generally, the fluorescent or luminescent labels are used.

Fluorescence-activated cell sorter (FACS) can be used to analyze the binding of the fluorescent-labeled antibodies to cells based on the principle of flow cytometry. The use of FACS allows for efficiently confirming the binding of a plurality of antibodies to a plurality of cells.

Specifically, for example, antibody A which has been previously found to be able to identify IPCs and antibody B whose binding characteristics to IPCS should be analyzed are reacted with cell populations comprising IPCs at the same time. Antibody A and antibody B are labeled with a fluorescence signal which is mutually distinguished by these antibodies in advance. In the case where both signals are detected from the same cell populations, the binding of those antibodies to the same cell populations can be confirmed. In other words, it is found that both antibodies A and B have the same binding characteristics. In the case where they bind to different cell populations, it is clear that both antibodies have distinct binding characteristics.

A preferable example of the monoclonal antibody in the present invention may comprise a monoclonal antibody which is produced by hybridoma ILT7#11 or ILT7#17. Hybridoma ILT7#11 and hybridoma ILT7#17 have been deposited with National Institute of Advanced Industrial Science and Technology, International Patent Organism Depositary under Accession Nos. FERM BP-10704 and FERM BP-10705 on Oct. 21, 2005.

The specified depository content is as follows:
(a) Appellation and address of depository institution Appellation: National Institute of Advanced Industrial Science and Technology, International Patent Organism Depositary Address: AIST Tsukuba Central 6, 1-1-1, Higashi, Tsukuba-shi, Ibaraki, Japan (zip code 305-8566)
(b) Deposited date: Oct. 21, 2005
(c) Accession number: FERM BP-10704 (hybridoma ILT7#11)
(c) Accession number: FERM BP-10705 (hybridoma ILT7#17)

The monoclonal antibody of the present invention may be a fragment comprising its antigen binding region. For example, an antibody fragment comprising the antigen binding region which is obtained by enzymatic digestion of IgG can be used as the antibody in the present invention. Specifically, antibody fragments such as Fab and $F(ab')_2$ can be obtained by digestion with papain or pepsin. It is well known that these antibody fragments can be used as antibody molecules which have affinity for antibodies. Alternatively, antibodies constructed by genetic recombination can also be used as long as satisfactory antigen-binding activity is maintained. Examples of the antibodies constructed by genetic recombination comprise chimeric antibodies, CDR-transplanted antibodies, single chain Fvs, diabodies, linear antibodies, and polyspecific antibodies formed of antibody fragments. It is common knowledge that these antibodies can be given by using monoclonal antibodies or antibody producing cells which produce the antibodies.

The monoclonal antibody of the present invention can be obtained by using a specific transformed cell as an immunogen. That is, the present invention relates to a method for producing cells which produce a monoclonal antibody which binds to the extracellular domain of human ILT7, comprising the following steps of:

(1) administering a cell which expresses an exogenous protein comprising extracellular domain of human ILT7 and an exogenous molecule which is associated with human ILT7 to immune animals; and (2) selecting an antibody producing cell which produces the antibody which binds to human ILT7 from antibody producing cells of the immune animals.

The antibody producing cells thus obtained or the immortalized antibody producing cells are cultured and the desired monoclonal antibodies can be recovered from the cultures. With reference to the method for immortalizing antibody producing cells, various methods are known.

In the method for producing the monoclonal antibody of the present invention, usable examples of the molecule, which is associated with human ILT7 for producing a transformed cell to be used as an immunogen, comprise cell membrane proteins. Among them, a signal-transducing molecule, which is localized in cell membranes, is preferable to use as a cell membrane protein in the present invention. The term "signal-transducing molecule" means a molecule which is associated with proteins and cells having receptor structures in the extracellular domain and transmits the stimulation of binding of ligands to receptors into cells. Examples of the signal-transducing molecule comprise Fc receptor γ-chain, DAP12, or the like. For example, Fc receptor γ-chain is preferable to use as a cell membrane protein in the present invention. Amino acid sequences of human DAP12 and Fc receptor γ-chain as well as a base sequence of cDNA, which encodes the sequences, are publicly known. A base sequence of human Fc receptor γ-chain and an amino acid sequence which is encoded by the base sequence are shown in SEQ ID NOs: 15 and 16, respectively.

In the present invention, a transformed cell to be used as an immunogen can be obtained by preparing, for example, a cell expressively carrying the following (a) and (b):

(a) an exogenous polynucleotide encoding an amino acid sequence comprising an extracellular domain of human ILT7; and (b) an exogenous polynucleotide encoding Fc receptor γ-chain In the present invention, an exogenous polynucleotide means a polynucleotide which is artificially introduced into a host cell. When human cells are used as cells, human genes are introduced into human cells. In such a combination, an artificially introduced polynucleotide means the exogenous polynucleotide. Therefore, ectopic expression of human ILT7 or human Fc receptor γ-chain is comprised in expression of the exogenous polynucleotide.

As used herein, the term "extracellular domain of human ILT7" means the amino acid sequence from the 17th to 444th position of the amino acid sequence described in SEQ ID NO: 2 which corresponds to the extracellular domain of the amino acid sequence (from 1 to 428 in SEQ ID NO: 2). As an amino acid sequence comprising the extracellular domain of human ILT7 in the present invention, it is preferable to use the amino acid sequence which comprises each region, for example, starting from the N terminal, in order of the following:
[Signal sequence+extracellular domain+transmembrane domain+intracellular region]

Alternatively, an amino acid sequence, which partially lacks an intracellular region as described below, is included in the amino acid sequence comprising the extracellular domain of human ILT7 in the present invention.
[Signal sequence+extracellular domain+transmembrane domain+a portion of intracellular region]

Furthermore, a structure, which lacks an intracellular region as mentioned below, is included in the amino acid sequence comprising the extracellular domain of human ILT7 in the present invention.
[Signal sequence+extracellular domain+transmembrane domain]

In the structure, regions other than the extracellular domain may be amino acid sequences which are selected from the amino acid sequence shown in SEQ ID NO: 2, or may be combined with other amino acid sequences having homology with the regions. For example, the amino acid sequence constituting a signal sequence, a transmembrane domain, and an intracellular region may be an amino acid sequence of ILT family molecules other than ILT7. Or, it may be combined with the amino acid sequence of ILT family in species other than human. Further, the amino acid sequence, which constitutes regions other than the extracellular domain, may comprise a mutation in the range capable of maintaining the function of each region. Alternatively, other regions may intervene between each region. For example, an epitope tag such as FLAG can also be inserted between the signal sequence and the extracellular domain. Particularly, the signal sequence is removed by processing during its transfer to the cell membrane surface after being translated into protein. Therefore, arbitrary amino acid sequence, which induces transit of the translated protein to the cell membrane, can be used as the signal sequence. More specifically, it is preferable to use the amino acid sequence (SEQ ID NO: 2) of human ILT7 as the amino acid sequence comprising the extracellular domain of human ILT7.

Therefore, in the present invention, an arbitrary base sequence which encodes the amino acid sequence constituting the above-mentioned structure [signal sequence+extracellular domain+transmembrane domain+intracellular region] can be used as the polynucleotide which constitutes the exogenous polynucleotide described in (a). For example, the amino acid sequence of SEQ ID NO: 2 is encoded by the base sequence described in SEQ ID NO: 1.

In the present invention, an expression vector expressively carrying the above-mentioned polynucleotides (a) and (b) may be introduced to an appropriate host cell in order to obtain a transformed cell to be used as an immunogen. The Polynucleotides (a) and (b) can be carried on one vector or different vectors. When each polynucleotide is carried on different vectors, the host cells are co-transfected with two kinds of vectors.

Preferable examples of the host cell in the present invention comprise mammalian cells. Specific examples of the host cell comprise cells derived from humans, monkeys, mice or rats. Particularly, the cells derived from humans are preferable as host cells. For example, it is preferable to use 293T cells derived from human as the host cell in the present invention. 293T cells can be obtained as ATCC CRL-11268. In addition, cells derived from immune animals can also be used as host cells. When cells derived from immune animals are used as immunogens, little immunological response to host cells is given. For that reason, an antibody against the extracellular domain of exogenously expressed ILT7 can be obtained efficiently. Therefore, for example, when mice are used as immune animals, cells derived from mice can also be used as host cells.

The above-mentioned polynucleotides can be transformed into cells by carrying them on a vector capable of inducing expression in host cells. Commercially available vectors, which can induce the expression in mammalian cells, may be used. Expression vectors such as pCMV-Script (R) Vector, PSG5 Vector (manufactured by Stratagene), pcDNA3.1 (manufactured by Invitrogen) can be used for the present invention.

The transformed cells thus obtained are administered to immune animals together with additional components such as adjuvants, if necessary. Usable examples of the adjuvant include Freund's complete adjuvant, and the like. In case of using mice as immune animals, the transformed cells can be administered in the range of $10^4$ to $10^9$ cells, more specifically $10^4$ to $10^6$ cells. Generally, multiple doses of immunogen are given at regular intervals until the antibody titer is elevated. For example, in the case of a short-term immunization, the transformed cells are administered at 2 to 4 day intervals, more specifically at intervals of 3 days. After administering twice or three times, antibody producing cells can be recovered. Alternatively, they are administered once weekly and antibody producing cells can also be recovered after administering five or six times.

In the present invention, the recovered antibody producing cells are cloned to give monoclonal antibodies. It is preferable that the antibody producing cells are immortalized for cloning. For example, the cell fusion method as typified by the hybridoma method or transformation stein-Barr virus can be used as the method of immortalization of antibody producing cells.

As for antibody producing cells, one cell produces one kind of antibody. Therefore, the establishment of cell populations derived from one cell (i.e. cloning) allows for producing monoclonal antibodies. The hybridoma method involves the process in which antibody producing cells are fused with an appropriate cell line, which is immortalized and then subjected to cloning. The immortalized antibody producing cells can be cloned by a technique such as limiting dilution method. It is known that there are lots of cell lines useful for the hybridoma method. These cell lines are excellent in the immortalization efficiency of lymphocytic cells and have various genetic markers which are needed to select the successfully fused cells. Further, when the production of antibody producing cells is intended, a cell line lacking the ability to produce antibodies can also be used.

For example, mouse myelomas P3x63Ag8.653 (ATCC CRL-1580) and P3x63Ag8U.1 (ATCCCRL-1597) are widely used as useful cell lines for the cell fusion method for mice or rats. In general, a hybridoma is produced by the fusion of homogeneous cells, while a monoclonal antibody can also be obtained from hetero hybridoma from a different species among closely related species.

Specific protocols of the cell fusion have been publicly known. That is, antibody producing cells of immune animals are mixed with appropriate fusion partners to perform cell fusion. Usable examples of the antibody producing cell include splenic cells, lymphocyte cells collected from the lymph node, and peripheral blood B cells. As fusion partners, various cell lines described previously can be used. The polyethylene glycol method and electric fusion method can be used for cell fusion.

Next, on the basis of selective markers of fused cells, the successfully fused cells are selected. For example, when HAT sensitive cell line is used for cell fusion, the successfully fused cells are selected by selecting cells growing in HAT medium. Further, it is confirmed that the antibodies produced by the selected cells have the desired responsiveness.

Each hybridoma is screened based on the responsiveness of antibodies. That is, the hybridoma producing antibodies which bind to human ILT7 is selected by the method as described previously. Preferably, when the selected hybridoma is subcloned and then the production of the desired antibody is finally confirmed, the confirmed antibody is selected as a hybridoma producing monoclonal antibody of the present invention.

Specifically, the desired hybridoma can be selected based on the responsiveness to human cells or the responsiveness to the transformed cell which expresses human ILT7 gene. The antibodies, which bind to cells, can be detected based on the principle of immunoassay. For example, ELISA, which uses cells as antigens, can be utilized for detection of the desired antibody. Specifically, a culture supernatant of hybridoma is made to contact with a support on which human IPC or the transformed cell used as an immunogen. In the case where the culture supernatant comprises the desired antibody, the antibody is trapped in the cell immobilized on the support. Then, the solid phase is separated from the culture supernatant, which is washed, if necessary. Thereafter, the antibody trapped in the solid phase can be detected. An antibody, which recognizes an antibody, can be used for the detection of antibodies. For example, an antibody of mouse can be detected by an anti-mouse immunoglobulin antibody. The detection is easy if the antibody, which recognizes an antibody, is labeled. Usable examples of the label include enzymes, fluorescent dyes, luminescent dyes, and the like.

On the other hand, particles and an inner wall of a microtiter plate can be used as the support on which cells are immobilized. Cells can be immobilized on particles made of plastic or the surface of a container by physical adsorption. Usable examples of the support for immobilizing cells include beads made of polystyrene and reaction vessels.

In the selection of hybridomas, the production of the antibody against not ILT7 but the host cell of the transformed cell used as an immunogen may be predicted. For example, as illustrated in Examples, in the case where a human cell is used as an immunogen and a mouse is used as an immune animal, the human cell is recognized as a foreign substance. Thus, the production of an antibody, which binds to the foreign substance, is predicted. In the present invention, it is intended to obtain an antibody capable of recognizing human ILT7. Therefore, it is not necessary to obtain an antibody which recognizes human cell antigens other than human ILT7. In order to remove hybridomas, which produce such an antibody in screening, undesired antibodies, can be absorbed prior to the confirmation of the antibody responsiveness.

Undesired antibodies can be absorbed by an antigen to which an antibody presumed to exist binds. Specifically, for example, an antibody against human cell antigens other than human ILT7 can be absorbed by a cell which cannot detect the expression of human ILT7. In the present invention, it is preferable to use the host cell used for the immunogen as an antigen for absorbing the undesired antibodies. Alternatively, a host cell which does not express the extracellular domain of human ILT7, but expresses molecule which associates with ILT7 can be used as the antigen for absorbing the antibodies.

As for the monoclonal antibody whose binding activity to antigen is confirmed, its actual effect on the IPC activity is confirmed, if necessary. The effect on IPC can be confirmed by methods such as the methods described below.

As for the monoclonal antibody of the present invention, a hybridoma producing the monoclonal antibody is cultured and the monoclonal antibody of the present invention is recovered from the resulting culture. The hybridoma can be cultured in vitro or in vivo. In the case of in vitro, the hybridoma can be cultured by using a known culture medium such as RPMI1640. The immunoglobulin secreted by the hybridoma is accumulated in the culture supernatant. Therefore, the monoclonal antibody of the present invention can be obtained by collecting the culture supernatant and purifying it, if necessary. It is easier to purify the immunoglobulin when serum is not added to the culture medium. However, for the purpose of more rapid proliferation of the hybridoma and facilitation of antibody production, 10% fetal bovine serum can also be added to the culture medium.

The hybridoma can also be cultured in vivo. Specifically, the intraperitoneal cultivation of the hybridoma can be made by inoculating the hybridoma into the abdominal cavity of nude mice. Monoclonal antibodies are accumulated in the ascites. Therefore, if the ascites is obtained and purified as needed, the required monoclonal antibody can be produced. The obtained monoclonal antibodies can be appropriately modified or processed in accordance with the intended use.

The monoclonal antibody of the present invention can be expressed by obtaining cDNA which encodes the antigen binding region of antibody from the hybridoma and inserting into an appropriate expression vector. The technique, in which cDNA which encodes a variable region of antibody is obtained and then it is expressed in an appropriate host cell, is known. In addition, the method in which a chimeric antibody is made by ligating a variable region comprising the antigen binding region into a constant region is also known.

Preferable examples of the monoclonal antibody in the present invention comprise monoclonal antibodies produced by hybridoma #11 (Accession number: FERM BP-10704), hybridoma #17 (Accession number: FERM BP-10705), or hybridoma #37. Amino acid sequences which constitute variable regions of these monoclonal antibodies as well as base sequences of cDNA encoding thereof are described below. Therefore, for example, chimeric antibodies to be obtained by conjugating these variable regions to constant regions of other immunoglobulins are preferable in the present invention. In amino acid sequences described in the Sequence Listing, the amino acid sequence from 1 to C terminus constitutes a mature protein. That is, the consecutive amino acid sequence from 1 to C terminus for each amino acid sequence is a mature sequence of each amino acid sequence. On the other hand, the amino acid sequence represented by a numerical value from N terminus to −1 is a signal sequence.

|     | Heavy chain variable region | Light chain variable region |
| --- | --- | --- |
| #11 | SEQ ID NO: 38 (base sequence) | SEQ ID NO: 40 (base sequence) |
|     | SEQ ID NO: 39 (amino acid sequence) | SEQ ID NO: 41 (amino acid sequence) |
| #17 | SEQ ID NO: 42 (base sequence) | SEQ ID NO: 44 (base sequence) |
|     | SEQ ID NO: 43 (amino acid sequence) | SEQ ID NO: 45 (amino acid sequence) |
| #37 | SEQ ID NO: 46 (base sequence) | SEQ ID NO: 48 (base sequence) |
|     | SEQ ID NO: 47 (amino acid sequence) | SEQ ID NO: 49 (amino acid sequence) |

For example, a mouse (variable region)-human (constant region) chimeric antibody can be made by ligating these variable region genes into a human IgG1 heavy chain constant region and a gene encoding human Ig kappa light chain constant region, respectively. Amino acid sequences of such a chimeric antibody and base sequences encoding thereof are respectively described below. Chimeric antibodies specified by these sequences show the construction of a preferred embodiment of anti-ILT7 monoclonal antibody in the present invention. In the following amino acid sequences of chimeric antibodies, the amino acid sequence from N terminus to −1 corresponds to the signal sequence and the amino acid sequence from 1 to C terminus corresponds to the mature protein. That is, a chimeric antibody comprised of heavy and light chains, which consist of the amino acid sequence from 1 to C terminus for each amino acid sequence, is preferable in the present invention.

|     | Heavy chain | Light chain |
| --- | --- | --- |
| #11 | SEQ ID NO: 50 (base sequence) | SEQ ID NO: 52 (base sequence) |
|     | SEQ ID NO: 51 (amino acid sequence) | SEQ ID NO: 53 (amino acid sequence) |
| #17 | SEQ ID NO: 54 (base sequence) | SEQ ID NO: 56 (base sequence) |
|     | SEQ ID NO: 55 (amino acid sequence) | SEQ ID NO: 57 (amino acid sequence) |

Further, the antigen-binding activity of monoclonal antibody can also be grafted to other immunoglobulins. The variable region of immunoglobulin is comprised of a complementarity-determining region (CDR) and a frame region. The antigen-binding property of each immunoglobulin is determined by CDR and the frame maintains the structure of antigen binding region. The amino acid sequence of CDR is extremely rich in diversity, while the amino acid sequence of the portion of the frame is highly conserved. It is known that the amino acid sequence constituting CDR is incorporated into the frame region of other immunoglobulin molecules, which allows for grafting of the antigen-binding activity. The method in which the antigen-binding property of different immunoglobulins is grafted to human immunoglobulin by using this process has been established. As used herein, the term "antigen binding region" can comprise the CDR which is grafted to the frame. Therefore, the term "fragment comprising the antigen binding region" of a certain monoclonal antibody" comprises a fragment of human immunoglobulin comprising the variable region to which CDR of the monoclonal antibody is grafted. For example, each of the amino acid sequences of the above-mentioned variable regions comprises the following amino acid sequences (SEQ ID NOs) as CDRs.

|     | CDR1 | CDR2 | CDR3 |
| --- | --- | --- | --- |
| #11 heavy chain | SDYAWN (58) | YISYSGSTSYNPSLKSR (59) | SPPYYAMDY (60) |
| #11 light chain | KASQDVGTAVA (61) | WASTRHT (62) | QQYSSYPLT (63) |
| #17 heavy chain | SYWIH (64) | RIYPGTGSTYYNEKFKG (65) | YPTYDWYFDV (66) |
| #17 light chain | RASQSISNYLH (67) | YASQSIS (68) | QQSNSWPLT (69) |
| #37 heavy chain | SDYAWN (70) | YISYSGSTSYNPSLKSR (71) | ALPLPWFAY (72) |
| #37 light chain | KASQDVGTAVA (73) | WASTRHT (74) | QQYSSYPYT (75) |

Based on the information of the base sequence which encodes the above-mentioned amino acid sequences and the information of the base sequence which encodes the frame (FR) of human immunoglobulin, a primer can be designed and cDNA having a base sequence obtained by conjugating both of the base sequences can be amplified. The operation is repeated for each frame and a variable region in which CDR1, CDR2, and CDR3 of mice are connected by human FR can be constructed. Further, when the base sequence, which encodes a constant region of human immunoglobulin, is conjugated as needed, a humanized antibody with the constant region can be obtained.

As the chimeric antibody comprising the above-mentioned variable regions or a humanized antibody to which CDR constituting a variable region is grafted, an antibody with a constant region derived from IgG or IgM is comprised in a preferable antibody in the present invention. The present inventors confirmed that the monoclonal antibody against ILT7 showed CDC action on ILT7 expressing cells. Therefore, the antibody having a constant region derived from IgG or IgM exhibits cytotoxicity against ILT7 expressing cells due to CDC effect. Such antibodies are useful in inhibiting the number of ILT7 expressing cells such as IPCs.

The chimeric antibody capable of recognizing ILT7 or humanized antibody, which is provided by the present invention, can be produced by genetic engineering using polynucleotide encoding these antibodies. For example, a polynucleotide which is the base sequence described in the following SEQ ID NOs and encodes the amino acid sequence constituting a mature protein for each amino acid sequence can be used as a polynucleotide encoding the variable region

11 or #17. The consecutive amino acid sequence from 1 to C terminus for each amino acid sequence corresponds to a mature protein. In the case where each mature protein is expressed as a separate protein, it is preferable to place the secretion signal at the N terminus of each amino acid sequence. For example, in the amino acid sequences shown in these SEQ ID NOs, the amino acid sequence from N terminus to −1 can be used as a signal sequence when such proteins are expressed in animal cells. Alternatively, these variable regions can be secreted as mature proteins by using an arbitrary signal sequence which enables the secretion of immunoglobulin.

| | | |
|---|---|---|
| #11 | SEQ ID NO: 50 (base sequence) | SEQ ID NO: 52 (base sequence) |
| #17 | SEQ ID NO: 54 (base sequence) | SEQ ID NO: 56 (base sequence) |

In the same manner as described above, as for the polynucleotide encoding the humanized antibody, a polynucleotide which expresses the humanized antibody can be made by using the base sequence which encodes a protein having the signal sequence to be added to the N terminus. When heavy and light chains are carried on separate vectors, both vectors are co-transfected into the same host cell. The heavy and light chains expressed from each vector are used to construct an immunoglobulin molecule with both chains. Or, a polynucleotide encoding a heavy chain and a polynucleotide encoding a light chain can also be carried on the same vector. The host cell into which a vector carrying both polynucleotides is co-transfected expresses heavy and light chains and produces an immunoglobulin having both chains.

These polynucleotides can be expressed as antibodies using a host-vector system capable of expressing an antibody gene. Furthermore, in the case where they are expressed as a single protein molecule by connecting a heavy chain variable region with a light chain variable region, a signal sequence can be placed at the N terminus of the protein molecule. A known example of such an antibody molecule includes scFv molecule in which a heavy chain variable region and a light chain variable region are connected by a linker.

Each of the monoclonal antibodies thus produced is comprised in the monoclonal antibody of the present invention. In other words, a monoclonal antibody which consists of an immunoglobulin comprising the antigen binding region encoded by a polynucleotide derived from cDNA encoding the antigen binding region of the above-mentioned monoclonal antibodies is comprised in the monoclonal antibody in the present invention.

As described previously, RBL cells in which ILT1 gene was forced to be expressed could be used as an immunogen for obtaining ILT1 antibodies. However, the expression of ILT7 on the surface of RBL cells (P815) could not be confirmed and thus it could not be used as the immunogen. The present inventors found out that the expression of human ILT7 on the cell surface could be induced by the coexpression of human ILT7 and other cell membrane proteins which associate with human ILT7. Then, the present inventors found that the antibody, which binds to human IPCs, can be obtained by using the transformed cell whose expression is thus induced as an immunogen and completed the present invention.

That is, the present invention provides the immunogen for producing the antibody which binds to the extracellular domain of human ILT7, and comprises animal cells in which (a) a polynucleotide which encodes the amino acid sequence comprising the extracellular domain of human ILT7; and (b) a polynucleotide which encodes Fc receptor γ-chain are maintained so as to be exogenously expressed or cell membrane fractions thereof.

Six years or more have already passed since the structure of human ILT7 was found in 1998. However, the antibody capable of specifically recognizing ILT7 has still not been obtained. The antibody capable of recognizing human ILT7 was provided by using the immunogen of the present invention for the first time. That is, the present invention provided the antibody capable of recognizing human ILT7 which can be obtained by the following steps of:

(1) administering a cell which exogenously expresses a protein comprising extracellular domain of human ILT7 and a molecule which is associated with human ILT7 to immune animals;

(2) selecting an antibody producing cell which produces the antibody which binds to human ILT7 from antibody producing cells of the immune animals; and (3) culturing the antibody producing cells selected by step (2) and recovering an antibody capable of recognizing human ILT7 from the cultures.

It is found that human ILT7 is specifically expressed in human IPC. In the analysis of gene expression by SAGE which was performed by the present inventors, the specific expression of human ILT7 in human IPC was also confirmed. However, in the past reports, the expression levels of ILT7 of both cases were analyzed based on mRNA. Since the antibody capable of detecting human ILT7 was not provided, the expression state of protein was not analyzed conventionally. The analysis of human ILT7 protein was realized by the provision of the antibody which binds to the extracellular domain of human ILT7 in the present invention.

The present inventors actually confirmed that the monoclonal antibody which binds to the extracellular domain of human ILT7 based on the present invention specifically detected human IPCs. That is, the present invention relates to a method for detecting interferon producing cells which comprise the steps of: contacting a monoclonal antibody which binds to the extracellular domain of human ILT7 or a fragment comprising the antigen binding region with a test cell; and detecting the monoclonal antibody which is bound to cells or a fragment comprising its antigen binding region.

The detection of human ILT7 based on the present invention allows for determining whether a certain cell is IPC. That is, the present invention provides a method for identifying IPCs using human ILT7 as an indicator. Or, human IPCs can be separated by separating the cells in which human ILT7 was detected based on the present invention. That is, the present invention provides a method for separating IPCs using human ILT7 as an indicator.

Based on the analysis by human ILT7 antibody, it was confirmed that the expression level of ILT7 in IPCs whose differentiation was induced by CpG, and the like was reduced. That is, the IPCs before their differentiation is induced can be specifically detected by using ILT7 as an indicator. In other words, the monoclonal antibody of the present invention is useful, particularly in detecting IPCs before their differentiation into dendritic cells. As used herein, the term "IPCs before their differentiation" can be defined as cell populations which maintain the capacity to produce interferon.

In the present invention, the monoclonal antibody which binds to the extracellular domain of human ILT7 or the fragment comprising its antigen binding region can be labeled in advance. For example, antibodies can be easily detected by labeling with luminescent dyes or fluorescent dyes. More specifically, the fluorescent-dye labeled antibody is made to contact with a cell population which may comprise IPCs and then cells to which the antibody of the present invention bound can be detected by using the fluorescent dye as an indicator. Further, IPCs can be separated by separating the cells in which the fluorescent dye is detected. A series of the steps can be easily performed based on the principle of FACS.

Alternatively, the antibody of the present invention can be bound to a solid phase support such as magnetic particles in advance. The antibody bound to the solid phase support recognizes human ILT7 and then IPCs are trapped in the solid phase support. As a result, IPCs can be detected or separated.

The antibody necessary for the method for detecting IPCs based on the present invention can be provided as a reagent for detecting IPCs. That is, the present invention provides a reagent for detecting interferon producing cells, comprising the monoclonal antibody which binds to the extracellular domain of human ILT7 or the fragment comprising its antigen binding region. The reagent for detecting IPCs of the present invention can be used in combination with a positive control or a negative control in addition to antibodies. For example, the transformed cells which express the extracellular domain of human ILT7 and are used for the immunogen as well as the IPCs obtained from human can be used as the positive controls. Usually, only a few human IPCs can be obtained from the peripheral blood. Therefore, it is preferable to use, particularly a transformed cell as the positive control in the reagent of the present invention. On the other hand, an arbitrary cell, which does not express human ILT7, can be used as the negative control.

That is, the present invention provides a kit for detecting human IPCs which comprises:

(a) the monoclonal antibody which binds to the extracellular domain of human ILT7 or the fragment comprising its antigen binding region; and (b) the cell which expresses an exogenous protein comprising extracellular domain of human ILT7 and an exogenous molecule which is associated with human ILT7.

The present inventors analyzed the effect of the antibody which binds to the extracellular domain of human ILT7 on IPCs. As a result, it is confirmed that the antibody, which binds to the extracellular domain of human ILT7, inhibits the activity of IPCs. That is, the present invention relates to a method for inhibiting the activity of interferon producing cells, comprising a step of contacting any of the following components with interferon producing cells:

(a) a monoclonal antibody which binds to human ILT7 and inhibits the activity of interferon producing cells or a fragment comprising its antigen binding region; and (b) an immunoglobulin to which a complementarity-determining region of the monoclonal antibody described in (a) is grafted or a fragment comprising its antigen binding region.

Or, the present invention relates to a method for inhibiting the activity of interferon producing cells in living organisms, comprising a step of administering any of the following components to the living organisms:

(a) the monoclonal antibody which binds to human ILT7 and inhibits the activity of interferon producing cells or a fragment comprising its antigen binding region;

(b) a fragment comprising the immunoglobulin to which a complementarity-determining region of the monoclonal antibody described in (a) is grafted or a fragment comprising its antigen binding region; and (c) a polynucleotide which encodes the components described in (a) or (b).

As used herein, the term "Interferon Producing cells (IPCs)" means cells which have the ability to produce IFN and express ILT7 on the cell surface. Hereinafter, unless otherwise noted, the term "IPCs" encompasses net only cells which are precursor cells of dendritic cells but also the cells which have the ability to produce IFN and express ILT7 on the cell surface. Methods for identifying such IPCs are commonly known. IPCs can be distinguished from other blood cells using some cell surface markers as indicators. Specifically, a profile of cell surface markers of human IPCs is described below (Shortman, K. and Liu, Y J. Nature Reviews 2: 151-161, 2002). In recent years, a certain report has also suggested that BDCA-2 positive cell is defined as IPC (Dzionek, A. et al. J. Immunol. 165: 6037-6046, 2000).

[Profile of Cell Surface Antigens of Human IPCs]
CD4 positive, CD123 positive,
Lineage (CD3, CD14, CD16, CD19, CD20, CD56) negative, and CD11c negative Therefore, it can also be said that IPCs are cells which have the expression profile of these known markers and have the ability to produce IFN. Further, cells in living organisms with the ability to produce IFN are comprised in IPCs, even if the cells are a cell population with profiles different from the expression pattern of the expression profile of these markers. Further, examples of the characteristics, which are commonly seen in human IPCs, are as follows:

[Morphological Characteristic of Cells]
Similar to plasma cells
Round cells with a smooth cell surface
The nucleus is relatively large

[Functional Characteristic of Cells]
During virus infection, a large amount of Type-1 interferons are produced in a short period of time.
Differentiated into dendritic cells after virus infection.

As used herein, the term "inhibition of the activity of IPCs" means the inhibition of at least one of the functions of IPCs. Examples of the function of IPCs include the production of IFN and the cell survival. The cell survival can also be translated into the number of cells. Therefore, in the case of inhibiting both or either of these functions, it is said that the activity of IPCs is inhibited. It is found that type 1 IFN produced by IPCs leads to various diseases. Therefore, the inhibition of the number of IPCs and IFN production is useful for a medical treatment strategy of those diseases.

For example, the relationship between the pathological condition of autoimmune diseases and IFNα has been pointed out. Most of the IFNα is produced by IPCs. Therefore, pathological conditions caused by IFNα can be alleviated by inhibiting the production of IFNα. As used herein, the term "inhibition of IFN production by IPCs" means the inhibition of the production of at least one of the IFN produced by IPCs. Preferable IFN in the present invention is the type 1 IFN. Among them, IFNα is important.

That is, the present invention relates to an inhibitor of the production of IFN which comprises an antibody which binds to the extracellular domain of ILT7 as an active ingredient. Or, the present invention provides a method for inhibiting the production of IFN comprising a step of administering the antibody which binds to the extracellular domain of ILT7. Further, the present invention relates to the use of the antibody which binds to the extracellular domain of ILT7 in the production of a medicinal composition for inhibiting the production of IFN.

Cells in which a large amount of IFN is produced by a small number of cells are included in IPCs. For example, precursor cells of dendritic cells stimulated by viruses and the like produce most of the IFN produced by the living body. The inhibition of the number of IPCs which produce a lot of IFN results in suppressing the IFN production. Therefore, pathological conditions caused by IFNα can be reduced by inhibiting the number of IPCs. It was confirmed that anti-ILT7 monoclonal antibody bound to ILT7 expressing cells and then the effect of cytotoxicity was given by Complement Dependent Cytotoxicity (CDC) in a preferable embodiment of the present invention. CDC effect is one of the important mechanisms of antibody drug. The anti-ILT7 monoclonal antibody of the present invention also has potent cytotoxicity against ILT7 expressing cells such as IPCs due to CDC effect thereof. That is, as for the anti-ILT7 monoclonal antibody, the IFN production inhibiting effect can be expected by cytotoxicity against IPCs, in addition to the inhibition mechanism of IFN production in a preferable embodiment.

The antibody, which recognizes the extracellular domain of human ILT7 to be used for the present invention, can be obtained based on the method described previously. The antibody in the present invention may be of any class. Organism species from which the antibody is derived are not limited, either. Further, a fragment comprising the antigen binding region of antibody can be used as an antibody. For example, an antibody fragment comprising the antigen binding region which is obtained by enzymatic digestion of IgG can be used as the antibody in the present invention. Specifically, antibody fragments such as Fab and F(ab')$_2$ can be obtained by digestion with papain or pepsin. It is well known that these antibody fragments can be used as antibody molecules which have affinity for antibodies. Alternatively, antibodies constructed by genetic recombination can also be used as long as satisfactory antigen-binding activity is maintained. Examples of the antibodies constructed by genetic recombination include chimeric antibodies, CDR-transplanted antibodies, single chain Fvs, diabodies, linear antibodies, and polyspecific antibodies formed of antibody fragments. It is common knowledge that these antibodies can be given by using monoclonal antibodies.

In the present invention, antibodies can be modified, if necessary. According to the present invention, the antibody, which recognizes the extracellular domain of human ILT7, has an inhibiting effect on the activity of IPCs. That is, it is contemplated that the antibody itself has cytotoxicity against IPCs. Subclasses of antibodies which exhibit potent effector activity are known. Alternatively, the inhibiting effect on the IPC activity can be further enhanced by modifying antibodies with a cytotoxic agent. Examples of the cytotoxic agent are described below.

Toxins: *Pseudomonas* Endotoxin (PE), diphtheria toxin, ricin
Radioisotopes: $Tc^{99m}$, $Sr^{89}$, $I^{131}$, $Y^{90}$
Anticancer agents: calicheamicin, mitomycin, paclitaxel Toxins consisting of proteins can be conjugated to antibodies or their fragments with a bifunctional reagent. Alternatively, a gene encoding toxin is connected to a gene encoding antibody and fusion proteins of genes can also be obtained. The method for conjugating antibodies with radioisotopes is also known. For example, the method for labeling antibodies with radioisotopes using a chelating agent is known. Furthermore, the anticancer agents can be conjugated to antibodies using sugar chains or the bifunctional reagent.

The present inventors have confirmed a phenomenon in which a monoclonal antibody which is bound to ILT7 expressed on a cell membrane is incorporated into cells after binding (internalization). Therefore, the cytotoxic agents can be delivered into cells by contacting antibodies conjugated with these cytotoxic agents of the present invention with ILT7 expressing cells. That is, the present invention provides an active inhibitor of ILT7 expressing cells which comprises anti-ILT7 monoclonal antibody to which the cytotoxic agent is conjugated as an active ingredient. Or, the present invention relates to the use of anti-ILT7 monoclonal antibody to which the cytotoxic agent is conjugated in the production of the active inhibitor of ILT7 expressing cells. Further, the present invention provides a method for inhibiting the activity of ILT7 expressing cells comprising a step of administering anti-ILT7 monoclonal antibody to which the cytotoxic agent is conjugated.

In the present invention, an antibody whose structure is artificially modified can also be used as an active ingredient. For example, various modification methods are known in order to improve the cytotoxicity and stability of antibodies. Specifically, an immunoglobulin in which sugar chains of heavy chains are modified is known (Shinkawa, T. et al. J. Biol. Chem. 278:3466-3473. 2003). Antibody Dependent Cell-mediated Cytotoxicity (ADCC) activity of immunoglobulin was enhanced by the modification of sugar chains. Or, an immunoglobulin in which the amino acid sequence of Fc region is modified is also known. That is, ADCC activity was enhanced by artificially increasing the binding activity of immunoglobulin to Fc receptor (Shield, R L. et al. J. Biol. Chem. 276; 6591-6604, 2001).

IgG, which is bound to Fc receptor, is incorporated in cells once. Then, IgG binds to Fc receptor which is expressed in endosome and it is released into blood again. This phenomenon has been revealed. IgG with a high binding activity with Fc receptor has a better chance of being released into blood again after its incorporation into cells. As a result, the retention time of IgG in blood is extended (Hinton, P R. et al. J Biol. Chem. 279: 6213-6216. 2004). In addition to this, it is said that modification of amino acid sequence of Fc region causes a change of complement dependent cytotoxicity (CDC) activity. These modified antibodies can be used as the antibody in the present invention.

When the antibody, which binds to the extracellular domain of human ILT7, is contacted to IPCs, the activity of IPCs is inhibited. Therefore, these antibodies can be used for an inhibitor or method for inhibiting the activity of IPCs. That is, the present invention provides an active inhibitor of IPCs which comprises at least one component selected from the group consisting of the following (a) to (c) as an active ingredient. Or, the present invention relates to a method for inhibiting the activity of IPCs comprising a step of administering at least one component selected from the group consisting of the following (a) to (c). Further, the present invention relates to the use of at least one component selected from the group consisting of the following (a) to (c) in the production of active inhibitor of IPCs:

(a) the monoclonal antibody which binds to human ILT7 or a fragment comprising its antigen binding region;

(b) the immunoglobulin to which a complementarity-determining region of the antibody described in (a) is grafted or a fragment comprising its antigen binding region; and (c) a polynucleotide which encodes components described in (a) or (b).

In the present invention, the monoclonal antibody, which recognizes the extracellular domain of human ILT7, can be used as the monoclonal antibody which inhibits the activity of IPCs. In the present invention, one or more monoclonal antibodies can be used. For example, one or more monoclonal antibodies, which recognize the extracellular domain of human ILT7, are blended to use in the present invention.

It can be confirmed that antibodies have an inhibiting effect on IFN production by IPCs in the manner as described below. IPCs produce a large amount of IFN due to virus stimulation. Antibodies are given to IPCs before, after, or at the same time as the stimulation of IPCs with viruses. The capacity to produce IFN each for the resulting IPCs is compared to that of each control to which antibodies are not given. The ability to produce IFN can be evaluated by measuring IFNα or IFNβ contained in culture supernatant of IPCs. As a result of the comparison, it can be confirmed that the tested antibodies are effective in inhibiting the ability to produce IFN when the amount of IFN in the supernatant is significantly decreased by the addition of antibodies. These methods for measuring IFN are known. IPCs produce most of the IFN in the living body. Therefore, IFN producing state in the living body can be regulated by inhibiting the ability to produce IFN of IPCs.

In the present invention, the activity of IPCs encompasses the maintenance of the number of IPCs. Therefore, the inhibition of the activity of IPCs in the present invention comprises the inhibition of the number of IPCs. When it is confirmed that the number of IPCs is inhibited under the presence of antibodies, it can be found that the antibodies are inhibiting the activity of IPCs. As with IFN production, an inert immunoglobulin derived from the same animal species as the antibody whose activity should be confirmed can be used as a comparative control. The number of IPCs can be quantitatively compared by counting cells. The number of cells can be counted with FACS or a microscope.

Further, it is said that IPCs are differentiated into cells which induce Th2 referred to as dendritic cell 2 (DC2) as a result of infection with virus or the like. If IFN production of IPCs by virus stimulation can be inhibited, their differentiation into Th2 may also be inhibited. Therefore, it can be expected that the monoclonal antibody of the present invention, which inhibits IFN production, may also have a therapeutic effect on various allergic diseases.

When the antibody, which recognizes the extracellular domain of human ILT7, is administered to a host different from organism species from which the antibody is derived, it is desirable to process the antibody into a shape which is hard to be recognized as a foreign substance by the host. For example, immunoglobulin cannot be easily recognized as the foreign substance by processing the antibody into the following molecules. The technique for processing immunoglobulin molecules as described below is known. Fragment comprising the antigen binding region which lacks a constant region (Monoclonal Antibodies: Principles and Practice, third edition, Academic Press Limited. 1995; Antibody Engineering, A Practical Approach, IRL PRESS, 1996)

Chimeric antibody composed of the antigen binding region of monoclonal antibody and the constant region of immunoglobulin of the host ("Gene Expression Experiment Manual", Isao Ishida, Tamie Ando, eds., Kodansha, 1994)

CDR-substituted antibody in which complementarity-determining region (CDR) of immunoglobulin of the host is substituted to CDR of monoclonal antibody ("Gene Expression Experiment Manual", Isao Ishida, Tamie Ando, eds., Kodansha, 1994)

Alternatively, a human antibody can be obtained by using non-human animals into which a human antibody gene is incorporated as immune animals, while the non-human animals are used. For example, transgenic mice with human antibody genes have been put to practical use in order to produce human antibodies as immune animals (Ishida et al., Cloning and Stem Cells, 4:85-95, 2002). The use of such animals allows for obtaining the human antibody which recognizes ILT7 using immunogens as described previously. It is preferable to administer human antibody to humans.

Alternatively, a human immunoglobulin variable region gene can also be obtained by a phage display method (McCafferty J. et al., Nature 348:552-554, 1990; Kretzschmar T et. al., Curr Opin Biotechnol. 2002 December; 13(6): 598-602). In the phage display method, a gene encoding human immunoglobulin variable region is incorporated into a phage gene. A phage library can also be produced by using various immunoglobulin genes as sauces. A phage expresses a variable region as a fusion protein of the protein composed of the phage. The variable region expressed by the phage on the phage surface maintains the binding activity with an antigen. Therefore, phages, which bind to antigens or cells in which antigens are expressed, are selected, thereby allowing for screening a phage in which a variable region having the desired binding activity is expressed from the phage library. Further, a gene encoding a variable region, which has the desired binding activity, is retained in the phage particles thus selected. That is, in the phage display method, a gene encoding a variable region with the desired binding activity can be obtained by using the binding activity of the variable region as an indicator.

In the active inhibitor of IPCs or the method for inhibiting the activity of IPCs in the present invention, the antibody which recognizes the extracellular domain of human ILT7 or the antibody fragment which comprises at least the antigen binding region of the antibody can be administered as a protein or a polynucleotide encoding the protein. In administration of polynucleotides, it is desirable to use a vector in which a polynucleotide encoding the desired protein is placed under the control of an appropriate promoter so as to express the desired protein. An enhancer and a terminator can also be placed in the vector. A vector which carries a gene of heavy and light chains which constitutes an immunoglobulin and is able to express an immunoglobulin molecule is known.

The vector capable of expressing the immunoglobulin can be administered by introducing into cells. In the administration to living organisms, a vector, which can be infected with cells by administering to the living organisms, can be administered directly. Once lymphocytes are separated from the living organisms, then the vector is introduced into the lymphocytes, which can be returned to the living organisms again (ex vivo).

In the active inhibitor of IPCs or the method for inhibiting the activity of IPCs based on the present invention, as for the amount of monoclonal antibody to be administered to the living organisms, immunoglobulin is administered usually in the range of 0.5 mg to 100 mg, for example, 1 mg to 50 mg, preferably 2 mg to 10 mg per kg of body weight. Intervals of administration of the antibody to living organisms can be properly adjusted so as to maintain an effective concentration of immunoglobulin in the living organisms during the period of treatment. Specifically, for example, the antibody can be administered at intervals of 1 to 2 weeks. The administration route is optional. Those skilled in the art can properly select an effective administration route in treatments. Specific examples thereof include oral or parenteral administration. Antibodies are administered systemically or topically for example, by intravenous injection, intramuscular injection, intraperitoneal injection, subcutaneous injection, or the like. Examples of an appropriate formulation for parenteral administration in the present invention include injectable solutions, suppositories, and sprays. When the antibody is given to cells, immunoglobulin is added to culture medium usually in the range of 1 µg/ML, preferably 10 µg/ML, more preferably 50 µg/ML, further preferably 0.5 mg/ML.

In the active inhibitor of IPCs or method for inhibiting the activity of IPCs of the present invention, the monoclonal antibody can be administered to living organisms by optional methods. Usually, the monoclonal antibody is blended with a pharmaceutically acceptable support. If necessary, the monoclonal antibody can be blended with additive agents such as thickeners, stabilizers, preservatives, and solubilizers. Examples of such a support or additive agent include lactose, citric acid, stearic acid, magnesium stearate, sucrose, starch, talc, gelatin, agar, vegetable oil, and ethylene glycol. The term "pharmaceutically acceptable" means approved by a regulatory agency in each government or listed in the Pharmacopeia in each country or other generally recognized pharmacopeia for use in animals, in mammalians, and more particularly, in humans. The active inhibitor of IPCs of the present invention can also be provided in the form of single or multiple doses of lyophilized powders or tablets. Further, the lyophilized powders or tablets can be used in combination with sterilized water for injection, physiological salt solution or buffer solution for dissolving the compositions so as to be a desired concentration before administration.

Further, when the monoclonal antibody is administered as a vector, which expresses immunoglobulin, heavy and light chains are co-transfected to another plasmid and each plasmid can be administered in the range of 0.1 to 10 mg, for example, 1 to 5 mg per kg of body weight. In order to introduce the plasmids into cells in vitro, the content of the vectors for use is 1 to 5 μg/$10^6$ cells. Herein below, the present invention will be specifically described with reference to Examples.

All prior art documents cited herein are incorporated by reference in their entirety.

EXAMPLES

Example 1

A. Analysis of Expression of ILT7

A-1) Analysis Using SAGE Library

The expression of genes in human monocytes, IPCs, and HSV-treated IPCs was compared and analyzed by Serial Analysis of Gene Expression (Trade name; SAGE) method. The analysis method is as follows. Monocytes were separated as BDCA-4 positive cells and IPCs were separated as CD14 positive cells from human peripheral blood using a cell sorter. Further, IPCs were cultured for 12 hours under the presence of Herpes Simplex Virus (HSV) and then the differentiated IPCs were prepared. RNAs were obtained from respective cells, followed by producing a SAGE library using I-SAGE (Trade name) kit (manufactured by Invitrogen). Data on the obtained base sequences of about 100,000 tags was analyzed using SAGE Analysis Software (manufactured by Invitrogen). As a result, a gene whose score value of monocyte/IPC/IPC+HSV is 0/16/0, namely, ILT7 (Gen Bank Acc#NM_012276) known as a gene, which shows IPC specific expression, was found. ILT7 is a membrane protein with immunoglobulin-like domains encoded by a base sequence shown in SEQ ID NO: 1 (FIG. 2 (a)). It has been reported that mRNA of ILT7 is expressed in IPCs (Blood 100, 3295-3303 (2002)).

A-2) RT-PCR

The expression of ILT7 in hemocyte cells was examined in more detail. Each cell was preparatively isolated from human peripheral blood by the cell sorter. RNAs were extracted from each of the isolated cell populations, from which cDNA was synthesized. Quantitative PCR was performed in accordance with an ordinary method using the resulting cDNA as a template and the expression level of mRNA of ILT7 was analyzed. The used conditions for the base sequences of primers and PCR are as follows:

```
                                         (SEQ ID NO: 3)
Forward primer: 5'  CTC CAA CCC CTA CCT GCT GTC 3'

(SEQ ID NO: 4)
Reverse primer: 5'  TTC CCA AGG CTC CAC CAC TCT 3'
```

1 cycle of PCR (at 94° C. for 3 minutes)
25 cycles of PCR [at 94° C. for 30 seconds, at 58° C. for 30 seconds, and at 72° C. for 1 minute]
1 cycle of PCR (at 72° C. for 6 minutes)

Figure 1B:
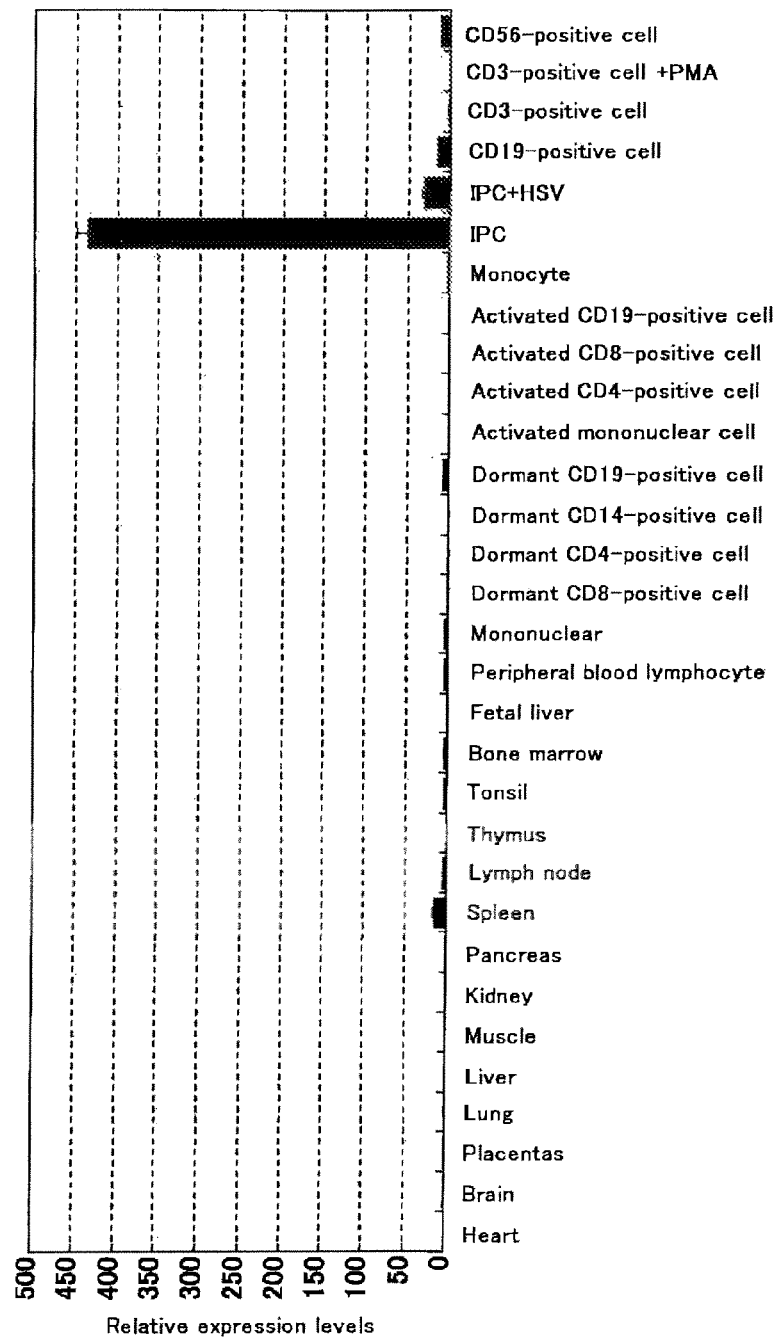
FIG. 1b is a diagram in which the expression of mRNA of ILT7 gene in various human tissues and cells is compared and examined using quantitative PCR method. The horizontal axis shows the examined tissues and cells and the vertical axis shows the expression level of ILT7, which is standardized according to the expression level of GAPDH gene.

When IPCs stimulated by monocytes, IPCs, HSVs, and CD19 positive cells (i.e. B cells), CD3 positive cells (i.e. T cells), T cells stimulated by PMAs, and CD56 positive cells (i.e. NK cells) were examined, it was found that ILT7 was expressed specifically in IPCs (FIG. 1 (a)).

A-3) Quantitative RT-PCR

Further, the expression in other organs and tissues was examined by quantitative PCR using ABI PRISM 7000 (manufactured by Applied Biosystem). As cDNA panel, BD (Trade name) MTC multiple tissue cDNA panel (Human I; Cat. No. 636742, Human immune; Cat. No. 636748, Human blood fractions; Cat. No. 636750; all of them are manufactured by Becton Dickinson) and the same cDNA derived from hemocyte cells as described in 2) were used.

The used base sequences of primers are as follows:

```
Forward primer for ILT7:
                                         (SEQ ID NO: 5)
5' CCT CAA TCC AGC ACA AAA GAA GT 3'

Reverse primer for TLT7:
                                         (SEQ ID NO: 6)
5' CGG ATG AGA TTC TCC ACT GTG TAA 3'

Forward primer for GAPDH:
                                         (SEQ ID NO: 7)
5' CCA CCC ATG GCA AAT TCC 3'

Reverse primer for GAPDH:
                                         (SEQ ID NO: 8)
5' TGG GAT TTC CAT TGA TGA CAA G 3'
```

PCR was performed by using ABI PRISM 7000 (manufactured by Applied Biosystem) and SYBR green PCR master mix kit (manufactured by the same company). Sequence Detection System Software (manufactured by the same company) was used for analysis.

The reaction conditions are as follows:

Step 1: 1 cycle of PCR (at 50° C. for 2 minutes)

Step 2: 1 cycle of PCR (at 95° C. for 10 minutes)

Step 3: 40 cycles of PCR (at 95° C. for 15 seconds, at 60° C. for 1 minute)

The expression of ILT7 gene was compared between each tissue by standardizing at the level of expression of the glyceraldehyde-3-phosphate dehydrogenase (GAPDH) gene, which is known to be expressed constitutively. As a result, it was observed that ILT7 was not expressed in any organs other than lymphoid tissues and expressed specifically in IPCs.

B. Production of ILT7 and FcRγ Expression Vectors

Subsequently, cloning of genes and production of expression vectors were carried out in order to express ILT7 proteins.

B-1) Cloning of ILT7 Genes

Poly (A) $^+$RNA separated from human peripheral blood was extracted from IPCs, from which cDNA was synthesized using oligo dT primer and Super Script Choice System for cDNA Synthesis kit. An EcoRI adapter was ligated into the synthesized cDNA, which was ligated into pME18S vector cleaved by EcoRI, resulting in production of human IPC cDNA library. ILT7 gene was amplified by PCR method using the produced cDNA library as a template as well as using primers with the following base sequences. 1 unit of KOD Plus DNA polymerase (manufactured by TOYOBO CO., LTD.) was used for PCR reaction. Reaction conditions were set to 25 cycles of PCR [at 94° C. for 15 seconds, at 55°

C. for 30 seconds, and at 68° C. for 2 minutes] after 1 cycle of PCR at 94° C. for 2 minutes.

```
Forward primer:
                                    (SEQ ID NO: 9)
5' CAG GGC CAG GAG GAG GAG ATG 3'

Reverse primer:
                                    (SEQ ID NO: 10)
5' TCA GCA GAC ACT TCC CCA ACT 3'
```

2-kb ILT7cDNA d was separated and recovered by electrophoresis using 1% agarose gel, which was cloned to pCR4 Blunt-TOPO plasmid vector (manufactured by Invitrogen) using Zero Blunt TOPO PCR Cloning kit (manufactured by Invitrogen). The base sequences of the genes obtained was analyzed, and it was found that the desired ILT7 gene shown in SEQ ID NO: 1 was obtained.

B-2) Production of FLAG-Tagged ILT7 Expression Vectors

A plasmid expressing a protein in which FLAG tags were fused to N- and C-termini of ILT7, respectively was constructed. ILT7 was fused with a tag, which allowed for confirming the expression of ILT7 protein by detection of the tag. The desired sequence was amplified by PCR method using the ILT7 gene produced as described in 1) as a template as well as using primers with the following base sequences. 1 unit of KOD Plus DNA polymerase (manufactured by TOYOBO CO., LTD.) was used for PCR reaction. Reaction conditions were set to 25 cycles of PCR [at 94° C. for 15 seconds, at 55° C. for 30 seconds, and at 68° C. for 2 minutes] after 1 cycle of PCR at 94° C. for 2 minutes.

```
For N-FLAG ILT7
Forward primer (SEQ ID NO: 11):
5' CCG ctc gag ATG ACC CTC ATT CTC ACA AGC

CTG CTC TTC TTT GGG CTG AGC CTG GGC [GAT TAC

AAG GAT GAC GAC GAT AAG] CCC AGG ACC CGG GTG

CAG GCA GAA 3'

Reverse primer (SEQ ID NO: 12):
5' C TAG act agt TCA GAT CTG TTC CCA AGG CTC

3'

For C-FLAGILT7
Forward primer (SEQ ID NO: 13):
5' CCG ctc gag ATG ACC CTC ATT CTC ACA AGC 3'

Reverse primer (SEQ ID NO: 14):
5' C TAG act agt TCA [CTT ATC GTC GTC ATC CTT

GTA ATC] GAT CTG TTC CCA AGG CTC 3'
```

In the above-mentioned base sequences, each underlined portion in parentheses shows a base sequence encoding the attached FLAG tag and each lowercase letter shows the cleavage site for the restriction enzyme XhoI or SpeI. DNA fragments amplified by PCR were cleaved by XhoI and SpeI, which were then separated by Gel electrophoresis. 2 kb DNA fragments were recovered, which were ligated into pME18X vector cleaved by XhoI and SpeI in the same manner as described above. Then, two types of plasmids capable of expressing the desired fusion protein, i.e. pME18X-N-FLAG ILT7 and pME18 X-C-FLAG ILT7 were constructed, respectively.

B-3) Cloning of FcRγ Genes

FcRγ protein was considered as a protein capable of associating with ILT7 protein. The present molecule is a gene with base sequences and amino acid sequences of SEQ ID NO: s 15 and 16 (Genbank Acc#NM_004106, J. Biol. Chem. 265, 6448-6452 (1990)). The molecule is a molecule (γ chain) which constitutes FcεRI, i.e. a high affinity IgE receptor. Although it is also named as FcεRIγ, it will be referred to as FcRγ hereinafter. In this regard, the present molecule has also been known as a component of FcγR or FcαR. The present gene was cloned by PCR method as shown below to produce expression vectors. FcRγ gene was amplified by PCR method using the human IPC cDNA library produced as described in 1) as a template as well as using primers with the following base sequences. 1 unit of KOD Plus DNA polymerase (manufactured by TOYOBO CO., LTD.) was used for PCR reaction. Reaction conditions were set to 25 cycles of PCR [at 94° C. for 15 seconds, at 55° C. for 30 seconds, and at 68° C. for 1 minute] after 1 cycle of PCR at 94° C. for 2 minutes.

```
Forward primer:
                                    (SEQ ID NO: 17)
5' CCC AAG ATG ATT CCA GCA GTG 3'

Reverse primer:
                                    (SEQ ID NO: 18)
5' GGA AGA ACC AGA AGC CAA AGA 3'
```

The 0.3-kb FcRγcDNA fragment amplified was separated and recovered by electrophoresis using 2% agarose gel, which was cloned to pCR4 Blunt-TOPO plasmid vector (manufactured by Invitrogen) using Zero Blunt TOPO PCR Cloning kit (manufactured by Invitrogen). The base sequences of the genes obtained were analyzed, and it was confirmed that the desired FcRγ gene shown in SEQ ID NO: 15 was cloned.

B-4) Production of Myc-Tagged FcRγ Expression Vectors

A plasmid expressing a protein in which Myc tag was attached to C terminus was constructed so that the expression of FcRγ protein could be confirmed. The desired sequence was amplified by PCR method using the FcRγ gene produced as described in 3) as a template as well as using primers with the following base sequences. 1 unit of KOD Plus DNA polymerase (manufactured by TOYOBO CO., LTD.) was used for PCR reaction. The conditions were set to 25 cycles of PCR [at 94° C. for 15 seconds, at 55° C. for 30 seconds, and at 68° C. for 1 minute] after 1 cycle of PCR at 94° C. for 2 minutes.

```
Forward primer (SEQ ID NO: 19):
5' CCG ctc gag ATG ATT CCA GCA GTG GTC TTG 3'

Reverse primer (SEQ ID NO: 20):
5' CTA Gac tag tCT A[CA GAT CCT CTT CAG AGA

TGA GTT TCT GCT C]CT GTG GTG GTT TCT CAT G 3'
```

Of the above-mentioned primer sequences, the underlined portion in parentheses shows a base sequence encoding the attached Myc tag and each lowercase letter shows the cleavage site for the restriction enzyme XhoI or SpeI. DNA fragments amplified by PCR were cleaved by XhoI and SpeI, which were then separated by Gel electrophoresis. About 0.3-kb DNA fragments were recovered, which were ligated into pME18X vector cleaved by XhoI and SpeI in the same manner as described above. Then, a plasmid capable of expressing the desired fusion protein, i.e. pME18X-Myc-FcRγ was constructed.

C. Expression of ILT7 in Animal Cells

The expression of ILT7 in animal cells was examined using expression vectors produced as described above.

C-1) Expression in 293T Cells

Figure 3:
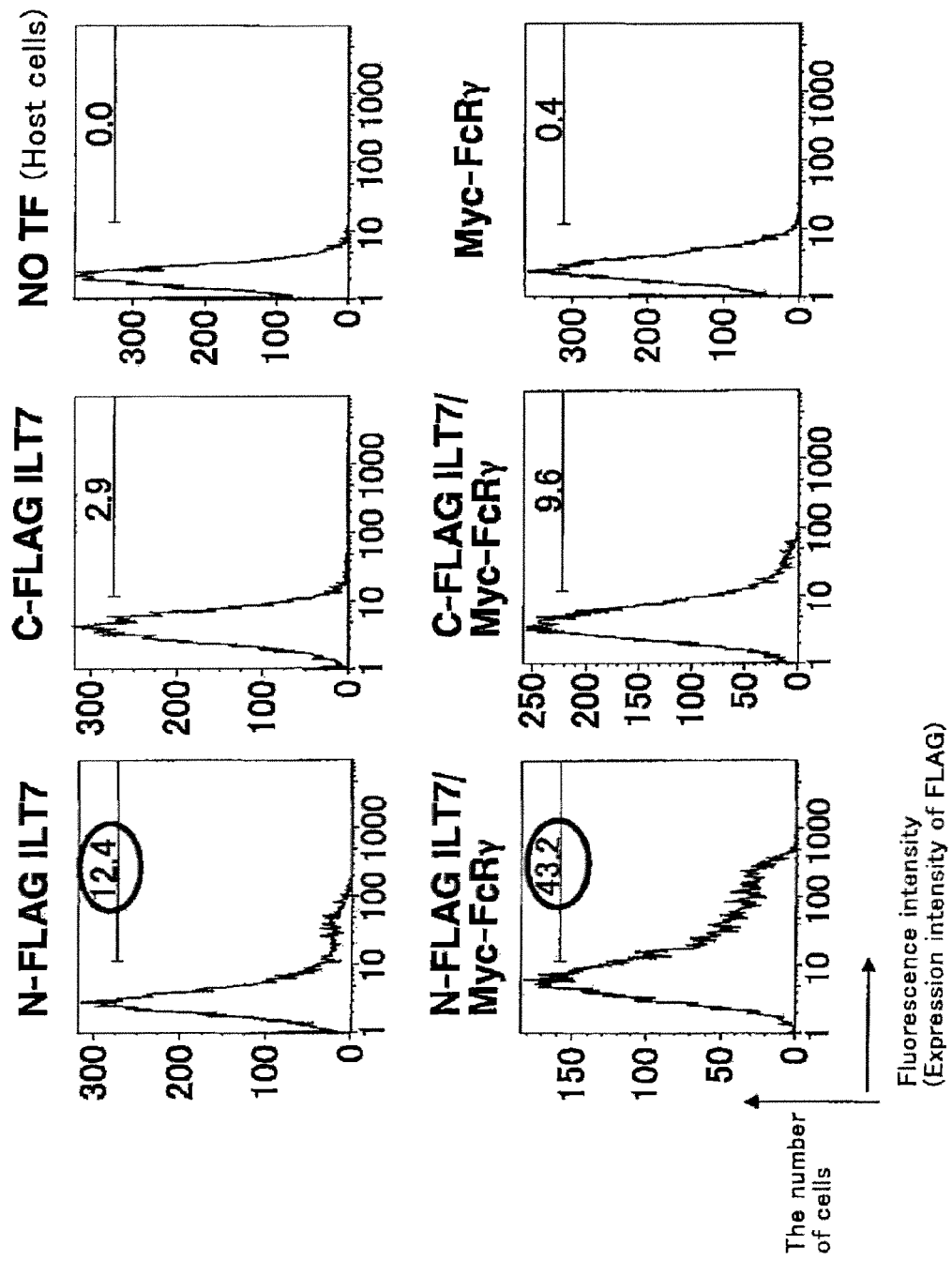
FIG. 3 is a diagram showing a result that ILT7 expression vector and FcRγ expression vector were introduced into cells and the cell-surface expression of ILT7 molecules was examined by FCM. The horizontal axis shows the fluorescence intensity detected in anti-FLAG antibody, namely, the intensity of cell-surface expression of ILT7 molecules to which FLAG tag was attached and the vertical axis shows the number of cells.

DNAs consisting of the following five combinations were introduced into 293T cells (7×10$^5$ cells) using effectene transfection kit (manufactured by Qiagen). Two days after the introduction, flow cytometry analysis (FCM analysis) was carried out.
(1) pME18X-N-FLAG ILT7 2 μg
(2) pME18X-C-FLAG ILT7 2 μg
(3) pME18X-N-FLAG ILT7 1 μg+pME18X-Myc-FcRγ 1 μg
(4) pME18X-C-FLAG ILT7 1 μg+pME18X-Myc-FcRγ 1 μg
(5) pME18X-Myc-FcRγ 2 μg The method of FCM analysis was performed in the same manner as described in A-4 of the following Example 2. Cy3 conjugated anti-Flag antibody (manufactured by Sigma) was used for the reaction and FACScan (manufactured by Becton Dickinson) was used for the analysis. As a result, it was found that only a few ILT7 was expressed on the cell surface when reacted alone, while ILT7 was expressed extracellularly and robustly when coexisted with FcRγ (FIG. 3). It is known that mouse FcRγ has high homology with human FcRγ. However, when p815 cells (mouse mastocytoma) which express mouse FcRγ were used as hosts, the expression of ILT7 could not be observed.

C-2) Analysis by Immunoprecipitation and Western Blotting Method

Figure 4:
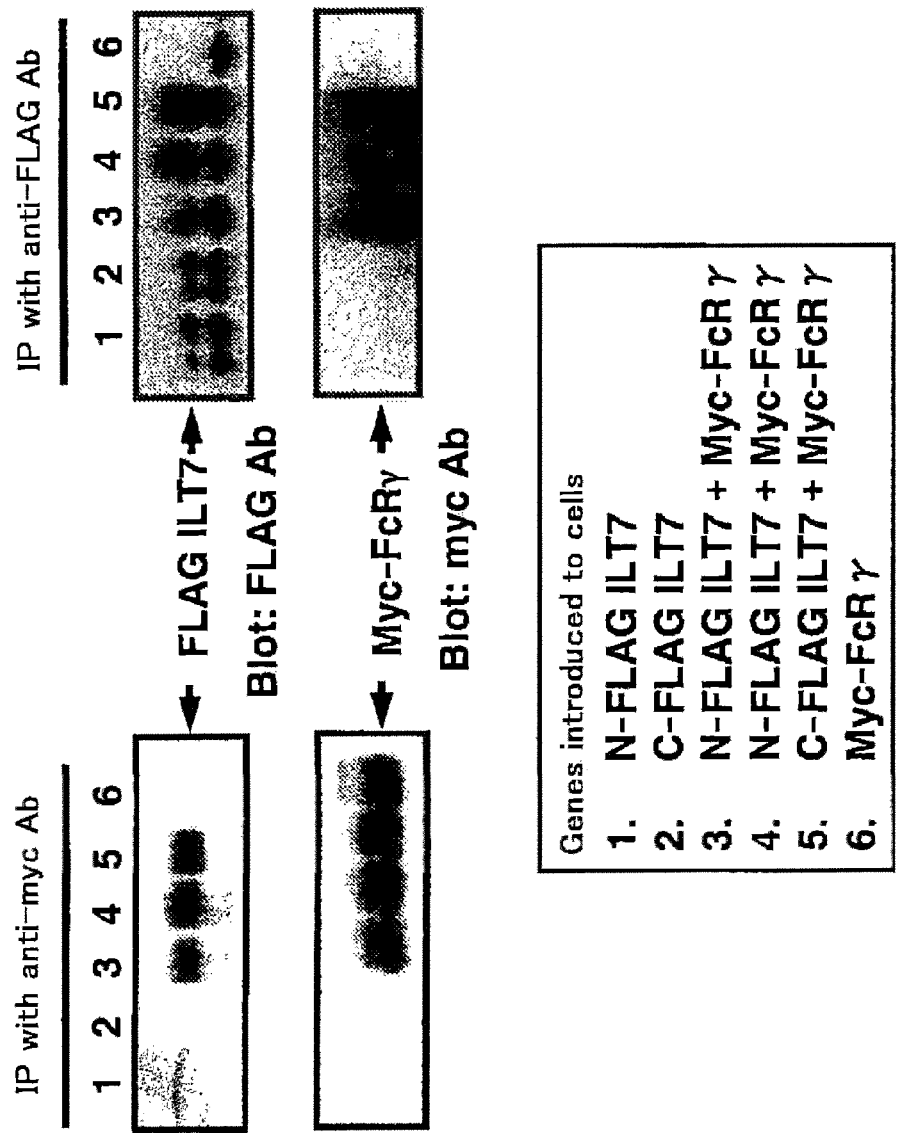
FIG. 4 shows photographs in which ILT7 expression vector and FcRγ expression vector were introduced into cells and the association of molecules was analyzed by immunoprecipitation and Western blotting. The left side diagrams show results that ILT7 molecule was blotted with anti-FLAG antibody after immunoprecipitating FcRγ molecule with anti-myc antibody (the drawing above) and FcRγ molecule was blotted with anti-myc antibody (the drawing below). Similarly, the right side diagrams show results that ILT7 molecule was blotted with anti-FLAG antibody after immunoprecipitating FcRγ molecule with anti-FLAG antibody (above) and FcRγ molecule was blotted with anti-myc antibody (below).

ILT7 was expressed with accompanying FcRγ on the cell surface, which was confirmed as follows. After immunoprecipitation, various antibodies for each 293T cell which was coexpressed with both genes in respective combinations described in (1) to (5) were analyzed. DNAs were introduced into 293T cells (7×10$^5$ cells), from which 293T cells were recovered two days after the introduction in the same manner as described in 1). Cell fractionations were dissolved in lysis buffer (0.5% Triton, 150 mM Nacl), which was left on ice for 20 minutes. Thereafter, aspiration using a needle (27G) was repeated several times, followed by centrifuging at 15 Krpm for 20 minutes. Anti-myc antibody (2 μg, manufactured by Santa cruz biotechnology) or anti-Flag antibody (2 μg, manufactured by Sigma) was added to 200 μg of lysate of the resulting products, which was further stirred by rotation at 4° C. for 4 hours. Then, Protein A/G Sepharose 4 Fast Flow mix (manufactured by Amersham bioscience) was added thereto, which was stirred by rotation at 4° C. for 1 hour. Then, the resulting precipitated fractions were washed with lysis buffer with the following composition 3 times.

lysis buffer:
0.5% TritonX-100,
50 mM HEPES (pH 7.6),
150 mM NaCl,
1 mM EDTA,
10% glycerol,
1 mM DTT,
2 mM PMS F,
1 μg/ml Aprotinin,
1 μg/ml Leupeptin,
1 μg/ml Pepstatin A,
0.1 μg/ml Chymostazin,
1 mM Na$_3$VO$_4$,
0.1 mM β-glycerophosphate A sample buffer for SDS-PAGE was added to the washed precipitates, which was boiled for 5 minutes and centrifuged, followed by performing electrophoresis with 10% SDS gel. Samples were transferred from gels after electrophoresis to PVDF membrane (Immobilon-p-transfer membrane: manufactured by Millipore) in accordance with an ordinary method. Blotting was performed with anti-Flag antibody and anti-myc antibody. It was confirmed that the ILT7 associated with FcRγ was present in 293T cells because their presence in each immune precipitate was observed (FIG. 4).

C-3) Analysis of Sugar Chain

Since several bands of ILT7 were observed in the Western analysis, the possibility that ILT7 was glycosylated was examined. 200 μg of lysate of 293T cells which express N-FLAG ILT7 and Myc-FcRγ was immunoprecipitated with anti-Flag antibody in the manner as described in 1) and 2). Thereafter, the precipitated fractions were suspended in 60 μL of N-glycosidase buffer with the following composition and 30 μL of each resulting solution was aliquoted into two tubes.

N-glycosidase buffer:
10 mM EDTA,
0.2% SDS,
0.5% TritonX 100,
1% 2-mercaptoethanol in PBS (phosphate buffer)

Figure 5:
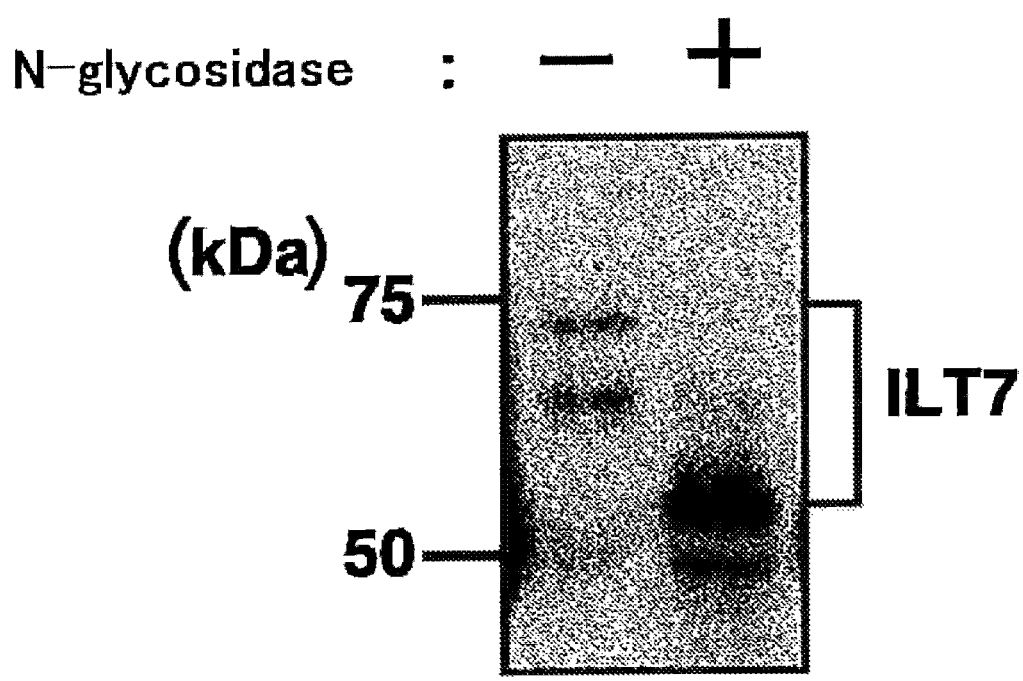
FIG. 5 is a photograph in which glycosylation of ILT7 molecule was examined by introduction of ILT7 expression vector and FcRγ expression vector into the cell and N-glycosidase treatment. The left side of the photograph shows the size of ILT7 in the case where ILT7 was not treated with N-glycosidase and the right side of the photograph shows the size of ILT7 in the case where N-glycosidase treatment was performed.

Then, 3 units of 3 μL of N-glycosidase (#1365177, manufactured by Roche) were added to one tube, which was reacted at 37° C. for 15 hours. Further, 7 μL of sample buffer was added thereto, which was heated at 100° C. for 5 minutes, followed by performing electrophoresis with 10% SDS gel. After electrophoresis, gel was transferred to PVDF membrane, to which 1 μg of anti-ILT7 polyclonal-antibody as described in 4) was added and reacted at 4° C. overnight. The resulting product was washed with TBS-T buffer and reacted with 100,000-fold diluted HRP-labeled anti-rabbit antibody (manufactured by Jackson) at room temperature. Then, it was colored with ECL Western Blotting Detection System (manufactured by Amersham bioscience). As a result, the apparent molecular weight was decreased by performing N-glycosidase treatment. Thus, it was expected that sugar chains were added to ILT7 (FIG. 5).

C-4) Production of Anti-ILT7 Polyclonal Antibody

The used anti-ILT7 polyclonal antibody as described in 3) was produced as follows. Peptide of 23 amino acids corresponding to C terminus of ILT7 (CSQEANSRKDNAP-FRVVEPWEQI; SEQ ID NO: 21) was chemically synthesized and bound to KLH protein which is a career, and the resulting product was used as an immunogen. Rabbits were intradermally immunized with immunogen mixed with Freund complete adjuvant. After six immunizations in all (once per week), the increased antibody titer in serum was confirmed and then whole blood was collected. Then, some serum was affinity purified using peptide column of the same sequence. The resulting product was determined as anti-ILT7 polyclonal antibody.

Example 2

A. Production of Anti-ILT7 Monoclonal Antibody

A-1) Production of Immunogen

Cells to be used as immunogens were prepared by introducing genes to 293T cells as described below. 46.4 μg of transgene (pME18 X-C-FLAG ILT7 23.2 μg and pME18X-Myc-FcRγ 23.2 μg) was added to the bottom of 100 mm/Collagen Coated Dish (IWAKI) coated with 3 mL of opti-MEM (GIBCO) and mixed. Subsequently, aside from the transgene solution, 58 μL of Lipofectamine (Trade name) 2000 (Invitrogen) was diluted with 3 mL of opti-MEM, which was allowed to stand at room temperature for 5 minutes and Lipofectamine solution was prepared. Thereafter, Lipofectamine solution was gently added to the dish containing the transgene solution and mixed. After standing at room temperature for 20 minutes, 10 mL of 293T-cells, diluted to $1×10^6$ cells/ML using DMEM culture medium (SIGMA) containing 10% FBS (fetal bovine serum), was gently added to the dish. The resulting medium was subjected to static culture in an incubator at 37'C under $CO_2$ for 48 hours, from which cells were recovered by pipetting. The obtained cells were used as transfectants for immunogens.

A-2) Production of Hybridomas

On the day before cells were immunized, 50 μL of emulsion obtained by mixing 200 μL of PBS with 200 μL of complete adjuvant (FREUND) (RM606-1, manufactured by Mitsubishi Kagaku Iatron, Inc.) was injected to the bottoms of both feet of four Balb/c female mice (four-week-old) for immunization. On the following day, 50 μL of $2×10^7$ cells suspended in 400 μL of PBS was immunized. The second and third immunizations were performed every four days. Three days following the third immunization, cell fusion was performed as follows. Cells were collected from lymph nodes of mice feet immunized. Mouse myeloma cells P3-X63-Ag8-U1 cultured in RPMI1640 culture medium (SIGMA) containing 10% FBS were mixed with the cells derived from lymph nodes and myeloma so that the ratio of the mouse myeloma cells to the cells derived from lymph nodes and myeloma should be 2:1 to 10:1, from which cells were recovered by centrifugation. PEG4000 (MERCK) equivalently diluted with RPMI1640 culture medium was added to the obtained cell fractions, which was subjected to cell fusion. After washing cells, the resulting product was suspended in 160 mL of 15% FBS-HAT-medium containing a supplement and then inoculated into sixteen 96-well plates at 200 μL/well. The culture medium was exchanged after three days. One to two weeks after observation of the colony formation, primary screening was performed.

A-3) Screening of Hybridoma by Cell ELISA Method

Hybridoma, which produces target antibody, was screened by the following Cell ELISA. The produced cells as described in 1) were used at $1×10^7$ cells per 96-well plate, which were suspended in 0.5% BSA/2 mM EDTA/PBS and then aliquoted to a plate for Cell ELISA (NUNC 249570 96V NW PS) at 100 μL/well. Centrifugation was carried out at 2,000 rpm at 4° C. and then the supernatant was discarded. Sampled culture supernatant was added at 50 μL/well, which was reacted at room temperature for 30 minutes. Washing operation that involves adding 0.5% BSA/2 mM and EDTA/PBS to each well, centrifuging at 2,000 rpm at 4° C. for 2 minutes, and then discarding the supernatant was carried out twice. 50 μL/well of 10,000-fold diluted peroxidase-labeled goat anti-mouse IgG antibody (IM0819; Beckman coulter) was added to each well after washing, which was reacted for 30 minutes. The washing operation using 0.5% BSA/2 mM-EDTA/PBS was carried out twice, followed by adding a coloring solution. The prepared antibody solution was substituted with PBS (−) by a dialysis membrane (10,000 cuts manufactured by PIERCE) to give purified anti-ILT7 chimeric antibodies.

A-4) Examination of Antibody Responsiveness by Flow Cytometry (FCM) Analysis

Hybridoma culture supernatant was analyzed by flow cytometry (FCM) analysis. The produced cells as described in 1) was suspended in 0.5% BSA/2 mM EDTA/PBS, which was transferred into a centrifugal tube at $1×10^5$ per one sample, followed by adding 40 μL of each culture and reacting at room temperature for 30 minutes. Washing operation that involves adding 1 ml of 0.5% BSA/2 mM and EDTA/PBS to each tube, centrifuging at 1200 rpm at 4° C. for 3 minutes, and discarding the supernatant was carried out twice. 40 μL of 100-fold diluted FITC-labeled goat anti-mouse IgG antibody (IM0819; Beckman coulter) was added to each well after washing, which was reacted at room temperature for 30 minutes. The washing operation using 0.5% BSA/2 mM-EDTA/PBS was carried out twice, followed by analyzing using flow cytometry FC500 (Beckman coulter). A hybridoma producing an antibody which did not respond to only host cell and responded specifically to the cell into which gene had been introduced was selected. The selected hybridoma was cloned by the limiting dilution method and hybridomas #11 and #17 which produce monoclonal antibodies were obtained.

B. Examination of Responsiveness of Anti-ILT7 Antibody

Figure 6A:
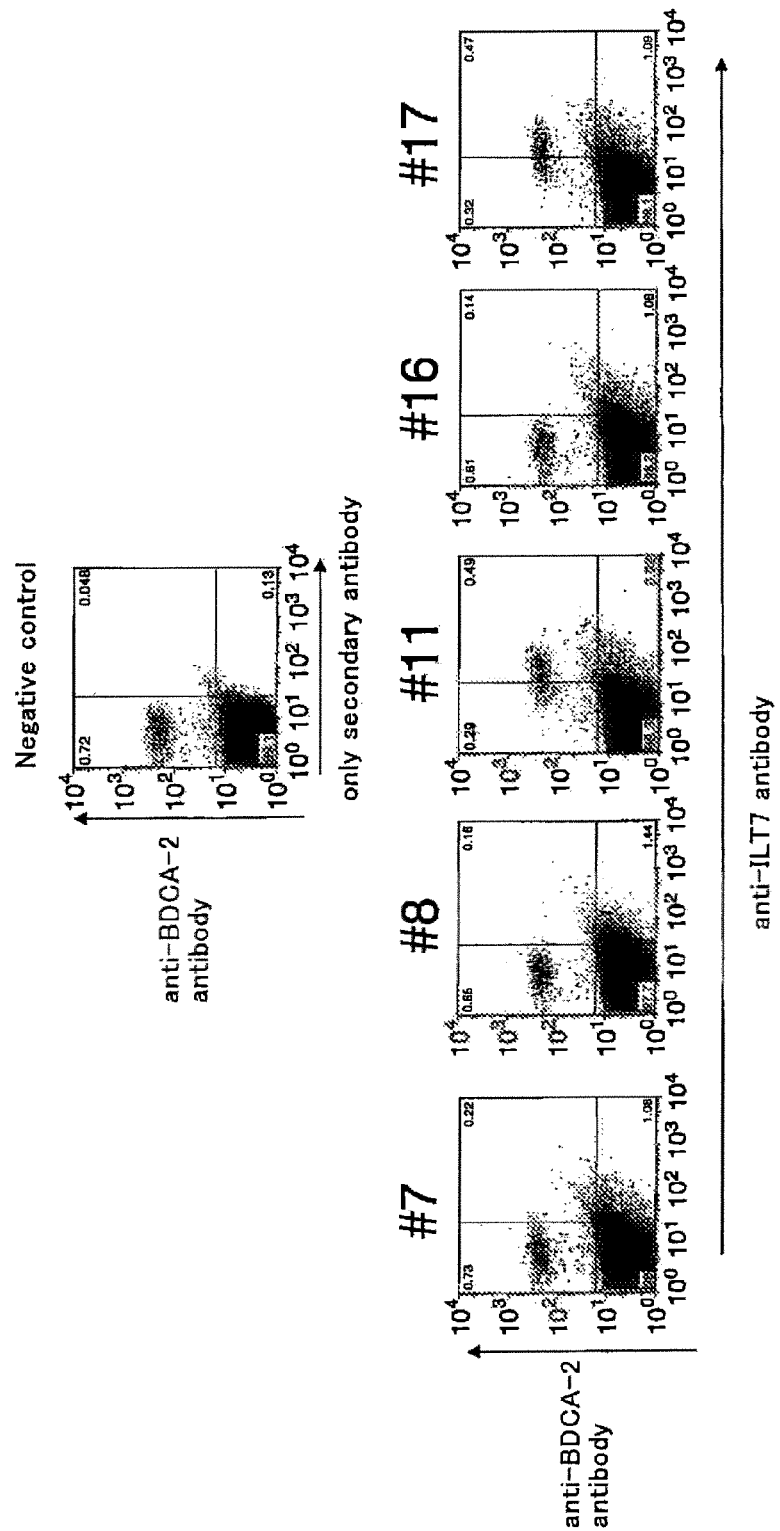
FIG. 6a is a diagram in which the responsiveness of the produced anti-ILT7 monoclonal antibody was examined by FCM analysis. (a) shows a result that binding of anti-ILT7 antibody to IPC fraction of BDCA-2 positive was analyzed by using human peripheral blood lymphocytes and double staining with the anti-ILT7 antibody and anti-BDCA-2 antibody. The vertical axis shows the responsiveness to BDCA-2 antibody and the horizontal axis shows the responsiveness to each of the produced anti-ILT7 antibodies.
Figure 6B:
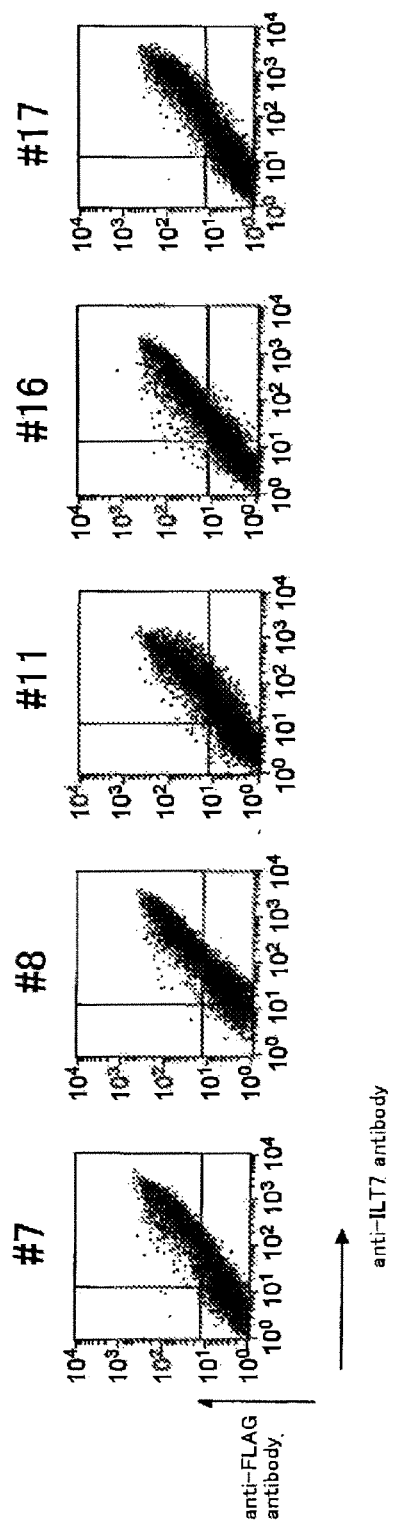
FIG. 6b is a diagram in which the responsiveness of the produced anti-ILT7 monoclonal antibodies was examined by FCM analysis. (b) shows a result in which binding of anti-ILT7 antibody to ILT7 molecule was examined by using 293T cells into which ILT7 and FcRγ expression vectors had been introduced. The vertical axis shows the responsiveness of anti-FLAG antibody, namely, the intensity of expression of ILT7 molecules to which FLAG tag was attached and the horizontal axis shows the responsiveness of respective anti-ILT7 antibodies.

ILT7 in which FLAG tag was attached to N terminus was coexpressed with FcRγ molecule in 293T cells in the same manner as described in C-1) of Example 1. Then, the responsiveness of the antibody obtained Example 2 was confirmed analysis using FACScan (Becton Dickinson). As a result, it was confirmed than all antibodies produced by hybridomas #11 and #17 which were obtained as described in A responded to the cells into which ILT7 gene was introduced and which expressed ILT7 (FIG. 6 (*b*)). Further, lymphocytes were separated from human peripheral blood using Ficoll and then double staining with the produced anti-ILT7 antibody and PE-labeled anti-BDCA-2 antibody (Miltenyi) was performed. Then, the responsiveness to the lymphocytes was examined. As a result, the binding of monoclonal antibody produced by hybridomas #11 and #17 to BDCA-2 positive cell was detected. That is, it was confirmed that both monoclonal antibodies recognized ILT7 molecules expressed on human IPCs (FIG. 6 (*a*)). These monoclonal antibodies were designated as anti-ILT7 antibody #11 and anti-ILT7 antibody #17, respectively. More detailed analysis was performed.

Figure 7:
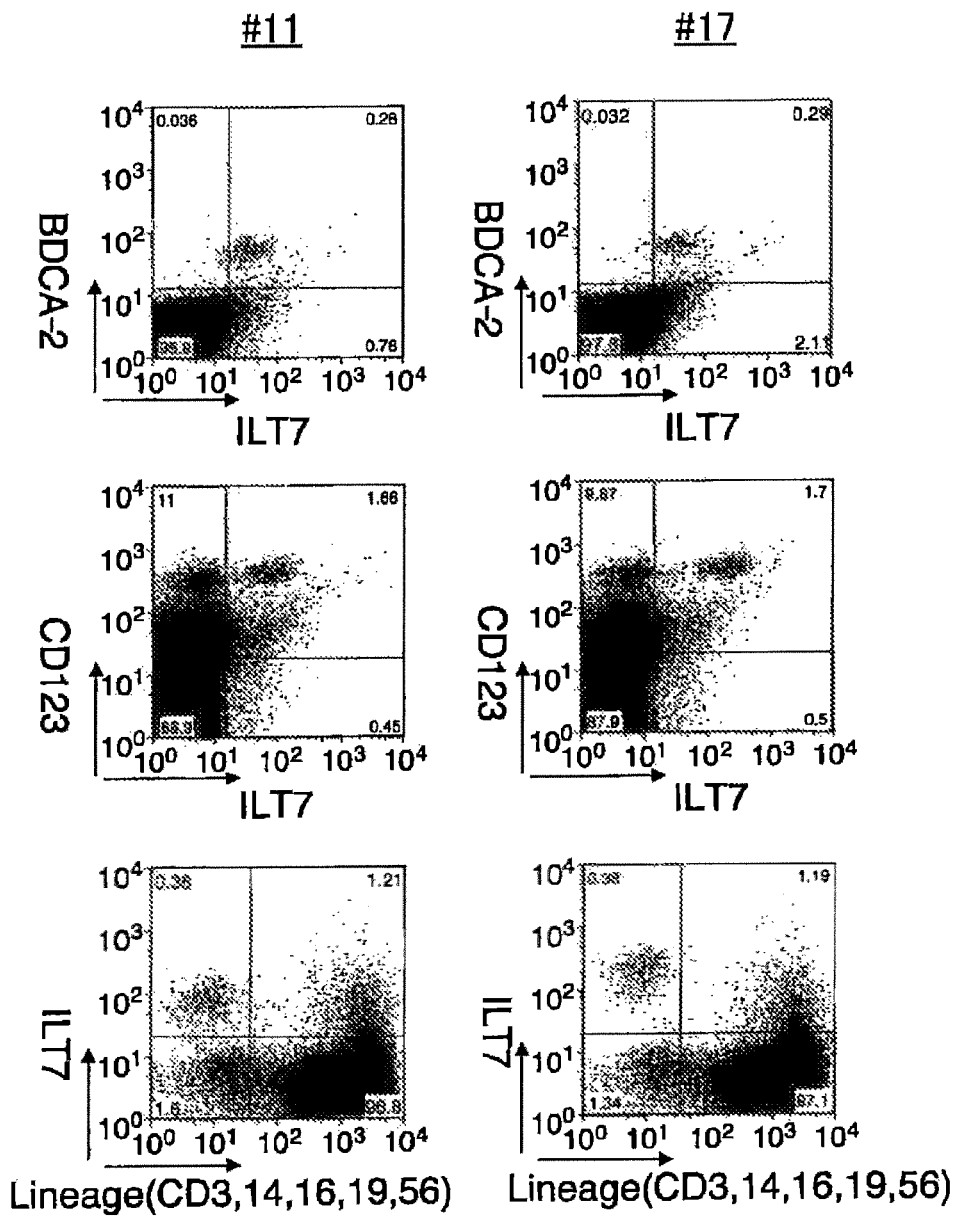
FIG. 7 is a diagram in which among the produced anti-ILT7 monoclonal antibodies, the responsiveness of two clones to human peripheral blood lymphocytes was examined by FCM analysis. Three graphs on the left shows the results of #11 and three graphs on the right shows the results of #17. In the left side diagrams, each axis with the mark of ILT7 shows the responsiveness of ILT7#11. Similarly, in the right side diagrams, each axis with the mark of ILT7 shows the responsiveness of ILT7#17.

Multiple-staining analysis for human peripheral blood lymphocytes was carried out using the produced anti-ILT7 antibody, anti-Lineage-1 antibody (anti-CD3, CD14, CD16, CD19, CD56 antibodies; Becton Dickinson), anti-CD123 antibody (Becton Dickinson), and anti-BDCA-2 antibody (Miltenyi). As for ILT7 antibody-positive fractions, Lineage Marker was negative, CD123 was positive, and BDCA-2 was positive. From the results, it was confirmed that IPCs were stained by only ILT7#11 and ILT7#17 (FIG. 7).

Figure 8:
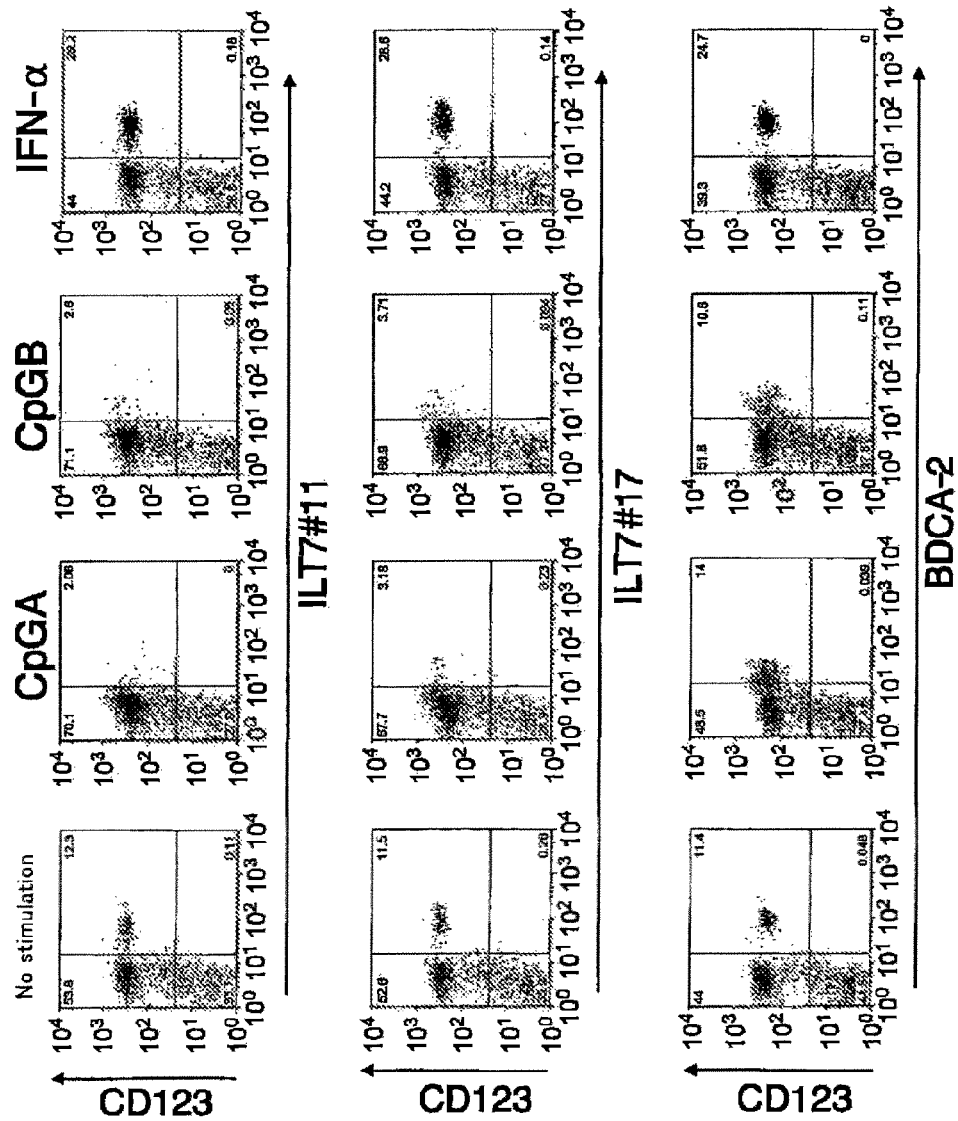
FIG. 8 is a result in which binding activity of the produced anti-ILT7 monoclonal antibodies ILT7#11 and ILT7#17 to human lymphocytes was compared with that of anti-BDCA-2 antibody and examined. The vertical axis shows the responsiveness of anti-CD123 antibody and the horizontal axis shows the responsiveness of each antibody. That is, each antibody binds to a portion of CD123 positive cell. It is a diagram showing the results in which the responsiveness was analyzed when lymphocyte cells were stimulated by two kinds of CpGs and IFNα.

Further, the expression of various molecules was examined by FCM analysis when human peripheral blood lymphocytes were stimulated by CpG or IFNα for 24 hours. CpGODN2216 was used as CpGA, which induces the production of IFN from IPCs and CpGODN2006, was used as CpGB which facilitates the maturation of dendritic cells (Moseman et al. J. Immunology. 173, 4433-4442, 2004). A gate was set to Lineage Marker negative fraction. When the responsiveness of anti-BDCA-2 antibody and anti-ILT7 antibody to CD123 positive cell population was analyzed, most of the ILT7 positive fractions were disappeared even after 24-hours CpG stimulation. On the other hand, some cells of BDCA-2 showed positive after 24-hours CpG stimulation (FIG. 8). It has been considered that IPCs are differentiated into different cells immediately after the CpG stimulation. It was indicated that the anti-ILT7 antibody of the present invention was useful as a stage specific antibody to IPCs. Further, it was confirmed that IPCs in peripheral blood lymphocytes were not differentiated under the presence of IFNα, in this case where the survival ratio was high, the expression of ILT7 was maintained on IPCs, further ILT7 was stably present on IPCs in autoimmune diseases with the possibility that IFN in serum was at a high level.

C. Examination of Specificity of Anti-ILT7 Antibody

Figure 9A:
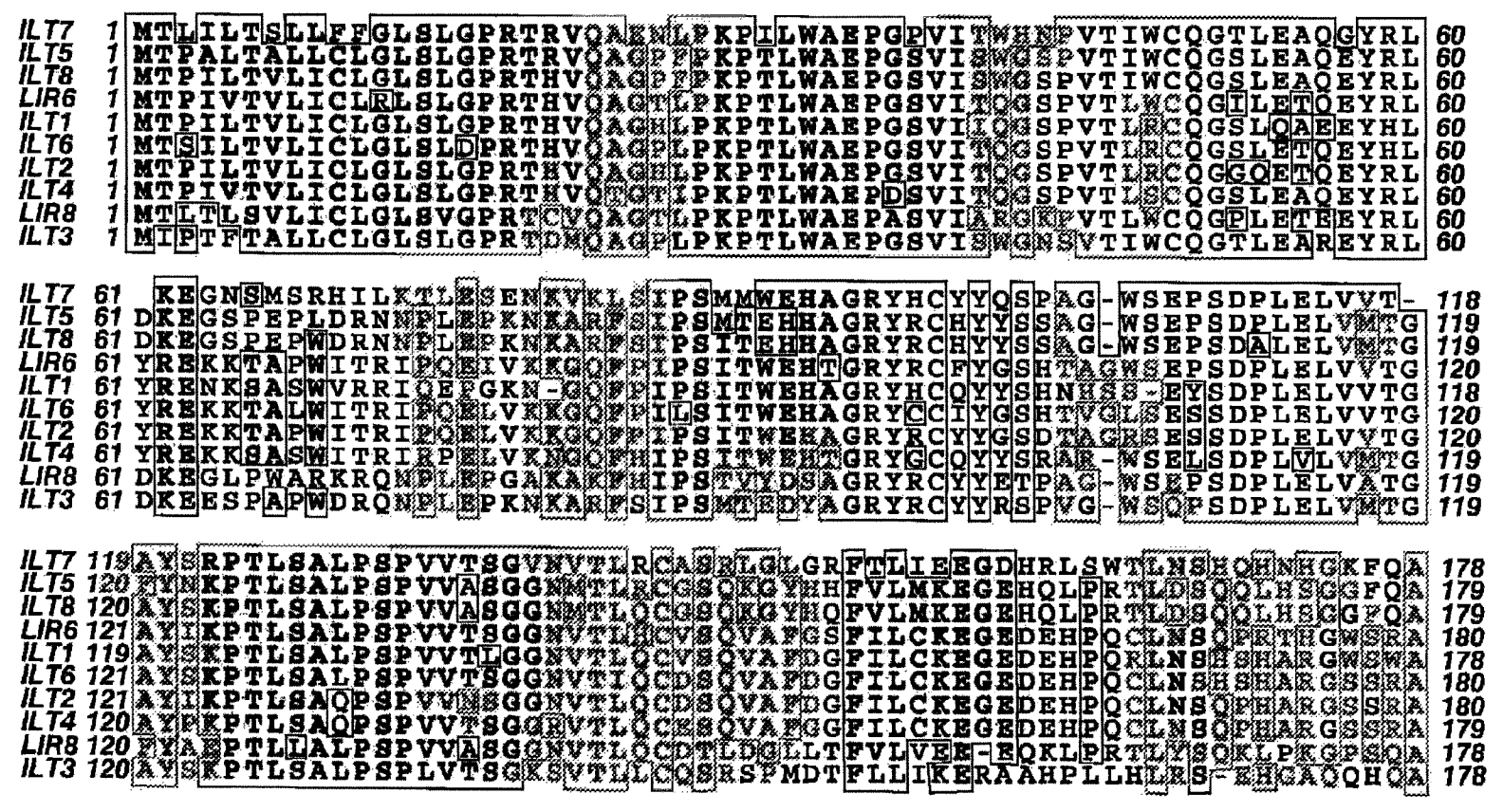
Figure 9B:
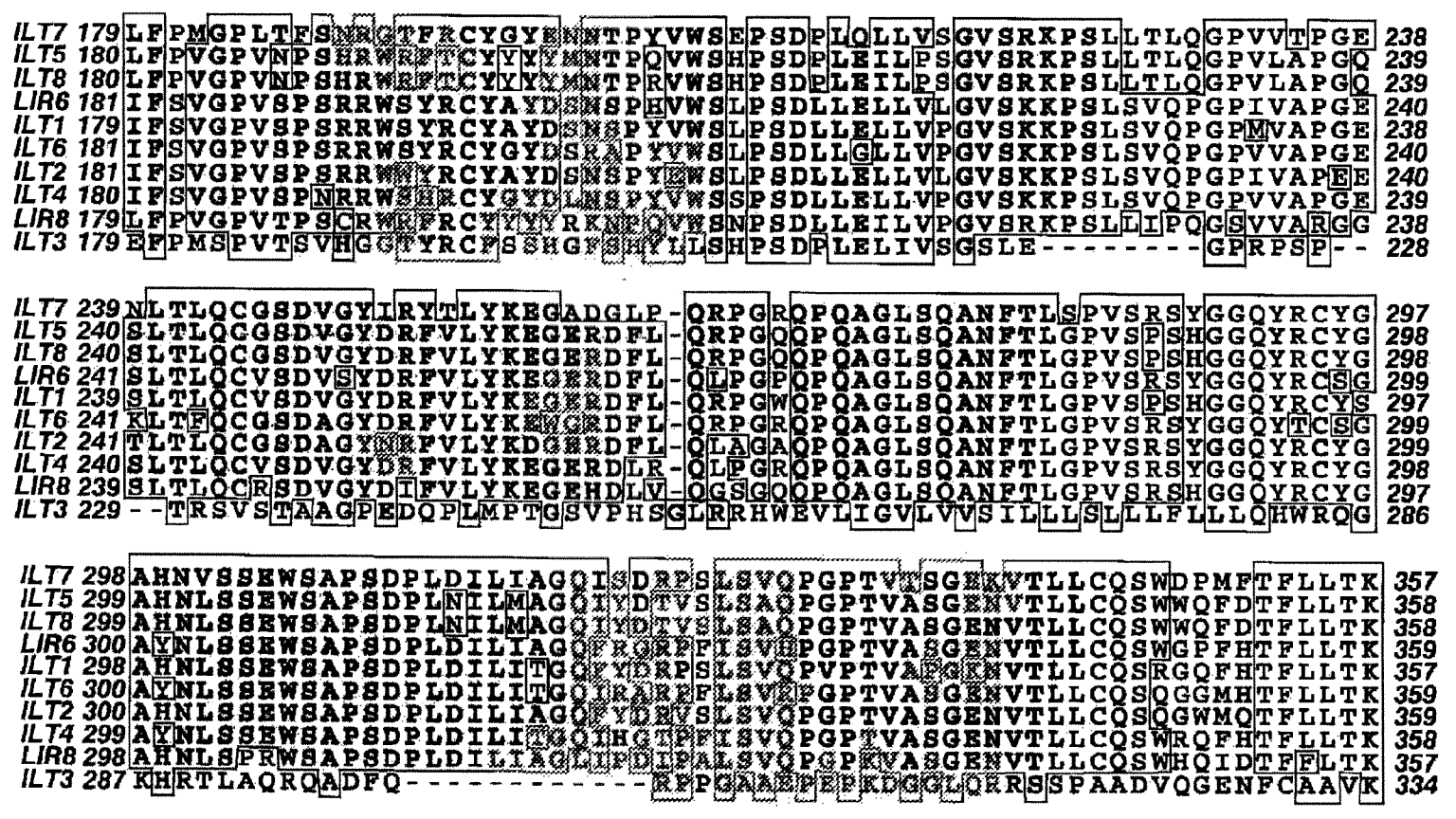
Figure 9C:
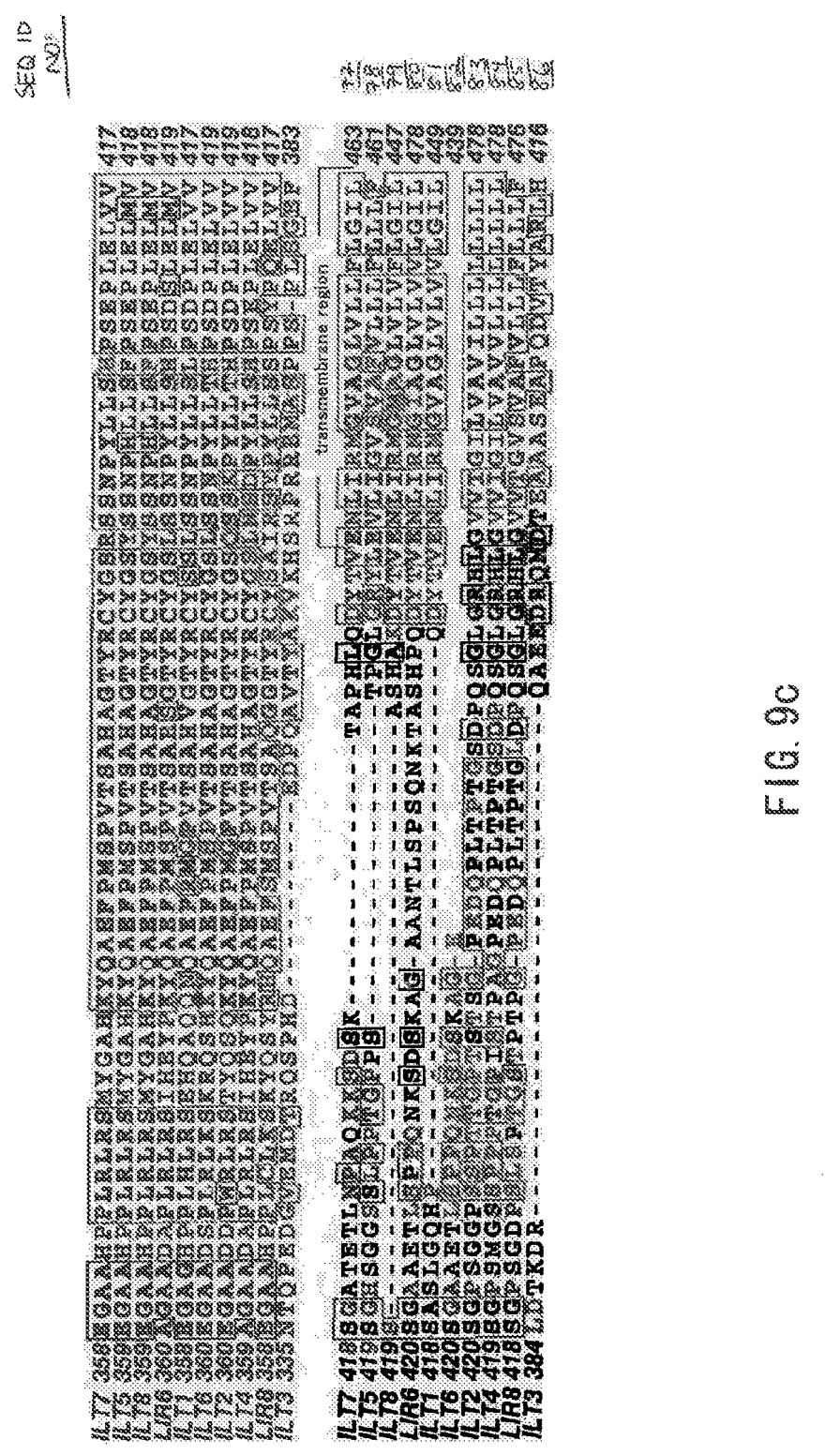

ILT7 belongs to ILT/LIR family and there is a plurality of molecules with high homology, particularly with high homology in the extracellular region (FIG. 9). It has been reported that mRNAs of molecules, especially such as ILT2 and ILT3 are expressed in IPCs (Ju et al. Gene 331, 159-164, 2004). Therefore, the responsiveness of these molecules was confirmed using transgenic cells.

C-1) Cloning of ILT1 Molecule and Production of Expression Vectors cDNA was synthesized from RNA derived from human tonsil using oligo dT primer and SuperScript Choice System for cDNA Synthesis kit. Next, a NotI adapter was ligated into pME18S vector cleaved by NotI, resulting in production of human tonsil cDNA library.

ILT1 gene with a FLAG tag at the C terminus was amplified by PCR method using the produced cDNA library as a template as well as using primers with the following base sequences. 1 unit of KOD Plus DNA polymerase (manufactured by TOYOBO CO., LTD.) was used for PCR reaction. Reaction conditions were set to 25 cycles of PCR [at 94° C. for 15 seconds, at 55° C. for 30 seconds, and at 68° C. for 2 minutes] after 1 cycle of PCR at 94° C. for 2 minutes.

```
Forward primer (SEQ ID NO: 22):
5' CCG ctc gag ATG ACC CCC ATC CTC ACG GTC C
3'

Reverse primer (SEQ ID NO: 23):
5' CTA Gac tag tTC A[CT TAT CGT CGT CAT CCT

TGT AAT C]CC TCC CGG CTG CAT CTT G 3'
```

In the above-mentioned primer sequences, the underlined portion in parentheses shows a base sequence encoding the attached FLAG tag and each lowercase letter shows the cleavage site for the restriction enzyme XhoI or SpeI. DNA fragments amplified by PCR were cleaved by XhoI and SpeI, whim were then separated by Gel electrophoresis. About 2-kb DNA fragments were recovered, which were ligated into pME18X vector cleaved by XhoI and SpeI in the same manner as described above. Then, a plasmid capable of expressing the desired fusion protein, i.e. pME18X-C-FLAGILT1 was constructed. The base sequence and amino acid sequence are shown in SEQ ID NO: s: 24 and 25.

C-2) Production of Expressing Cells and Examination of Antibody Responsiveness

As for ILT2 (SEQ ID NO: 26) and ILT3 (SEQ ID NO: 28), expression vectors in which respective genes were cloned to XbaI or XhoI sites of pcDNA4.1 (manufactured by Invitrogen) were used. DNAs of the following combinations were introduced into 293T cells ($7 \times 10^5$ cells) in the same manner as described in C-1). Two days after the introduction, FCM analysis was carried out and then anti-ILT7 antibody was analyzed.

(1) pME18X-N-FLAG ILT7 1 μg+pME18X-Myc-FcRγ 1 μg
(2) pME18X-C-FLAG ILT1 0.5 μg+pME18X-Myc-FcRγ 0.5 μg+pcDNA4.1-ILT2 0.5 μg+pcDNA4.1-ILT3 0.5 μg

Figure 10:
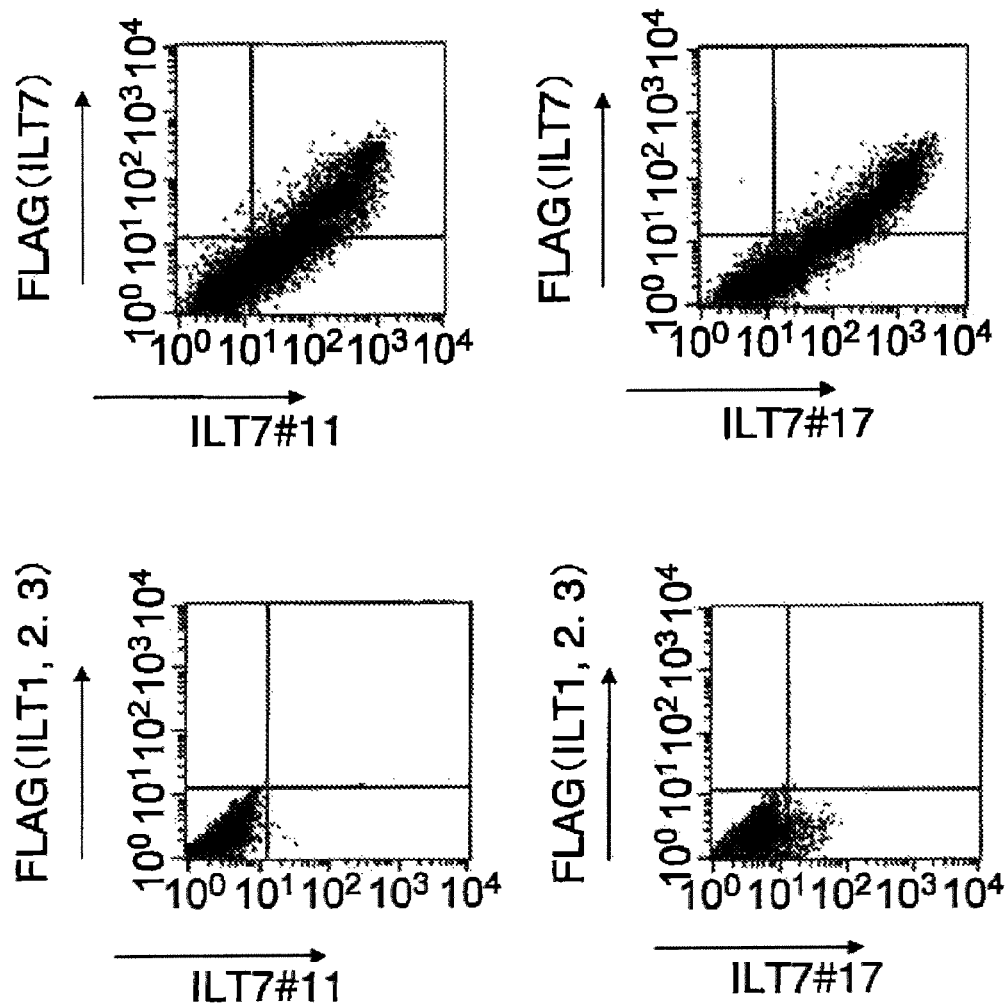
FIG. 10 is a result in which the responsiveness of the produced anti-ILT7 monoclonal antibodies ILT7#11 and ILT7#17 to ILT1, ILT2, and ILT3 molecules was examined using cells into which their expression vectors were introduced. The upper diagram shows the results where the responsiveness to cells in which ILT7 molecules with a FLAG tag had been coexpressed with FcRγ was reaffirmed. The lower diagram shows the results where the responsiveness to cells into which ILT1, ILT2, ILT3, and FcRγ were introduced (left diagram: ILT7#11, right diagram: ILT7#17). The horizontal axis shows the responsiveness of each anti-ILT7 antibody.

As a result, any antibodies did not respond to the cells in which ILT1 was expressed. For this reason, it was suggested that these anti-ILT7 antibodies specifically recognized ILT7 molecules on IPCs (FIG. 10).

Example 3

Effect of Anti-ILT7 Antibody on Ability to Produce Human IFN

Figure 11:
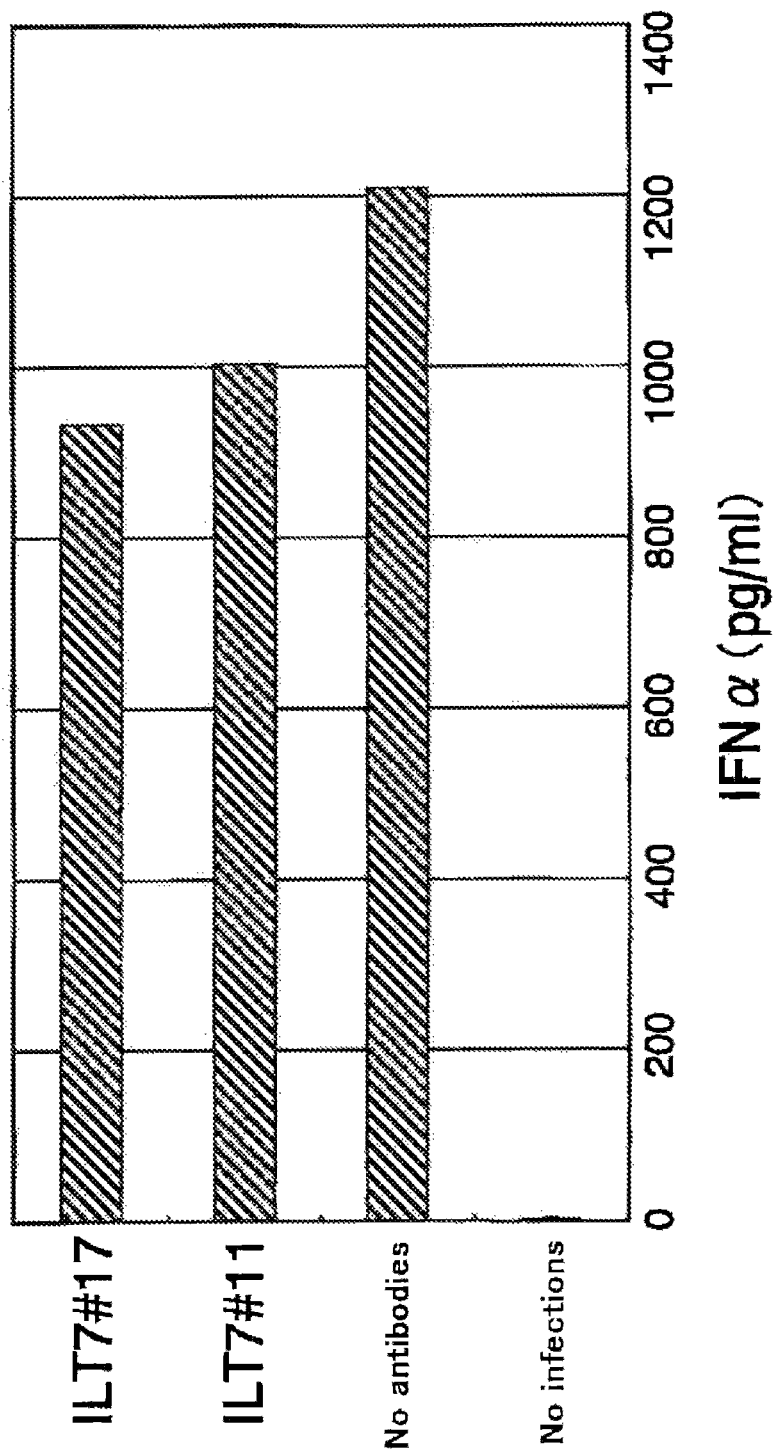
FIG. 11 is a diagram showing the effect of the produced anti-ILT7 monoclonal antibodies ILT7#11 and ILT7#17 on the interferogenic capacity of human lymphocytes. In the diagram, the horizontal axis shows IFNα concentration in a culture supernatant when human lymphocytes were stimulated by influenza virus and the vertical axis shows the treated antibodies. The term "no infections" indicates the results of cells which were not stimulated by influenza virus.

Human peripheral blood lymphocytes were inoculated into 96 well plate at $2 \times 10^5$ cells/well, which were reacted with 5 μg/mL of various antibodies at 37° C. After 1-hour culture, influenza virus PR8 was added thereto. After 24-hours culture, IFNα in the culture supernatant was measured by ELISA kit (Bender Med System). As a result, the production of IFN was inhibited by the addition of anti-ILT7 antibody (FIG. 11). Namely, it was found out that the IFN production by IPCs was affected by the anti-ILT7 antibody of the present invention.

Example 4

CDC Activity of Anti-ILT7 Antibody

A. Production of Anti-ILT7 Monoclonal Antibody

A clone which produces a monoclonal antibody was obtained in the same manner as described in A-1) to A-4) of Example 2. The responsiveness was examined in the same manner as described in B of Example 2 and the specificity was examined in the same manner as described in C of Example 2. As a result, hybridomas #37, #28, and #33, which produced anti-ILT7 monoclonal antibodies with good responsiveness and specificity, were obtained. CDC activity was measured as described below using anti-ILT7 monoclonal antibody in which three kinds of these hybridomas were produced.

B. Determination of CDC Activity

B-1) On the previous day of production of target Production of target cell line (ILT7-CHO cell line), the following DNA was introduced into CHO-k1 cells, which were inoculated so as to be $6 \times 10^5$ cells per one dish (6 cmφ) using Effectene Transfection Reagent (manufactured by QIAGEN) and then resistant strains were selected using 800 μg/ml of Zeocin (manufactured by Invitrogen).

Introduced DNA: pcDNA3.1-C-FLAG ILT7 1 μg+pME18X-Myc FcRγ 2 μg

Thereafter, a cell line, which highly expressed ILT7, was obtained using the cell sorter (BD FACSAria, manufactured by Becton Dickinson). It was confirmed that the selected cell line highly expressed ILT7 by FCM analysis. Operation of FCM analysis was carried out in accordance with the method as described in A-4) of Example 2 except that BD FACSCaliber (manufactured by BD) was used for FCM. The following antibodies were used for a primary antibody and a secondary antibody, respectively.

Primary antibody: 5 μg/ml mouse anti-ILT7 antibody (#37), Secondary antibody: R-phycoerythrin (R-PE)-conjugated goat anti-mouse immunoglobulin specific polyclonal antibody (BD)

B-2) Response of Target Cells to Anti-ILT7 Antibodies

The obtained target cells as described in B-1) (ILT7-CHO cell) were recovered using 5 mM EDTA/PBS solution, which were suspended in CDC medium with the following composition so as to be a concentration of $4 \times 10^5$ cells/ml. The suspension was aliquoted into each 96-well plate at 50 μl/well.

CDC medium:
RPMI1640
0.1% BSA
100 units/ml Penicillin
100 μg/ml Streptomycin
10 mM Hepes (pH 7.6)
2 mM L-Glutamin 50 μl of anti-ILT7 antibody solution prepared by CDC medium was added to each well and mixed so that the final concentration of antibodies should be 0.1 μg/ml, 0.5 μg/ml, 1 μg/ml, and 5 μg/ml. Further, 50 μl of CDC medium containing a complement with the following composition was added thereto and mixed so that the final complement concentration should be 6%, followed by culturing at 37° C. for 2 hours.
CDC medium containing a complement:
1 ml of complement of juvenile rabbit (Catalog No.: CL3441, manufactured by CEDARLANE)
CDC medium (vide supra)

Then, the suspension was centrifuged (centrifugal condition: at 250 G for 4 minutes) and the supernatant was recovered while paying attention not to be contaminated with cells. LDH in the supernatant was measured by an ordinary method, which was determined as "The amount of LDH leaked from the target cell by the complement activity" (Experimental Sample).

The following parameters were also prepared in order to determine CDC activity.
  Target Cell Spontaneous LDH Release: only target cells were cultured in the same volume as the sample and prepared.
  Target Cell Maximum LDH Release: only target cells were cultured in the same volume as the sample, and then TritonX-100 solution included with the kit was added thereto 60 minutes before recovery of the supernatant so that the final concentration should be 0.8% and prepared.
  Volume Correction Control: the same amount of TritonX-100 as that added when Target Cell Maximum LDH Release was prepared was added to the culture medium of the same volume as the sample and prepared.
  Culture Medium Background: the culture medium of the same volume as the sample and the solution to which complement containing CDC medium was added to the culture medium so as to be the same volume as the sample were prepared.

Figure 12:
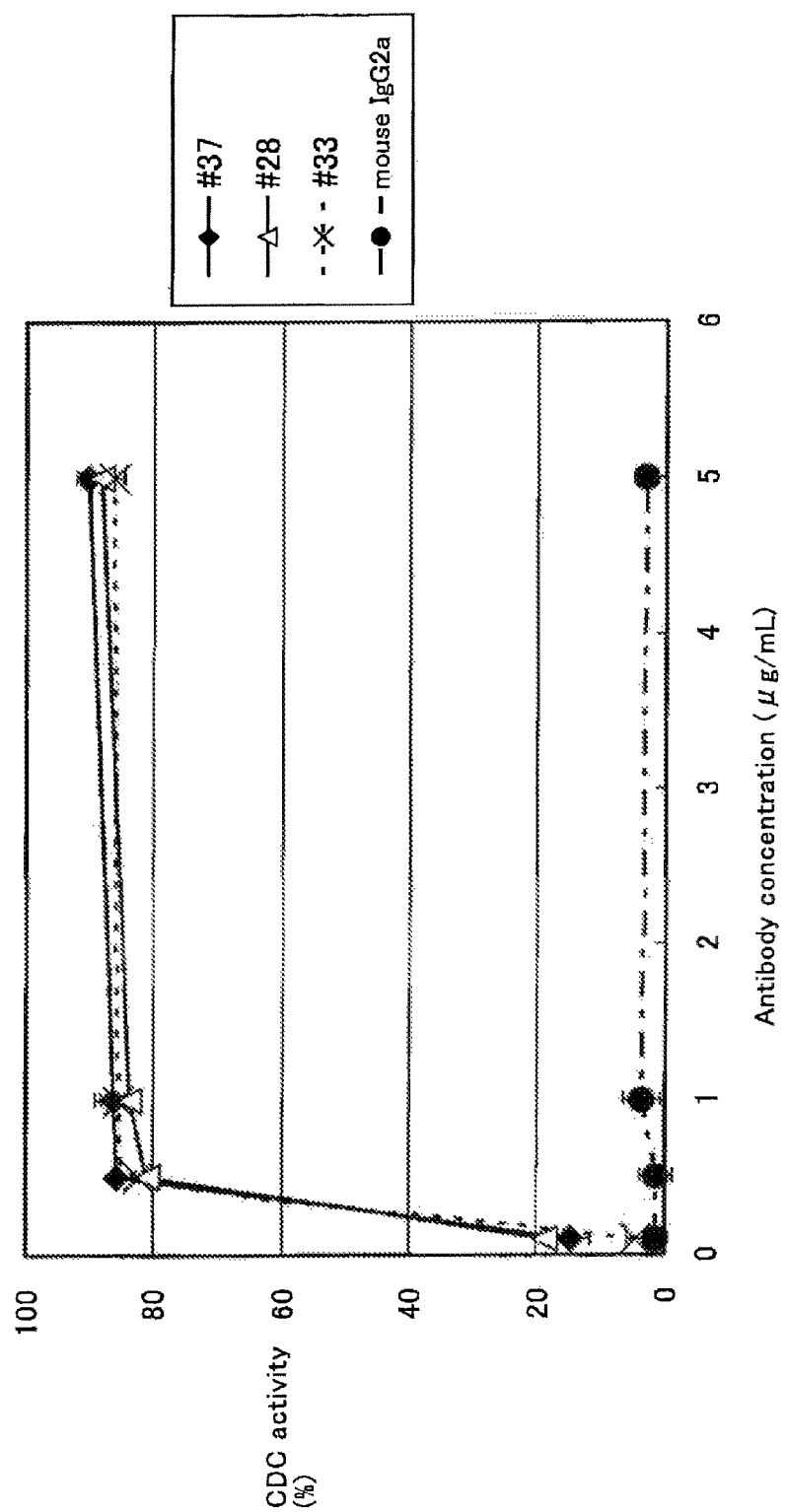
FIG. 12 is a diagram showing CDC activity of the produced anti-ILT7 monoclonal antibodies ILT7#37, ILT7#28, and ILT7#33. Even when anti-ILT7 monoclonal antibodies obtained from any hybridoma were used, 80% or more of CDC activity was exhibited at the antibody concentration of 0.1 µg/ml or higher. In the case of antibodies other than anti-ILT7 monoclonal antibody, CDC activity to target cells was not observed.

The same volume of culture medium as the sample was subtracted from the absorbance of Target Maximum and Target Spontaneous. The solution to which complement containing CDC medium was added to the culture medium so as to be the same volume as the sample was subtracted from the absorbance of Experimental Sample and corrected. The CDC activity was calculated by the following equation. The results are shown in Table 1 and FIG. 12. Even in the case where anti-ILT7 monoclonal antibodies obtained from any hybridoma were used, 80% or more of CDC activity was exhibited when the antibody concentration was 0.5 μg/ml or more.

$$CDC\ activity\ (\%) = \frac{Experimental\ Sample - Target\ Spontaneous}{Target\ Maximum - Volume\ Control - Target\ Spontaneous} \times 100$$

TABLE 1

| | Antibody concentration (μg/ml) | Cytotoxicity (Aver) | Cytotoxicity (STD) |
|---|---|---|---|
| #37 | 0.1 | 14.78 | 3.16 |
| | 0.5 | 85.50 | 0.60 |
| | 1 | 86.13 | 2.93 |
| | 5 | 90.26 | 1.87 |

TABLE 1-continued

| | Antibody concentration (μg/ml) | Cytotoxicity (Aver) | Cytotoxicity (STD) |
|---|---|---|---|
| #28 | 0.1 | 18.52 | 0.60 |
| | 0.5 | 80.97 | 1.62 |
| | 1 | 83.64 | 1.99 |
| | 5 | 88.17 | 3.32 |
| #33 | 0.1 | 4.42 | 1.58 |
| | 0.5 | 82.16 | 3.35 |
| | 1 | 85.39 | 2.78 |
| | 5 | 86.18 | 1.71 |
| Mouse IgG2a | 0.1 | 1.53 | 0.60 |
| | 0.5 | 1.47 | 2.50 |
| | 1 | 3.68 | 2.90 |
| | 5 | 3.06 | 1.72 |
| no Ab | 0 | 2.10 | 0.49 |

Comparative Example 1

Exactly the same operation was performed in the same manner as described in B and C of Example 4 except that mouse IgG2a was used in place of anti-ILT7 antibody. The results are shown in Example 4 as well as Table 5 and Fig. The CDC activity to the target cells was not observed in antibodies other than anti-ILT7 monoclonal antibody.

Example 5

Internalization of Anti-ILT7 Antibody to Target Cells

A. Anti-ILT7 Monoclonal Antibody
The following anti-ILT7 monoclonal antibodies were used.
Anti-ILT7 monoclonal antibodies: #17, #26, #37, #28, and #33
B. Observation of Internalization
B-1) Production of Target Cell Line (ILT7-CHO Cell Line)
The target cell line (ILT7-CHO cell line) was produced in the same manner as described in B-1 of Example 4.
B-2) Response of Target Cells to Anti-ILT7 Antibody
The recovered ILT7-CHO cells were suspended in ice-cold buffer (T(−)+10% FBS) with the following composition at $1 \times 10^6$ Cells/mL using 5 mM of EDTA/PBS solution.
T (−) medium:
RPMI1640
100 units/ml Penicillin
100 μg/ml Streptomycin
10 mM Hepes (pH 7.6)
2 mM L-Glutamin
1 mM sodium pyruvate
50 μM 2-mercaptoethanol
10% heat inactivated Fetal Bobine Serum
1 mL of suspension as described above was placed into a 15 mL centrifugal tube, which was centrifuged (centrifugal condition: at 1200 rpm, at 4° C., for 5 minutes) and then the supernatant was discarded. 200 μL of anti-ILT7 monoclonal antibody suspension of (10 μg/mL) was added to cell pellets, which was mixed and incubated at 4° C. for 30 minutes, followed by washing with ice-cold T (−) medium twice (the amount of the medium used: 10 mL per washing, centrifugal condition: at 1200 rpm, at 4° C., for 5 minutes).
B-3) Modification of ILT7-Anti-ILT7 Antibody Immune Complex Present on the Surface of Target Cells
Subsequently, ILT7-anti-ILT7 antibody immune complex present on the surface of cells was modified with a secondary antibody, which was labeled with fluorescence for detection. Specific method is described below. APC-labeled goat anti-mouse IgG polyclonal antibody (Catalog number: 550826BD, manufactured by Biosciences) containing ice-cold T (−) medium was added to cell pellets obtained as described in B-2), which was incubated with shading at 4° C. for 20 minutes, followed by washing with ice-cold T (−) medium twice (the amount of the medium used: 10 mL per washing, centrifugal condition: at 1200 rpm, at 4° C., for 5 minutes). Then, ice-cold T (−) medium was added thereto, which was used as 1×10$^6$ Cells/mL of suspension.

B-4) Induction of Internalization by Incubation at 37° C.

The suspension obtained as described in B-3 was equally divided into two tubes (i.e. tubes (a) and (b)). The tubes (a) and (b) were incubated at 37 and 4° C., respectively, under shading condition for 60 minutes. After the incubation, 1% FBS/PBS (ice-cold) was added thereto in order to stop internalization. The resulting solution was centrifuged (centrifugal condition: at 1200 rpm, at 4° C., for 5 minutes) and then the supernatant was discarded, followed by washing with 1% of FBS/PBS (ice-cold) twice (the amount of the solution: 10 mL per washing, centrifugal condition: at 1200 rpm, at 4° C., for 5 minutes).

B-6) Modification of ILT7-Anti-ILT7 Antibody Immune Complex Remained on the Surface of Target Cells after Incubation ILT7-anti-ILT7 antibody immune complex remained on the cell surface after incubation was modified with a tertiary antibody in order to detect, by fluorescence. Specific method is described below. 20 µL of suspension containing tertiary antibodies (FITC-labeled donkey anti-goat IgG antibody (Catalog number: sc-2024, manufactured by Santa cruz biotechnology)) was added to cell pellets obtained as described in B-4), which was mixed and allowed to stand at 4° C. for 15 minutes under shading condition. The resulting solution was washed with (the amount of the solution: 10 mL per washing, centrifugal condition: at 1200 rpm, at 4° C., for 5 minutes).

B-5) Analysis of Anti-ILT7 Antibody Present in Target Cells

Subsequently, 150 µL of 1% FBS/PBS was added to cell pellets obtained as described in B-5), which was suspended and collected into a 1.2 ml microtiter tube, followed by performing FCM analysis. In analysis, the mean fluorescence intensity (MPI) of each cell was analyzed separately in FITC and APC. Further, the fluorescence intensity ratio (%) was calculated by the following equation.

$$\text{Fluorescence intensity ratio (\%)} = \frac{\text{Mean fluorescence intensity of cells incubated at 37° C. for 60 minutes}}{\text{Mean fluorescence intensity of cells incubated at 4° C. for 60 minutes}} \times 100$$

Figure 13:
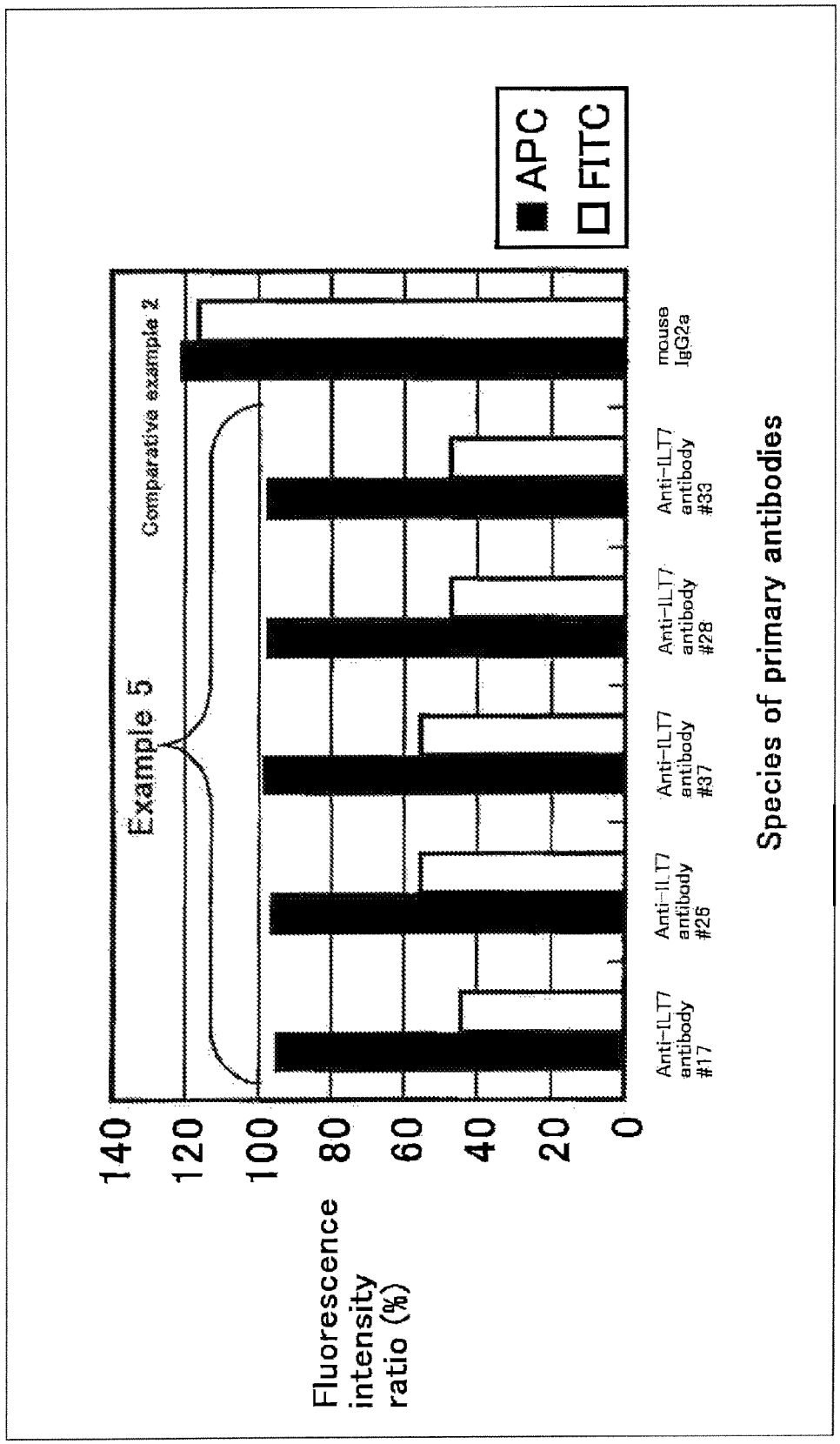
FIG. 13 is a diagram showing internalization to target cells of the produced anti-ILT7 monoclonal antibodies ILT7#17, ILT7#26, ILT7#37, ILT7#28, and ILT7#33.

The results are shown in Table 2, Table 3, and FIG. 13.

TABLE 2

| | FITC | | | APC | | |
|---|---|---|---|---|---|---|
| | Mean fluorescence intensity Temperature of incubation (° C.) | | Fluorescence intensity ratio | Mean fluorescence intensity Temperature of incubation (° C.) | | Fluorescence intensity ratio |
| | 4 | 37 | (%) | 4 | 37 | (%) |
| #17 | 35.7 | 15.9 | 44.5 | 1384 | 1320 | 95.4 |
| #26 | 29.8 | 16.5 | 55.4 | 844 | 816 | 96.7 |
| #37 | 51.0 | 28.5 | 55.9 | 2194 | 2155 | 98.2 |

TABLE 2-continued

| | FITC | | | APC | | |
|---|---|---|---|---|---|---|
| | Mean fluorescence intensity Temperature of incubation (° C.) | | Fluorescence intensity ratio | Mean fluorescence intensity Temperature of incubation (° C.) | | Fluorescence intensity ratio |
| | 4 | 37 | (%) | 4 | 37 | (%) |
| #28 | 40.6 | 19.3 | 47.5 | 1746 | 1709 | 97.9 |
| #33 | 47.7 | 22.6 | 47.4 | 1882 | 1845 | 98.0 |
| IgG2a | 3.7 | 4.2 | 116.2 | 3 | 3.64 | 121.3 |

TABLE 3

| | Species of primary antibodies | Fluorescence intensity ratio (%) | |
|---|---|---|---|
| | | APC | FITC |
| Example 5 | Anti-ILT7 antibody #17 | 95.4 | 44.5 |
| | Anti-ILT7 antibody #26 | 96.7 | 55.4 |
| | Anti-ILT7 antibody #37 | 98.2 | 55.9 |
| | Anti-ILT7 antibody #28 | 97.9 | 47.5 |
| | Anti-ILT7 antibody #33 | 98.0 | 47.4 |
| Comparative example 2 | Mouse IgG2a | 121.3 | 116.2 |

The fluorescence intensity of FITC is an indicator of the amount of ILT7-anti-ILT7 antibody immune complex remained on the cell surface after incubation. The mean fluorescence intensity of FITC as to the cells incubated at 37° C. for 60 minutes fell to about 50% as compared with the cells incubated at 4° C.

On the other hand, APC fluorescence intensity is an indicator of the amount of ILT7-anti-ILT7 antibody immune complex presented on the cell surface before incubation. ILT7-anti-ILT7 antibody immune complex is detected regardless of whether it is present on the cell surface or incorporated into cells after incubation. In Example 5, APC fluorescence intensity after the incubation in the case of incubation at 37° C. was equivalent to that in the case of incubation at 4° C. It shows that ILT7-anti-ILT7 antibody immune complex may be present in any site of target cells even when the incubation is performed at either temperature. As mentioned above, it was found that the anti-ILT7 monoclonal antibody evoked the internalization of ILT7 by the incubation at 37° C.

Comparative Example 2

Exactly the same operation was performed in the same manner as described in Example 5 except that mouse IgG2a was used in place of anti-ILT7 antibody. The results are shown in Example 5 as well as Table 2, Table 3, and FIG. 13. In the case where the mouse IgG2a was used, any changes in the fluorescence intensity of FITC and APC were not observed, thus was found that the mouse IgG2a did not evoke the internalization ILT7.

Example 6

Concerning the Structure of Mouse Anti-Human ILT7 Monoclonal Antibody

[Sequences of Variable Regions]
A. Cloning of cDNA Encoding Variable Region of Mouse Anti-ILT7 Antibody
A-1) Concerning Hybridomas which Produce Mouse Anti-ILT7 Antibodies The following hybridomas were used as hybridomas which produce mouse anti-ILT7 antibodies.
Hybridoma #11 (Accession number: FERM BP-10704)
Hybridoma #17 (Accession number: FERM BP-10705)
A-2) Isolation of the Total RNAs The total RNAs were isolated from hybridomas described in A-1) using a commercially available kit "RNeasy Mini Kit" (Catalog number: 74106, manufactured by Qiagen) in accordance with the instruction attached to the kit. In both cases, about 200 μg of the total RNAs was obtained from 1×10$^7$ hybridomas.

A-3) Amplification and Fragmentation of cDNA Encoding a Mouse Heavy Chain Variable Region cDNA encoding a mouse heavy chain variable region was amplified by 5' RACE method using 5 μg of the total RNAs isolated as described in A-2. As for amplification, commercially available kit "5' RACE System for Rapid Amplification of cDNA ENDs, Version 2.0 Kit" (Catalog number: 18374-058, manufactured by Invitrogen) was used. It will be specifically described as follows. First, a first strand cDNA was synthesized from the total RNAs obtained as described in A-2) by reverse transcriptase. The base sequences of antisense primers (GSP1) used at the time are shown in Table 4.

TABLE 4

Primers used for amplification of a gene encoding a mouse heavy chain variable region

| Used hybridomas | Names of primers | SEQ ID No. | Sequence |
|---|---|---|---|
| #11 | Mu IgG3VH5RACE-GSP1 | 30 | 5' CCA TAG TTC CAT TTT ACA GTT ACC 3' (24-mer) |
|  | Mu IgG3VH5RACE-GSP2 | 31 | 5' GGG ACC AAG GGA TAG ACA GA 3' (20-mer) |
| #17 | Mu IgG2aVH5RACE-GSP1 | 32 | 5' TCC AGA GTT CCA GGT CAA GGT CAC 3' (24-mer) |
|  | Mu IgG2aVH5RACE-GSP2 | 33 | 5' GCC AGT GGA TAG ACC GAT GG 3' (20-mer) |

Subsequently, the total RNAs were degraded by RNaseH and the first strand cDNA remained as a single strand was purified by low-melting point agarose method (1.5%). Further, dC (i.e. nucleotide homopolymer) was attached to the 3'-terminus of the first chain cDNA using terminal deoxynucleotidyl transferase (TdT). cDNA was amplified by PCR method using an anchor primers (SEQ ID NO: 34) having a nucleotide polymer complementary to dC (anchor sequence) at 3'-terminus and antisense primers (GSP2) shown in Table 4. Further, the obtained PCR products were used as templates. cDNA was amplified by Nested PCR method using AUAP primer (SEQ ID NO: 35) and antisense primers (GSP2) shown in Table 4. Further, the PCR products were purified by low-melting point agarose method (1.5%).

```
Anchor primer for 5'RACE
                                        (SEQ ID NO: 34)
5'-GGC CAC GCG TCG ACT AGT ACG GGI IGG GII
GGG IIG-3'
(36-mer)

AUAP primer gor 5'RACE
                                        (SEQ ID NO: 35)
5'-GGC CAC GCG TCG ACT AGT AC-3'
(20-mer)
```

A-4) Amplification and Fragmentation of cDNA Encoding Mouse Light Chain Variable Region cDNA encoding a mouse light chain variable region was amplified from the total RNAs isolated as described in A-2) in the same manner as described in A-3). The base sequences of primers used at the time is shown in Table 5. The obtained PCR products were purified by low-melting point agarose method (1.5%).

TABLE 5

Primers used for amplification of a gene encoding a mouse light chain variable region

| Used hybridomas | Names of primers | SEQ ID No. | Sequence |
|---|---|---|---|
| #11, #17 | Mu IgVL5RACE-GSP1 | 36 | 5' TTC ACT GCC ATC AAT CTT CCA CTT 3' (24-mer) |
|  | Mu IgVL5RACE-GSP2 | 37 | 5' GAT GGA TAC AGT TGG TGC AGC 3' (21-mer) |

A-5) Confirmation of Base Sequence of cDNA and Determination of CDR Region

A heavy chain variable region obtained as described in A-3) and cDNA fragment of light chain variable region obtained as described in A-4) were cloned to pCR4 Blunt-TOPO vector using a commercially available kit "Zero Blunt TOPO PCR Cloning Kit" (Catalog number: 1325137, manufactured by Invitrogen) in accordance with the instruction attached to the kit, which was then introduced into *Escherichia coli* competent cells to give *Escherichia coli* transformant. The above-mentioned plasmid was obtained from the transformant, then cDNA base sequence in the plasmid was confirmed using an automatic DNA sequencer "PCR-based ABI PRISM 3100 Genetic Analyzer" (manufactured by Applied Biosystems). Correct sequences were extracted by excluding transcripts obtained from an inactive RNA due to frame shift and nonsense mutations around the complementarity-determining region (hereinafter referred to as "CDR region"). Further, the homology of cDNA base sequence comprised in the plasmid was compared with Kabat database and sequences of the CDR region and the variable region in respective variable regions were determined. Also, as for the hybridoma #37 produced in Example 4, sequences of the CDR region and the variable region in variable regions were determined in the same procedure as described in A-1) to A-5) of Example 6 using hybridoma #17. cDNA base sequences of the heavy chain variable regions and light chain variable regions of the anti-ILT7 monoclonal antibodies produced by each hybridoma and amino acid sequences encoded by the sequences are shown in the following SEQ ID NOs.

|  | Heavy chain variable region | Light chain variable region |
|---|---|---|
| #11 | SEQ ID NO: 38 (base sequence) | SEQ ID NO: 40 (base sequence) |
|  | SEQ ID NO: 39 (amino acid sequence) | SEQ ID NO: 41 (amino acid sequence) |
| #17 | SEQ ID NO: 42 (base sequence) | SEQ ID NO: 44 (base sequence) |
|  | SEQ ID NO: 43 (amino acid sequence) | SEQ ID NO: 45 (amino acid sequence) |
| #37 | SEQ ID NO: 46 (base sequence) | SEQ ID NO: 48 (base sequence) |
|  | SEQ ID NO: 47 (amino acid sequence) | SEQ ID NO: 49 (amino acid sequence) |

[Confirmation of Isotype of Constant Region]

As for the hybridoma culture supernatant, the isotype of the constant region of the produced monoclonal antibody was confirmed using a commercially available mouse monoclonal antibody isotyping kit (Catalog number: MMT1, manufactured by Serotec Product). The heavy chain constant region of mouse anti-human ILT7 antibody #11 was Igγ3 and the light chain constant region was Igκ. Further, each of the heavy chain constant regions of mouse anti-human ILT7 antibody #17 and mouse anti-human ILT7 antibody #37 was Igγ2a and each of the light chain constant region was Igκ.

Example 7

Production of Chimeric Antibodies

A. Cloning of cDNA Encoding Human IgG Constant Region

Human IgG1 heavy chain constant region and human Ig kappa light chain constant region were selected from cDNA library of human IPCs. Then, the selected regions were cloned to pCR4 Blunt-TOPO vector using a commercially available kit "Zero Blunt TOPO PCR Cloning Kit" (Catalog number: 1325137, manufactured by Invitrogen) in accordance with the instruction attached to the kit, which was then introduced into *Escherichia coli* competent cells to give *Escherichia coli* transformant. The above-mentioned plasmid was obtained from the transformant, then cDNA base sequence in the plasmid was confirmed using an automatic DNA sequencer "PCR-based ABI PRISM 3100 Genetic Analyzer" (manufactured by Applied Biosystems).

B. Ligation of Variable Region with Constant Region and Cloning

The cDNA encoding the heavy chain constant region obtained as described in A and the cDNA encoding the heavy chain variable region obtained as described in A-5 of Example 6 was used, respectively. Both DNAs have a region in which a base sequence of DNA is overlapped. Then, double-stranded DNA was obtained by the overlap extension method using the region. Specific process is as follows.

C-1) Preparation of cDNA Encoding Heavy Chain of Chimeric ILT7 Antibody

The "plasmid with cDNA encoding heavy chain variable regions of #11 and #17" which was obtained as described in A-5) was digested with restriction enzymes NotI and XbaI, which was purified by the agarose gel method (1.5%). The resulting products were dissolved in each TE buffer with the following composition so as to be 100 pmol/μL to prepare a solution of the cDNA fragment encoding the heavy chain variable region.

TE buffer:
10 mM Tris-HCl
1 mM EDTA
pH 7.5 to 8.0

Further, the "plasmid with cDNA encoding the heavy chain constant region" obtained as described in B was treated in the same manner as described above to prepare 100 pmol/μL of solution. Subsequently, both solutions were mixed, and then both of the overlap regions were hybridized by first keeping them at 70° C. for 10 minutes and next keeping them at 37° C. for 5 minutes. Thereafter, cDNA was amplified by PCR method and the obtained cDNA was digested with restriction enzymes NotI and XbaI, which was purified by the low-melting point agarose gel method (1.5%).

C-2) Preparation of cDNA Encoding Light Chain of Chimeric ILT7 Antibody

The cDNA encoding the light chain constant region obtained as described in A and the cDNA encoding the light chain variable region obtained as described in A-5 of Example 6 was used, respectively. cDNA encoding the light chain of chimeric ILT7 antibody was obtained in the same manner as described in C-1) using these cDNAs.

C-3) Cloning cDNA obtained as described in C-1) was cloned to plasmid vector pcDNA3.1-Zeocin (manufactured by Invitrogen) using NotI and XbaI as cloning sites to produce a chimeric ILT7 antibody heavy chain expression vector. Further, cDNA obtained as described in C-2) was cloned to plasmid vector pcDNA3.1-hygromycin (manufactured by Invitrogen) using NotI and XbaI as cloning sites to produce a chimeric ILT7 antibody light chain expression vector. Names of each vector are shown in Table 6.

TABLE 6

Names of plasmid vectors

|   | Chimeric ILT7 antibody heavy chain for expression | Chimeric ILT7 antibody light chain for expression |
|---|---|---|
| #11 | pcDNA-#11VH | pcDNA-#11VL |
| #17 | pcDNA-#17VH | pcDNA-#17VL |

D. Expression of Chimeric ILT7 Antibody

D-1) Transient Transformation

1 μg of chimeric ILT7 antibody heavy chain expression vector and 1 μg of chimeric ILT7 antibody light chain expression vector, which were obtained as described in C-3), were co-transfected to 293T cells using effectine transfection kit (Catalog number: 301427, manufactured by Qiagen). Thereafter, the resulting products were cultured at 37° C. using 2% Low IgG FBS-added DMEM culture medium with the following composition.

2% Low IgG FBS-added DMEM culture medium:
DMEM culture medium (Catalog number: D5796, manufactured by Sigma)
2% Low IgG FBS (Catalog number: SH30151.03, manufactured by HyClone)
2 mM L-Glutamin
100 U/ml Penicillin
100 μg/ml Streptomycin
pH 7.2 to pH 7.4

After introduction of vectors, the resulting medium was cultured for 96 hours and the culture supernatant was collected. Then, the cell fragments were removed by centrifugation to give a crude antibody solution.

D-2) Homeostasis Transformation

1 μg of chimeric ILT7 antibody heavy chain expression vector and 1 μg of chimeric ILT7 antibody light chain expression vector, which were obtained as described in C-3), were co-transfected to YB 2/0 cells (cells derived from rat myeloma, ATCC#CRL-1622) using effectine transfection kit (Catalog number: 301427, manufactured by Qiagen). Among the used plasmid vectors, the vector for the heavy chain expression is a marker for Zeocin resistance and the vector for the light chain expression is a marker for hygromycin resistance. Therefore, cells into which both vectors were introduced can be grown in a culture medium to which Zeocin and hygromycin are added at the same time. Then, the cells were cultured in RPMI culture medium to which Zeocin and hygromycin were added and a resistant strain was selected.

Zeocin-hygromycin-added RPMI culture medium:
RPMI1640 culture medium (Catalog number: R8758, manufactured by Sigma)
10% FBS
0.01 M HEPES (N-2-hydroxyethylpiperazine-N'-2-ethanesulfonic acid)
1 mM Sodium pyruvate
2 mM L-Glutamine
100 U/ml Penicillin
100 μg/ml Streptomycin
55 μM 2-mercaptoethanol
0.5 mg/ml Zeocin
0.5 mg/ml Hygromycin
pH 7.2 to pH 7.4

Three days after that, the amount of antibody production in the culture supernatant was determined by the ELISA method. ILT7 chimeric-antibody producing cell line with a high expression level and cells sufficiently increased was selected. Furthermore, a single cloning of the selected cell lines was performed by the cell sorter method to obtain the following cell lines.

11 ILT7 chimeric-antibody-producing cell line: #11-5 cell line and #11-16 cell line

17 ILT7 chimeric-antibody-producing cell line: #17-24 cell line

The above-mentioned cell lines (#11-5 cell line, #11-16 cell line, and 17-24 cell line) were respectively cultured in 5% FBS-added RPMI culture medium with the following composition. The incubation temperature and incubation time were set to 37° C. and 96 hours, respectively.

5% FBS-added RPMI culture medium:
RPMI1640 culture medium (Catalog number: R8758S, manufactured by Sigma)
5% FBS
0.01 M HEPES
1 mM Sodium pyruvate
2 mM L-Glutamin
100 U/ml Penicillin
100 μg/ml Streptomycin
55 μM 2-mercaptoethanol
pH 7.2 to pH 7.4

The culture supernatant was collected and then the cell fragments were removed by centrifugation to give a crude antibody solution.

E. Purification of Antibodies

Each of the crude antibody solutions obtained as described in D-1 and D-2 was purified by protein A affinity column (rProtein A Sepharose FF, Catalog number: 17-1279-01, manufactured by Amershram Pharmacia). Purification conditions are as follows. Affinity purification was carried out using PBS (−) buffer with the following composition as an adsorption buffer and 0.1M sodium citrate buffer (pH 3) as an elution buffer in accordance with the attached instruction manual. 1 M Tris-HCl (pH 8.0) was added to the eluted fractions to adjust the pH to around 7.2. The ODs at 450 to 620 nm were measured and then wells showing positive reaction were selected. With reference to the concentration of purified antibodies, the absorbance at 280 nm was determined and calculated based on 1.38 OD/mg/ml. Relationships among chimeric ILT7 antibodies obtained, hybridomas from which the variable region gene was derived, and host cells were summarized in Table 7.

PBS (−) buffer:
0.2 g/L Monopotassium dihydrogen phosphate
0.2 g/L Potassium chloride
8 g/L Sodium chloride
1.15 g/L Disodium monohydrogen phosphate anhydrous

TABLE 7

Produced chimeric antibodies

| Names of produced chimeric antibodies | Used hybridomas | Form of transformation | Introduced cells |
|---|---|---|---|
| #11 ILT7 chimeric antibody | #11 | Transient manner | 293T |
| #17 ILT7 chimeric antibody | #17 | | |
| #11-5 ILT7 chimeric antibody | #11 | Homeostasis | YB 2/0 |
| #11-16 ILT7 chimeric antibody | #11 | | |
| #17-24 ILT7 chimeric antibody | #17 | | | cDNA base sequences and amino acid sequences of the heavy and light chains of the produced chimeric antibodies are shown below, respectively. In each amino acid sequence, the amino acid sequence from N-terminus to −1 is a signal sequence and the amino acid sequence from 1 to C terminus is an amino acid sequence of a mature protein. That is, heavy and light chains, which constitute these chimeric antibodies, consist of the amino acid sequence from 1 to C terminus of each of the following amino acid sequences.

| | Heavy chain | Light chain |
|---|---|---|
| #11 | SEQ ID NO: 50 (base sequence) SEQ ID NO: 51 (amino acid sequence) | SEQ ID NO: 52 (base sequence) SEQ ID NO: 53 (amino acid sequence) |
| #17 | SEQ ID NO: 54 (base sequence) SEQ ID NO: 55 (amino acid sequence) | SEQ ID NO: 56 (base sequence) SEQ ID NO: 57 (amino acid sequence) |

INDUSTRIAL APPLICABILITY

The present invention provided the immunogen useful in producing the antibody specifically recognizing human ILT7 and the method for producing anti-ILT7 antibody using the immunogen. The antibody specifically recognizing human ILT7 of the present invention specifically recognizes ILT7 under the presence of ILT family. Therefore, the antibody of the present invention can be used for the detection and isolation of human ILT7. For example, the localization of ILT7 can also be analyzed using the antibody of the present invention.

It is considered that ILT7 is a molecule closely related to the differentiation and function of IPCs or dendritic cells. Therefore, the antibody, which recognizes ILT7 with high specificity, is useful for the analysis of function of IPCs or dendritic cells. IPC-like (having the characteristic in which BDCA-2 is expressed) cancer cells are known (Chaper of L et al. Eur. J. Immunol. 34; 418-426, 2004, Maeda T et al., Int. J. Hematol. 81; 148-154, 2005). Confirmation of the expression of ILT7 in these cells may allow for the diagnosis of cancer and a therapeutic agent.

In the case of autoimmune diseases, for example, the deep relationship between IFNα produced by IPCs and the development of psoriasis, which is a skin disease, is pointed out (Nestle F O et al., J. Exp. Med. 202, 135-143, 2005). Therefore, the severity of psoriasis can be examined by identifying IPCs in the skin tissue of psoriasis patients, i.e. in biopsy specimens using the anti-ILT7 antibody.

It is known that the development of AIDS in HIV-infected patients is correlated with the number of IPCs. Namely, lots of IPCs have been observed in patients who do not show symptoms and the reduction in IPCs has been observed in the onset (Soumells V. et al., Blood 98; 906-912, 2001). Therefore, it is effective in predicting the prognosis of virus infection, such as HIV.

For example, ILT7 is a molecule which is expressed specifically in human IPCs. Therefore, the anti-ILT7 antibody of the present invention can be used to detect, identify, or isolate IPCs. IPCs are cells which produce most of the type 1 interferon. Therefore, the detection, identification, or isolation is an important objective in diagnosis and study of diseases that involve type 1 interferon. As such diseases, various autoimmune diseases and infections that interferon is involved in the formation of the pathological condition may be illustrated.

Additionally, the anti-ILT7 antibody of the present invention has the inhibitory effect on the activity of IPCs. Therefore, the activity of IPCs can be inhibited by using the anti-ILT7 antibody of the present invention. Furthermore, the diseases that involve type 1 interferon can be treated by inhibiting the activity of IPCs. Specifically, the anti-ILT7 antibody of the present invention is useful for various autoimmune diseases and infections that interferon is involved in the formation of the pathological condition. Particularly, since the anti-ILT7 antibody has a high specificity, it can remove IPCs efficiently.

The invention claimed is:

1. An isolated polynucleotide encoding a monoclonal antibody which binds to an extracellular domain of human ILT7 or a fragment comprising its antigen binding region wherein the monoclonal antibody comprises an amino acid sequence selected from any of the following combinations (a) to (c) as the heavy chain variable region and the light chain variable region:
   a) a heavy chain variable region of SEQ ID NO: 39 and a light chain variable region of SEQ ID NO: 41;
   b) a heavy chain variable region of SEQ ID NO: 43 and a light chain variable region of SEQ ID NO: 45; and
   c) a heavy chain variable region of SEQ ID NO: 47 and a light chain variable region of SEQ ID NO: 49.

2. A vector comprising the polynucleotide according to claim 1.

3. An isolated transformed cell retaining the vector according to claim 2 in an expressible manner.

4. A method for producing a monoclonal antibody which binds to an extracellular domain of human ILT7, comprising the steps of: culturing the transformed cell according to claim 3; and recovering the monoclonal antibody from the culture.

* * * * *